United States Patent
Bonny

(10) Patent No.: US 9,290,538 B2
(45) Date of Patent: *Mar. 22, 2016

(54) CELL-PERMEABLE PEPTIDE INHIBITORS OF THE JNK SIGNAL TRANSDUCTION PATHWAY

(71) Applicant: XIGEN INFLAMMATION LTD., Limassol (CY)

(72) Inventor: Christophe Bonny, Lausanne (CH)

(73) Assignee: Xigen Inflammation Ltd., Limassol (CY)

(*) Notice: Subject to any disclaimer, the term of this patent is extended or adjusted under 35 U.S.C. 154(b) by 0 days.

This patent is subject to a terminal disclaimer.

(21) Appl. No.: 14/144,938

(22) Filed: Dec. 31, 2013

(65) Prior Publication Data

US 2014/0200187 A1 Jul. 17, 2014

Related U.S. Application Data

(62) Division of application No. 12/066,657, filed as application No. PCT/EP2006/008882 on Sep. 12, 2006, now Pat. No. 8,748,395.

(30) Foreign Application Priority Data

Sep. 12, 2005 (EP) .................. PCT/EP2005/009782

(51) Int. Cl.
  *C07K 14/47* (2006.01)
  *C07K 7/08* (2006.01)
  *C07K 14/005* (2006.01)

(52) U.S. Cl.
  CPC .............. *C07K 7/08* (2013.01); *C07K 14/005* (2013.01); *C07K 14/47* (2013.01); *C07K 14/4703* (2013.01)

(58) Field of Classification Search
  CPC .... C07K 14/005; C07K 14/47; C07K 14/473; C07K 7/08
  USPC ............... 514/21.2, 21.3, 21.4; 530/300, 324, 530/326, 350, 387.9
  See application file for complete search history.

(56) References Cited

U.S. PATENT DOCUMENTS

| | | |
|---|---|---|
| 4,631,211 A | 12/1986 | Houghten |
| 4,698,327 A | 10/1987 | Nagarajan et al. |
| 4,732,890 A | 3/1988 | Bonelli et al. |
| 5,169,933 A | 12/1992 | Anderson et al. |
| 5,597,895 A | 1/1997 | Gaynor et al. |
| 5,670,617 A | 9/1997 | Frankel et al. |
| 5,672,479 A | 9/1997 | Johnson et al. |
| 5,674,980 A | 10/1997 | Frankel et al. |
| 5,686,264 A | 11/1997 | Gaynor et al. |
| 5,747,641 A | 5/1998 | Frankel et al. |
| 5,756,684 A | 5/1998 | Johnson et al. |
| 5,804,604 A | 9/1998 | Frankel et al. |
| 5,840,313 A | 11/1998 | Vahlne et al. |
| 5,880,261 A | 3/1999 | Waeber et al. |
| 5,989,814 A | 11/1999 | Frankel et al. |
| 5,994,108 A | 11/1999 | Gaynor et al. |
| 5,994,109 A | 11/1999 | Woo et al. |
| 6,043,083 A | 3/2000 | Davis et al. |
| 6,117,632 A | 9/2000 | O'Mahony |
| 6,265,386 B1 | 7/2001 | Campbell |
| 6,284,456 B1 | 9/2001 | Jones et al. |
| 6,300,317 B1 | 10/2001 | Szoka et al. |
| 6,316,003 B1 | 11/2001 | Frankel et al. |
| 6,348,185 B1 | 2/2002 | Piwnica-Worms |
| 6,420,031 B1 | 7/2002 | Parthasarathy et al. |
| 6,448,283 B1 | 9/2002 | Ylikoski et al. |
| 6,495,663 B1 | 12/2002 | Rothbard et al. |
| 6,586,403 B1 | 7/2003 | Mathison et al. |
| 6,610,820 B1 | 8/2003 | Bonny |
| 6,630,351 B1 | 10/2003 | Monahan et al. |
| 6,653,443 B2 | 11/2003 | Zhang et al. |
| 6,673,908 B1 | 1/2004 | Stanton, Jr. |
| 6,740,524 B1 | 5/2004 | Akuta et al. |
| 6,780,970 B2 | 8/2004 | Bonny |
| 6,881,825 B1 | 4/2005 | Robbins et al. |
| 6,960,648 B2 | 11/2005 | Bonny |
| 7,034,109 B2 | 4/2006 | Bonny |
| 7,148,215 B2 | 12/2006 | Ratcliffe et al. |
| 7,166,692 B2 | 1/2007 | Karas |
| 7,635,681 B2 | 12/2009 | Bonny |
| 7,943,574 B2 | 5/2011 | Bonny |
| 8,063,012 B2 * | 11/2011 | Watt et al. ............. 514/1.1 |

(Continued)

FOREIGN PATENT DOCUMENTS

| EP | 0375040 | 12/1989 |
|---|---|---|
| EP | 0 679 716 A1 | 11/1995 |

(Continued)

OTHER PUBLICATIONS

Bogoyevitch et al., "Taking the cell by stealth or storm? Protein transduction domains (PTDs) as versatile vectors for delivery," DNA Cell Biol., 21(12):879-894 (2002).
InVivoGen, Inc., SP600125: MAP Kinase Inhibitor—Autophagy Inhibitor—JNK inhibitor, Downloaded Jun. 9, 2014.
Kelekar et al., "Bcl-2-family proteins: the role of the BH3 domain in apoptosis," Trends Cell Biol., 8(8):324-330 (1998).
Killick et al, "Clusterin regulates β-amyloid toxicity via Dickkopf-1-driven induction of the wnt-PCP-JNK pathway," Mol Psychiatry., 19(1):88-98 (2014).
Du H et al., JNK inhibition reduces apoptosis and neovascularization in a murine model of age-related macular degeneration, Proc Natl Acad Sci U S A. Feb. 5, 2013;110(6):2377-82. Epub Jan. 22, 2013.
Iyer S. et al., RDP58, a rationally designed peptide, inhibits multiple forms of pathogenic inflammation through the inhibition of p38MAPK and JNK, Biopolymers, vol. 71, No. 3, 061, p. 298, Jan. 2013.

(Continued)

*Primary Examiner* — Julie Ha
(74) *Attorney, Agent, or Firm* — Morgan, Lewis & Bockius LLP

(57) ABSTRACT

Protein kinase inhibitors and more specifically inhibitors of the protein kinase c-Jun amino terminal kinase are herein described. Additionally, JNK inhibitor sequences, chimeric peptides, nucleic acids encoding same as well as pharmaceutical compositions for treating pathophysiologies associated with JNK signaling are herein provided.

18 Claims, 7 Drawing Sheets

(56) References Cited

U.S. PATENT DOCUMENTS

| | | |
|---|---|---|
| 8,080,517 B2 | 12/2011 | Bonny |
| 8,236,924 B2 | 8/2012 | Bonny |
| 8,278,413 B2 | 10/2012 | Bonny |
| 2002/0042423 A1 | 4/2002 | Richert et al. |
| 2002/0103229 A1 | 8/2002 | Bhagwat et al. |
| 2003/0100549 A1 | 5/2003 | Salituro et al. |
| 2003/0104622 A1 | 6/2003 | Robbins et al. |
| 2003/0108539 A1 | 6/2003 | Bonny |
| 2003/0124113 A1 | 7/2003 | Hillman et al. |
| 2003/0148395 A1 | 8/2003 | Liu |
| 2003/0220480 A1 | 11/2003 | Bonny |
| 2004/0058875 A1 | 3/2004 | Gamache |
| 2004/0082509 A1 | 4/2004 | Bonny |
| 2004/0265879 A1 | 12/2004 | Iversen et al. |
| 2005/0059597 A1 | 3/2005 | Tymianski |
| 2005/0106695 A1 | 5/2005 | Bonny |
| 2006/0094753 A1 | 5/2006 | Pang et al. |
| 2006/0223807 A1 | 10/2006 | Davis et al. |
| 2006/0258706 A1 | 11/2006 | Saindane |
| 2006/0270646 A1 | 11/2006 | Graczyk et al. |
| 2007/0003531 A1 | 1/2007 | Mukherji et al. |
| 2007/0015779 A1 | 1/2007 | Griffin et al. |
| 2007/0060514 A1 | 3/2007 | Bonny |
| 2008/0008749 A1 | 1/2008 | Pearlman et al. |
| 2012/0101046 A1 | 4/2012 | Hirai et al. |
| 2012/0258982 A1 | 10/2012 | Cheung et al. |

FOREIGN PATENT DOCUMENTS

| | | |
|---|---|---|
| EP | 0 897 002 A2 | 2/1999 |
| EP | 1 364 949 A1 | 11/2003 |
| EP | 1676574 A2 | 7/2006 |
| JP | 58-146538 | 9/1983 |
| JP | 02-221294 | 4/1990 |
| JP | 2-221294 | 9/1990 |
| WO | 92-18138 A1 | 10/1992 |
| WO | 93-18759 A1 | 9/1993 |
| WO | 94-04562 A1 | 3/1994 |
| WO | 94-04686 | 3/1994 |
| WO | 94-05311 A1 | 3/1994 |
| WO | 94-23751 A1 | 10/1994 |
| WO | 95-34295 | 12/1995 |
| WO | 96/34093 | 10/1996 |
| WO | 97-05265 | 2/1997 |
| WO | 97-10836 | 3/1997 |
| WO | 98-11907 | 3/1998 |
| WO | 98-23781 A1 | 6/1998 |
| WO | 98-44106 A1 | 10/1998 |
| WO | 98-47913 A1 | 10/1998 |
| WO | 98-49188 | 11/1998 |
| WO | 98-51325 A2 | 11/1998 |
| WO | 98-51825 A1 | 11/1998 |
| WO | 98-52614 | 11/1998 |
| WO | 99-07728 A2 | 2/1999 |
| WO | 99-16787 A1 | 4/1999 |
| WO | 9920624 A1 | 4/1999 |
| WO | 99-49879 | 10/1999 |
| WO | 99-50282 A2 | 10/1999 |
| WO | 99-58561 A1 | 11/1999 |
| WO | 99-67284 A2 | 12/1999 |
| WO | 00-12587 A2 | 3/2000 |
| WO | 00-41719 A1 | 7/2000 |
| WO | 01-10888 A1 | 2/2001 |
| WO | 01-13957 A2 | 3/2001 |
| WO | 01-15511 A2 | 3/2001 |
| WO | 01-27268 | 4/2001 |
| WO | 01/39784 | 6/2001 |
| WO | 01/82975 | 11/2001 |
| WO | 02-31109 A2 | 4/2002 |
| WO | 02/32437 | 4/2002 |
| WO | 02-061105 A2 | 8/2002 |
| WO | 02-062396 A2 | 8/2002 |
| WO | 02-065986 A2 | 8/2002 |
| WO | 02-069930 A1 | 9/2002 |
| WO | 02-081504 A2 | 10/2002 |
| WO | 02-081505 A2 | 10/2002 |
| WO | 03/008553 | 1/2003 |
| WO | 03/057725 | 7/2003 |
| WO | 03-075917 A1 | 9/2003 |
| WO | 03-103698 A1 | 12/2003 |
| WO | 03-103718 A2 | 12/2003 |
| WO | 03/106491 | 12/2003 |
| WO | 2004-022580 A2 | 3/2004 |
| WO | 2004-035793 A1 | 4/2004 |
| WO | 2004/037196 | 5/2004 |
| WO | 2004-045535 A2 | 6/2004 |
| WO | 2004-054501 A2 | 7/2004 |
| WO | 2004060318 A2 | 7/2004 |
| WO | 2004-070052 A2 | 8/2004 |
| WO | 2004-092339 A2 | 10/2004 |
| WO | 2005-084158 A2 | 9/2005 |
| WO | 2005-097116 A1 | 10/2005 |
| WO | 2006/001582 | 1/2006 |
| WO | 2006021458 A2 | 3/2006 |
| WO | 2006/050930 | 5/2006 |
| WO | 2007-031098 A1 | 3/2007 |
| WO | 2007/031280 | 3/2007 |
| WO | 2008-028860 A1 | 3/2008 |
| WO | 2008095943 A1 | 8/2008 |
| WO | 2008094208 A3 | 10/2008 |
| WO | 2009/137602 | 11/2009 |
| WO | 2009-143864 A1 | 12/2009 |
| WO | 2009-143865 A1 | 12/2009 |
| WO | 2009/144038 | 12/2009 |
| WO | 2009144037 A1 | 12/2009 |
| WO | 2010/065850 | 6/2010 |
| WO | 2011/160653 A1 | 12/2011 |
| WO | 2011/160827 A2 | 12/2011 |
| WO | 2012/048721 A1 | 4/2012 |
| WO | 2012/048893 A1 | 4/2012 |
| WO | 2013/091670 | 6/2013 |
| WO | 2013/091896 | 6/2013 |
| WO | 2014206426 A1 | 12/2014 |

OTHER PUBLICATIONS

Noguchi H. et al., Cell Permeable Peptide of JNK Inhibitor Prevents Islet Apoptosis Immediately After Isolation and Improves Islet Graft Function, American Journal of Transplantation, vol. 5, No. 8, pp. 1848-1855, Aug. 2005.

Noguchi H. et al., Effect of JNK Inhibitor During Islet Isolation and Transplantation, Transplantation proceedings, vol. 40, No. 2, pp. 379-381, Mar. 2008.

Sakane T. et al., Current Concepts: Behcet's disease, The New England Journal of Medicine, vol. 341, No. 17, pp. 1284-1291, Oct. 21, 1999.

Witkowski et al.—Conversion of a β-Ketoacyl Synthase to a Malonyl Decarboxylase by Replacement of the Active-Site Cysteine with Glutamine—Biochemistry—Aug. 18, 1999—pp. 11643-11650—vol. 38—American Chemical Society—USA.

Wyszko et al.—Interaction of Native RNAs with Tat Peptides—NATO Science Series, 3: High Technology 1999, 70 (RNA Biochemistry and Biotechnology), Sep. 9, 2002—pp. 277-290—Institute of Bioorganic Chemistry of the Polish Academy of Sciences, Poznan—Poland—Kluwer Academic Publishers—Chemical Abstracts Database Accession No. 133:204452 CA—13 XP002554007—Poland.

Yamamoto et al.—Molecular Design of Bioconjugated Cell Adhesian Peptide with a Water-Soluble Polymeric Modifer for Enhancement of Antimetastatic Effect—Current Drug Targets—2002—pp. 123-130—vol. 3—Bentham Science Publishers Ltd.—USA.

Yang et al.—Differential Targeting of MAP Kinases to the ETS-Domain Transcription Factor Elk-1—The EMBO Journal—1998—pp. 1740-1749—vol. 17—No. 6—European Molecular Biology Organisation—Oxford University Press —United Kingdom.

Yasuda et al.—The JIP Group of Mitogen-Activated Protein Kinase Scaffold Proteins —Molecular and Cellular Biology—Oct. 1999—pp. 7245-7254—vol. 19 —No. 10—American Society for Microbiology—USA.

(56) References Cited

OTHER PUBLICATIONS

Zhang et al.—Preparation of Functionally Active Cell-Permeable Peptides by Single-Step Ligation of Two Peptide Modules—Proceedings of National Academy of Sciences—Biochemistry—Aug. 1998—pp. 9184-9189—vol. 95—National Academy of Sciences—USA.
Zoukhri et al.—c-Jun NH2-Terminal Kinase Mediates Interleukin-1 β-Induced Inhibition of Lacrimal Gland Secretion—Journal of Neurochemistry—2006—pp. 126-135—vol. 96—International Society for Neurochemistry—USA.
NCBI Sequence Viewer—Accession No. AAD20443—Reports—Islet-Brain 1 (*Homo sapiens*)—Two References—Mooser et al.—Mar. 17, 1999—2 pages—USA.
NCBI Sequence Viewer—Accession No. AAD22543—Reports—Islet-Brain 1 (Rattus Norvegicus)—Three References—Bonny et al.—Mar. 1, 2006—2 pages—USA.
NCBI Sequence Viewer—Accession No. AAF32323—Reports—Islet-Brain 2 (*Homo sapiens*)—Two References—Negri et al.—Feb. 9, 2000—2 pages—USA.
NCBI Sequence Viewer—Accession No. AF074091—Reports—*Homo sapiens*Islet-Brain 1 mRNA—Complete Cds.—Two References—Mooser et al.—Mar. 17, 1999—2 pages—USA.
NCBI Sequence Viewer—Accession No. AF108959—Reports—Rattus Norvegicus Islet-Brain 1 (IB1) mRNA—Complete Cds.—Three References—Bonny et al.—Mar. 1, 2006—2 pages—USA.
NCBI Sequence Viewer—Accession No. AF218778—Reports—*Homo sapiens* Islet-Brain 2 mRNA—Complete Cds—Three References—Kristensen et al.—Mar. 2, 2006—2 pages—USA.
NCBI Sequence Viewer—Accession No. PH0878—Reports—Ig Kappa Chain V Region (Anti-DNA, SNA)—Human (Fragment ) One Reference—Manheimer-Lory et al.—May 30, 1997—1 page—USA.
Ahmed, Shafiq Uddin and Milner, Jo—Basal Cancer Cell Survival Involves JNK2 Suppression of a Novel JNK1/c-Jun/Bcl-3 Apoptotic Network—PLoS ONE—Oct. 2009—pp. 1-13—vol. 4—Issue 10—University of York—United Kingdom.
Bowie et al., "Deciphering the message in protein sequences: tolerance to amino acid substitutions," Science, 247 (4948): 1306-1310 (1990).
Database WPI, Thompson Scientific, Accession No. 2010-M79716, 2010, 3 pages; XP002643212.
Ferrandi et al., "Inhibition of c-Jun N-terminal kinase decreases cardiomyocyte apoptosis and infarct size after myocardial ischemia and reperfusion in anaesthetized rats," British Journal of Pharmacology, 142(6): 953-960 (2004).
Hirt et al., "D-JNKI1, a cell-penetrating c-Jun-N-terminal kinase inhibitor, protects against cell death in severe cerebral ischemia," Stroke, 35(7): 1738-1743 (2004).
Kugler et al., "MAP kinase pathways involved in glioblastoma response to erucylphosphocholine," International Journal of Oncology, 25(6):1721-1727 (2004).
Stedman's Online Dictionary Definition of "inflammation", Obtained from www.pdrel.com, last viewed on Dec. 18, 2010, 2 pages.
Wang et al., "A single amino acid determines lysophospholipid specificity of the S1P1 (EDG1) and LPA1 (EDG2) phospholipid growth factor receptors," Journal of Biological Chemistry, 276(52): 49213-49220 (2001).
Wells, "Additivity of mutational effects in proteins," Biochemistry, 29(37): 8509-8517 (1990).
Tan et al., "Selective inhibition of ErbB2-overexpressing breast cancer in vivo by a novel TAT-based ErbB2-targeting signal transducers and activators of transcription 3-blocking peptide," Cancer Res. 66:3764-3772, 2008.
De Paiva et al., "Essential role for c-Jun N-terminal kinase 2 in corneal epithelial response to desiccating stress," Arch Ophthalmol., 127(12): 1625-1631, 2009.
Ahmed et al., "Basal cancer cell survival involves JNK2 suppression of a novel JNK1/c-Jun/Bcl-3 apoptotic network," PLOS ONE 4(10): e7305 (2009).

Asanuma et al., "Protection against malonate-induced ischemic brain injury in rat by a cell-permeable peptidic c-Jun N-terminal kinase inhibitor, (L)-HIV-TAT48-57-PP-JBD20, observed by the apparent diffusion coefficient mapping magnetic resonance imaging method," Neurosci Lett., 359(1-2):57-60 (2004) (only abstract).
Bost et al., "The Jun kinase 2 isoform is preferentially required for epidermal growth factor-induced transformation of human A549 lung carcinoma cells," Molecular and Cellular Biology, 19(3): 1938-1949 (1999).
Chang Lufen et al., JNK1 is required for maintenance of neuronal microtubules and controls phosphorylation of microtubule-associated proteins, Developmental Cell, 4(4): 521-533 (2003).
Hunot Stephan et al., "JNK-mediated induction of cyclooxygenase 2 is required for neurodegeneration in a mouse model of Parkinson's disease," Proceedings of the National Academy of Sciences of the United States of America,101 (2): 665-670 (2004).
Kaneto et al., "Possible novel therapy for diabetes with cell-permeable JNK-inhibitory peptide," Nature Medicine, 10 (10):1128-1132 (2004).
Kuan et al., "A critical role of neural-specific JNK3 for ischemic apoptosis," Proceedings of the National Academy of Sciences of the United States of America, 100(25): 15184-15189 (2003).
Polyakov et al., "Novel Tat-peptide chelates for direct transduction of technetium-99m and rhenium into human cells for imaging and radiotherapy" Bioconjugate Chem., 11: 762-771 (2000).
Saar et al., "Cell-penetrating peptides: a comparative membrane toxicity study," Analytical Biochemistry, 345(1):55-65 (2005).
Sabapathy, "Role of the JNK pathway in human diseases," Progress in Molecular Biology and Translational Science, 106:145-169 (2012).
Salh, "c-Jun N-terminal kinases as potential therapeutic targets," Expert Opin Ther Targets, 11(10):1339-1353 (2007).
Seki et al., "A liver full of JNK: signaling in regulation of cell function and disease pathogenesis, and clinical approaches," Gastroenterology, 143(2):307-320 (2012).
Sumara et al., "Jnking atherosclerosis," Cellular and Molecular Life Sciences, Birkhäuser Verlag, 62(21): 2487-2494 (2005).
Tachibana et al., "JNK1 is required to preserve cardiac function in the early response to pressure overload, Biochemical and Biophysical Research Communications," 343(4): 1060-1066 (2006).
Westwick et al., "Activatin of Jun kinase is an early event in hepatic regeneration," The Journal of the Clinical Investigation, 95(2): 803-810 (1995).
Hommes et al., "Inhibition of stress-activated MAP kinases induces clinical improvement in moderate to severe Crohn's disease," Gastroenterology, 122(1):7-14 (2002).
Mitsuyama et al., "Pro-inflammatory signaling by Jun-N-terminal kinase in inflammatory bowel disease," Int J Mol Med., 17(3):449-55 (2006).
Qin et al., "TAT Protein Transduction Domains : New Promise for Protein Therapy," Chinese Journal of Biochemistry and Molecular Biology, 23(7): 519-524 (2007) (Abstract Translated).
Parenteau et al., "Free uptake of cell-penetrating peptides by fission yeast," FEBS Letters, 579: 4873-4878 (2005).
Patel et al., "Getting into the brain—approaches to enhance brain drug delivery," CNS Drugs, 23(1): 35-58 (2009).
Nori, Aparna and Kopecek, Jindrich—Intracellular Targeting of Polymer-Bound Drugs for Cancer Chemotherapy—Advanced Drug Delivery Reviews—Dec. 24, 2004—pp. 609-636—vol. 57—ScienceDirect—Elsevier B.V.—The Netherlands.
Okitsu et al. - Protein Transduction Domains Enable Isolated Islets to Efficiently Internalize the Target Protein—Transplantation Proceedings—Feb. 2003—p. 479—vol. 35—Elsevier Science inc.—USA.
Pan et al.—Small Peptide Inhibitor of JNKs Protects Against MPTP-Induced Nigral Dopaminergic Injury via Inhibiting the JNK-SIgnaling Pathway—Laboratory Investigation—Feb. 2010—pp. 156-167—vol. 90—USCAP, Inc.—USA.
Parkinson's Disease: Challenges, Progress, and Promise—Publication—National Institute of Neurological Disorders and Stroke—National Institutes of Health—2004—22 pages—No. 05-5595—<http://www.ninds.nih.gov/disorders/parkinsons_disease/parkinsons_research_pr.htm.

(56) References Cited

OTHER PUBLICATIONS

Penco et ai.—Identification of an Import Signal for, and the Nuclear Localization of, Human Lactoferrin—Biotechnology and Applied Biochemistry—Dec. 2001—pp. 151-159—vol. 34—Portland Press Ltd—United Kingdom.

Pennington, Michael W. and Dunn, Ben M. (Editors)—Chapter 11—Design of Novel Synthetic Peptides including Cyclic Conformationally and Topgraphically Constrained Analogs—HRUBY, Victor and Bonner, G. Gregg—Methods in Molecular Biology—vol. 35—Peptide Synthesis Protocols—1994—pp. 201-239—Humana Press Inc.—USA.

Pennington, Michael W. and Dunn, Ben M. (Editors)—Chapter 12—Solid-Phase Synthesis of Peptides Containing the CH2NH Reduced Bond Surrogate—Pennington, Michael W.—Methods in Molecular Biology—vol. 35—Peptide Synthesis Protocols—1994—pp. 241-247—Humana Press Inc.—USA.

Pratner et al.—Synthesis and Characterization of a Gd-DOTA-D-Permeation Peptide for Magnetic Resonance Relaxation Enhancement of Intracellular Targets—Research Article—Massachusetts Institute of Technology—Molecular Imaging—Oct. 2003—pp. 333-341—vol. 2—No. 4—The Society of Molecular Imaging—USA.

Ramage, Robert and Epton, Roger (Editors)—Chapters 165 and 166—Guichard et al.—Chapter 167—Gur'Yanov et al.—EPS—Proceedings of the Twenty-Fourth European Peptide Symposium, Sep. 8-13, 1996, Edinburgh, Scotland—pp. 447-451—The European Peptide Society—Mayflower Scientific Ltd.—United Kingdom.

Ramage, Robert and Epton, Roger (Editors)—Chapter—183—Horvath et al.—Chapter 184—Hruby et al.—EPS—Proceedings of the Twenty-Fourth European Peptide Symposium, Sep. 8-13, 1996, Edinburgh, Scotland—pp. 483-486—The European Peptide Society—Mayflower Scientific Ltd.—United Kingdom.

Ramanathan et al.—Targeting the Sodium-Dpendent Multivitamin Transporter (SMVT) for Improving the Oral Absorption Properties of a Retro-Inverso Tat Nonapeptide—Pharmaceutical Research—Jul. 2001—pp. 950-956—vol. 18—No. 7—USA.

Ribeiro et al.—Heme Oxygenase-1 Fused to a TAT Peptide Transduces and Protects Pancreatic β-Cells—BBRC—Biochemical and Biophysical Research Communications—Apr. 4, 2003—pp. 876-881—vol. 305—ScvienceDirect—Academic Press—Elesevier Science (USA)—USA.

Rickels et al.—Phage Display Selection of Ligand Residues Important for Src Homology 3 Domain Binding Specificity—Biochemistry—Proceedings of the National Academy of Science—Nov. 1995—pp. 10909-10913—vol. 92—National Academy of Science—USA.

Robinson et al.—Properties and Structure-Activity Studies of Cyclic β-hairpin Peptidomimetics Based on the Cationic Antimicrobial Peptide Protegrin I—Bioorganic & Medicinal Chemistry—Jan. 7, 2005—pp. 2055-2064—vol. 13—ScienceDirect—Elsevier Ltd.—USA.

Roduit, Raphael and Schorderet, Daniel F.—MAP Kinase Pathways in UV-Induced Apoptosis of Retinal Pigment—Epithelium ARPE19 Cells—Apoptosis—2008—pp. 343-353—DOI 10.1007/s10495-008-0179-8—Springer Science+Business Media, LLC—USA.

Rojas et al.—Controlling Epidermal Growth Factor (EGF)-Stimulated Ras Activation in Intact Cells by a Cell-Permeable Peptide Mimicking Phosphorylated EGF Receptor—Journal of Biological Chemistry—Nov. 1, 1996—pp. 27456-27461—vol. 271—No. 44—The American Society for Biochemistry and Molecular Biology, Inc.—USA.

Roy et al.—Role of the JNK Signal Transduction Pathway in Inflammatory Bowel Disease—World Journal of Gastroenterol—Jan. 14, 2008—pp. 200-202—vol. 14—No. 2—www.wjgnet.com—USA.

Ruben et al.—Structural and Functional Characterization of Human Immunodeficiency Virus tat Protein—Journal of Virology—Jan. 1989—pp. 1-8—vol. 63—No. 1—American Society for Microbiology—USA.

Rudikoff et al.—Single Amino Acid Substitution Altering Antigen-Binding Specificity—Immunology—Proceedings of the National Academy of Science—Mar. 1982—pp. 1979-1983—vol. 79—National Academy of Science—USA.

Rudinger, J.—Characteristics of the Amino Acids as Components of a Peptide Hormone Sequence—Peptide Hormones—1976—pp. 1-7—University Park Press, Baltimore—USA.

Saito, Naoyuki G. and Paterson, Yvonne—Contribution of Peptide Backbone Atoms to Binding of an Antigenic Peptide to Class 1 Major Histocompatibility Complex Module—Molecular Immunology—Nov. 13, 1997—pp. 1133-1145—vol. 34—Nos. 16-17—Pergamon—Elsevier Science Ltd.—United Kingdom.

Schimmer et al—The BH3 Domain of BAD Fused to the Antennapedia Peptide Induces Apoptosis via its Alpha Helical Structure and Independent of Bcl-2—Cell Death and Differentiation—Feb. 18, 2001 pp. 725-733—vol. 8—No. 7—Canada.

Schinzel, R. and Drueckes, P.—The Phosphate Recognition Site of *Escherichia Coli* Maltodextrin Phosphorylase—FEBS Letters—Jul. 29, 1991—pp. 125-128—vol. 286—Nos. 1 and 2—Federation of European Biochemical Societies—Elsevier Science Publishers B.V.—The Netherlands.

Schwarze et al.—In Vivo Protein Transduction: Delivery of a Biologically Active Protein into the Mouse—Science—Sep. 3, 1999—pp. 1569-1572—vol. 285—Science Magazine—USA.

Sebestyen et al.—DNA Vector Chemistry: The Covalent Attachment of Signal Peptides to Plasmid DNA—Research—Nature Biotechnology—Jan. 16, 1998—pp. 80-85—vol. 16—USA.

Selective Dimerisation of Cysteines to form Heterodimers—Aim—Chemistry—Procedure—NJE—Feb. 3, 1997—One Page—USA.

Smilek et al.—A Single Amino Acid Change in a Myelin Basic Protein Peptide Confers the Capacity to Prevent Rather than Induce Experimental Autoimmune Encephalomyelitis—Immunology—Proceedings of the National Academy of Science—Nov. 1, 1991—pp. 9633-9637—vol. 88—No. 21—The National Academy of Science—USA.

Stevens et al.—Efficient Generation of Major Histocompatibility Complex Class I-Peptide Complexes Using Synthetic Peptide Libraries—The Journal of Biological Chemistry—Jan. 3, 1998—pp. 2874-2884—vol. 273—No. 5—The American Society for Biochemistry and Molecular Biology, Inc.—USA.

Fischer, P.M.—The Design, Synthesis and Application of Stereochemical and Directional Peptide Isomers: A Critical Review—Current Protein and Peptide Science—2003—pp. 339-356—vol. 4—Bentham Science Publishes Ltd.—United Kingdom.

Thoren et al.—The Antennapedia Peptide Penetratin Translocates across Lipid Bilayers—The First Direct Observation—FEBS Letters—2000—pp. 265-268—No. 482—Federation of European Biochemical Societies—Elsevier Science B.V.—Europe.

Torchilin et al.—Fluorescence Microscopy to Follow the Targeting of Liposomes and Micelles to Cells and their Intracellular Fate—Advanced Drug Delivery Reviews—Jan. 2005—pp. 95-109—vol. 57—ScienceDirect Elsevier B.V.—The Netherlands.

Torgerson et al.—Regulation of NF-kappa B, AP-1, NFAT, and STAT1 Nuclear Import in T Lymphocytes by Noninvasive Delivery of Peptide Carrying the Nuclear Localization Sequence of NF-kappa B p50—Journal of Immunology—1998—pp. 6084-6092—vol. 161—The American Association of Immunologists—USA.

Touchard et al.—A Peptide Inhibitor of c-Jun N-Terminal Kinase for the Treatment of Endotoxin-Induced Uveitis—Immunology and Microbiology—Investigative Ophthalmology & Visual Science—Sep. 2010—pp. 4683-4693—vol. 51—No. 9—Association for Research in Vision and Ophthalmology—USA.

Tournier et al.—Mitogen-Activated Protein Kinase Kinase 7 is an Activator of the c-Jun NH2-Terminal Kinase—Cell Biology—Proceedings of the National Academy of Science—Jul. 1997—pp. 7337-7342—vol. 94—National Academy of Science—USA.

Van Regenmortel et al.—D-Peptides as Immunogens and Diagnostic Reagents—Protein Engineering—Current Opinion of Biotechnology—1998—pp. 377-382—vol. 8—Current Biology Publications—France.

Vives et al.—A Truncated HIV-1 Tat Protein Basic Domain Rapidly Translocates Through the Plasma Membrane and Accumulates in the Cell Nucleus—Journal of Biological Chemistry—Jun. 20, 1997—pp. 16010-16017—vol. 272—No. 25—The American Society for Biochemistry and Molecular Biology, Inc.—USA.

(56) References Cited

OTHER PUBLICATIONS

Vives et al.—Structure-Activity Relationship Study of the Plasma Membrane Translocating Potential of a Short Peptide from HIV-1 Tat Protein—Letters in Peptide Science—1997—pp. 429-436—vol. 4—Kluwer Academic Publishers—The Netherlands.

Vocero-Akbani et al.—Killing HIV-Infected Cells by Transduction with an HIV Protease-Activated Caspase-3 Protein—Nature Medicine—Jan. 1999—pp. 29-33—vol. 5—No. 1—Nature America Inc.—USA.

Voet, Donald and Voet, Judith G.—Abnormal Hemoglobins—1995—pp. 235-241—Biochemistry Second Edition—John Wiley & Sons, Inc.—USA.

Wadia et al.—Delivery of Novel Anti-Cancer Peptides by Protein Transduction Domains—Peptides—May 2004—pp. 65-69—American Pharmaceutical Review—USA.

Waldmeier et al.—Recent Clinical Failures in Parkinson's Disease with Apoptosis Inhibitors Underline the Need for a Paradigm Shift in Drug Discovery for Neurodegenerative Diseases—Biochemical Pharmacology—Nov. 15, 2006—pp. 1197-1206—vol. 72—No. 10—ScienceDirect—Elsevier Inc.—USA.

Walsh et al.—Erythrocyte Survival is Promoted by Plasma and Suppressed by a Bak-Derived BH3 Peptide that Interacts with Membrane-Associated Bcl-XL—Red Cells—Blood—May 1, 2002 pp. 3439-3448 —vol. 99—No. 9—The American Society of Hematology—USA.

Wender et al.—The Design, Synthesis, and Evaluation of Molecules that Enable or Enhance Cellular Uptake: Peptoid Molecular Transporters—Proceedings of the National Academy of Science—Nov. 21, 2000—pp. 13003-13008—vol. 97—No. 24—The National Academy of Science—USA.

Whitmarsh et al.—A Mammalian Scaffold Complex that Selectively Mediates MAP Kinase Activation—Science—Sep. 11, 1998—pp. 1671-1674—vol. 281-5383 —www.sciencemag.org—USA.

Whitmarsh, A.J. and Davis, R.J.—Transcription Factor AP-1 Regulation by Mitogen-Activated Protein Kinase Signal Transduction Pathways—Review—Journal of Molecular Medicine Oct. 7, 1996—pp. 589-607—vol. 74—No. 1—Springer-Verlag—USA.

Wilson, David—Preventing Nerve Cell Death in ALS—Internet document—<http://www.als.caJ_news/57.aspx>—Dec. 5, 2001—2 pages—USA.

Wishart et al.—A Single Mutation Converts a Novel Phosphotyrosine Binding Domain into a Dual-specificity Phosphatase—Communication—The Journal of Biological Chemistry—Nov. 10, 1995—pp. 26782-26785—vol. 270—No. 45—The American Society for Biochemistry and Molecular Biology, Inc.—USA.

Adele-Biassette et al.—Neuronal Apoptosis does not Correlate with Dementia in HIV Infection but is Related to Microglial Activation and Axonal Damage—Neuropathology and Applied Neurobiology—1999—pp. 123-133—vol. 25—Blackwell Science Ltd.—USA.

Adler, et al.—Regulation of JNK Signaling by GSTp—The EMBO Journal—Mar. 1, 1999—pp. 1321-1334—vol. 18—No. 5—European Molecular Biology Organization—USA.

Brady, Leo and Dodson, Guy—Reflections on a Peptide—Nature—News and Views—Drug Design—Apr. 21, 1004—pp. 692-693—vol. 368 (6473)—Nature Publishing Group—USA.

Briand et al—A Retro-Inverso Peptide Corresponding to the GH Loop of Foot-and-Mouth Disease Virus Elicits High Levels of Long-Lasting Protective Neutralizing Antibodies—Proceedings of National Academy of Sciences—Immunology—Nov. 1997—pp. 12545-12550—vol. 94—National Academy of Sciences—USA.

Brugidou et al.—The Retro-Inverso Form of a Homeobox-Derived Short Peptide is Rapidly Internalized by Cultured Neurons: A New Basis for an Efficient Intracellular Delivery System—Biochemical and Biophysical Research Communications—Sep. 14, 1995—pp. 685-693—vol. 214—No. 2—Academic Press, Inc.—USA.

Chie et al.—Identification of the Site of Inhibition of Oncogenic ras-p21-Induced Signal Transduction by a Peptide from a Ras Effector Domain—Journal of Protein Chemistry—Nov. 4, 1999—pp. 881-884—vol. 18—No. 8—USA.

Chorev et al.—A Dozen Years of Retro-Inverso Peptidomimetics—Accounts of Chemical Research—1993—pp. 226-273—vol. 26—American Chemical Society—USA.

Chorev et al.—Recent Developments in Retro Peptides and Proteins—An Ongoing Topochemical Exploration—Oct. 1995—pp. 438-445—vol. 13—No. 10—TIBTECH (Trends in Biotechnology) Elsevier Science Ltd.—USA.

Dang et al.—Nuclear and Nucleolar Targeting Sequences of c-erb-A, c-myb, N-myc, p53, HSP70, and HIV tat Proteins—Journal of Biological Chemistry—Oct. 25, 1989—pp. 18019-18023—vol. 264—No. 30—The American Society for Biochemistry and Molecular Biology, Inc.—USA.

Duby et al. (Contributors)—Using Synthetic Oligonucleotides as Probes—Current Protocols in Molecular Biology—Supplement 2—Apr. 1988—pp. 6.4.1-6.4.10—John Wiley & Sons—Document No. XP 002044485—USA.

Elliott et al.—Intercellular Trafficking and Protein Delivery by a Herpesvirus Structural Protein—Cell—Jan. 24, 1997—pp. 223-233—vol. 88—No. 2—Cell Press—United Kingdom.

Frankel et al.—Activity of Synthetic Peptides from the Tat Protein of Human Immunodeficiency Virus Type 1—Proceedings of National Academy of Sciences—Biochemistry—Oct. 1989—pp. 7397-7401—vol. 86—National Academy of Sciences—USA.

Giorello et al—Inhibition of Cancer Cell Growth and c-Myc Transcriptional Activity by a c-Myc Helix 1-Type Peptide Fused to an Internalization Sequence—Cancer Research—Aug. 15, 1998—pp. 3654-3659—vol. 58—USA.

Guichard et al.—Partially Modified Retro-Inverso Pseudopeptides as Non-Natural Ligands for the Human Class I Histocompatibility Molecule HLA-A2—Journal of Medicinal Chemistry—1996—pp. 2030-2039—vol. 39—American Chemical Society—USA.

Hauber et al.—Mutational Analysis of the Conserved Basic Domain of Human Immunodeficiency Virus tat Protein—Journal of Virology—Mar. 1989—pp. 1181-1187—vol. 63—No. 3—American Society of Microbiology—USA.

Inhibit.Dictionary.com—The American Heritage® Stedman's Medical Dictionary—Houghton Mifflin Company—One Page—Internet document: http://dictionary.reference.com/browse/inhibit—Accessed on Oct. 10, 2007—USA.

Jackson et al.—Heat Shock Induces the Release of Fibroblast Growth Factor 1 from NIH 3T3 Cells—Proceedings of National Academy of Sciences—Cell Biology—Nov. 1992—pp. 10691-10695—vol. 89—National Academy of Sciences—USA.

Jameson et al.—A Rationally Designed CD4 Analogue Inhibits Experimental Allergic Encephalomyelitis—Nature—Letters to Nature —Apr. 21, 1994—pp. 744-746—vol. 368 Nature Publishing Group—USA.

Kennedy, Norman J. and Davis, Roger J.—Perspectives: Role of JNK in Tumor Development—Cell Cycle—May/Jun. 2003—pp. 199-201—vol. 2—No. 3—www.landesbioscience.com—USA.

Kida et al.—Design and Synthesis of a Tat-related Gene Transporter: A Tool for Carrying the Adenovirus Vector into Cells—Bioorganic and Medicinal Chemistry Letters—Dec. 6, 2005—pp. 743-745—vol. 16—ScienceDirect—Elsevier Ltd—USA.

Kieber-Emmons et al.—Therapeutic Peptides and Peptidomimetics—Current Opinion in Biotechnology—1997—pp. 435-441—vol. 8—Current Biology Ltd.—USA.

Kishan, K.V. Radha and Agrawal, Vishal—SH3-like Fold Proteins are Structurally Conserved and Functionally Divergent—Current Protein and Peptide Science—1995—pp. 143-150—vol. 6—Nentham Science Publishers Ltd.—USA.

Kisselev, Lev—Polypeptide Release Factors in Prokaryotes and Eukaryotes: Same Function, Different Structure—Jan. 2002—pp. 8-9—vol. 10—Structure—Elsevier Science Ltd—USA.

Lebleu, Bernard—Delivering Information-Rich Drugs—Prospects and Challenges—Meeting Report—Apr. 1996—pp. 109-110—vol. 14—No. 4—TIBTECH (Trends in Biotechnology) Elsevier Science Ltd.—USA.

(56) References Cited

OTHER PUBLICATIONS

Lee et al.—c-Jun N-terminal Kinasa (JNK) Mediates Feedback Inhibition of the Insulin Signaling Cascade—The Journal of Biological Chemistry—Jan. 31, 2003—pp. 2896-2902—vol. 278—No. 5—The American Society for Biochemistry and Molecular Biology, Inc.—USA.

Lewis et al.—Lymphoma Cell Uptake of Radiometal- and Fluorescent-Labelled BCL-2 Antisense PNA Conjugates is Mediated by a Retro-Inverso Delivery Peptide—Abstracts—Journal of Label Compounds and Radiopharmaceuticals—2003—p. S13—vol. 46—SI-S403—XP-002347557—USA.

Li, Shawn S.C.—Review Article—Specificity and Versatility of SH3 and Other Ptoline-Recognition Domains: Structural Basis and Implications for Cellular Signal Transduction—Biochemical Journal—Sep. 15, 2005—pp. 641-653—Biochemical Society—vol. 390—Part 3—United Kingdom.

Lim et al.—Penetration Enhancement in Mouse Skin and Lipolysis in Adipocytes by TAT-GKH, A New Cosmetic Ingredient—Journal of Cosmetic Science—Sep./Oct. 2003—pp. 483-491—vol. 54—USA.

Lin et al.—Inhibition of Nuclear Translocation of Transcription Factor NF-kappa B by a Synthetic Peptide Containing a Cell Membrane-Permeable Motif and Nuclear Localization Sequence—Journal of Biological Chemistry—Jun. 16, 1995—pp. 14255-14258—vol. 270—No. 24—The American Society for Biochemistry and Molecular Biology, Inc.—USA.

Lloyd-Williams et al.—Chapter 5—Chemical Approaches to the Synthesis of Peptides and Proteins—1997—Formation of Disulfide Bridges—pp. 209-236—CRC Press LLC—USA.

Lloyd-Williams et al.—Chapter 6—Chemical Approaches to the Synthesis of Peptides and Proteins—1997—Peptide Libraries—pp. 237 and 264-267—CRC Press LLC—USA.

Mann, David A. and Frankel, Alan D.—Endocytosis and Targeting of Exogenous HIV-1 Tat Protein—The EMBO Journal—1991—pp. 1733-1739—vol. 10—No. 7—Oxford University Press—United Kingdom.

Marino et al.—Inhibition of Experimental Autoimmune Encephalomyelitis in SJL Mice by Oral Administration of Retro-Inverso Derivative of Encephalitogenic Epitope P87-99—European Journal of Immunology—1999—pp. 2560-2566—vol. 29—Wiley-VCH Verlag GmbH—Weinheim—Germany.

Marks et al.—Protein Targeting by Tyrosine- and Di-leucine-based Signals: Evidence for Distinct Saturable.Components—The Journal of Cell Biology—Oct. 1, 1996—pp. 341-354—vol. 135—No. 2—The Rockefeller University Press—USA.

Mayer, Bruce J.—SH3 Domains: Complexity in Moderation—Commentary—Journal of Cell Science—Signal Transduction and Cellular Organization—Apr. 2001—pp. 1253-1263—vol. 114—The Company of Biologists Ltd.—USA.

Mazur, Dan J. and Perrino Fred W.—Indetificatoin and Expression of the TREX1 and TREX2 cDNA Sequences Encoding Mammalian 3'→5' Exonucleases—The Journal of Biological Chemistry—Jul. 9, 1999—pp. 19655-19660—vol. 274—No. 28—The American Society for Biochemistry and Molecular Biology, Inc.—USA.

Melikov, K. and Chernomordik, L.V.—Review—Arginine-rich Cell Penetrating Peptides: From Endosomal Uptake to Nuclear Delivery—Cellular and Molecular Life Sciences—Oct. 18, 2005—pp. 2739-2749—vol. 62—Birkhauser Verlag—Switzerland.

Messer, Jr., Dr. William S.—MBC 3320 Posterier Pituitary Hormones—Vasopression and Oxytocin—Apr. 3, 2000—pp. 1-5—,http://www.neurosci.pharm.utoledo.edu/MBC3320/vasopressin.htm>—USA.

Mi et al.—Characterization of a Class of Cationic Peptides able to Facilitate Efficient Protein Transduction in Vitro and in Vivo—Article—Molecular Therapy—Oct. 2000—pp. 339-347—vol. 2—No. 4—The American Society of Gene Therapy—USA.

Milano et al.—A peptide Inhibitor of c-Jun NM2-terminal Kinase Reduces Myocardial Ischemia-reperfusion Injury and Infarct Size in Vivo—American Journal of Physiology—Heart Circulation Physiology—Apr. 2007—pp. H1828-H1835—vol. 292—www.ajpheart.org—The American Physiological Society—USA.

Mooi et al.—Regulation and Structure of an *Escherichia coli* Gene Coding for an Outer Membrane Protein involved in Export of K88ab Fimbrial Subunits—Nucleic Acids Research—1996—pp. 2443-2457—vol. 14—No. 6—IRL Press Linited—United Kingdom.

Moon et al. Bcl-2 Overexpression Attenuates SP600125-induced Apoptosis in Human Leukemia U937 Cells—Cancer Letters—Feb. 3, 2008—pp. 316-325—vol. 264—ScienceDirect—Elsevier Ireland Ltd—Ireland.

Mooser et al.—Genomic Organization, Fine-Mapping, and Expression of the Human Islet-Brain 1 (IB1)/C-Jun-Amino-Terminal Kinase Interacting Protein-1 (JIP-1) Gene—Genomics—Jan. 15, 1999—pp. 202-208—vol. 55—Academic Press—USA.

Moulin, Nathalie and Widman, Christian—Islet-Brain (IB)/JNK-Interacting Proteins (JIPs): Future Targets for the Treatment of Neurodegenerative Diseases?—Current Neurovascular Research—2004—pp. 111-127—vol. 1—No. 2—Institut de Biologie Cellulaire et de Morphologie (IBCM)—Université de Lusanne—Switzerland—Bentham Science Publishers Ltd.—USA.

Nagahara et al.—Transduction of Full-Length TAT Fusion Proteins into Mammalian Cells: TAT-p27Kip1 Induces Cell Migration—Nature Medicine—Dec. 1998—pp. 1449-1452—vol. 4—No. 12—Nature America Inc.—USA.

Negri at al.—Design of a Novel Peptide Inhibitor of the JNK Signaling Pathway—1217-P—Journal—Diabetes—Abstract Book—61st Scientific Session—Jun. 2001—p. A294—vol. 50—Supplement No. 2—American Diabetes Association—USA.

Neundorf et al.—Detailed Analysis Concerning the Biodistribution and Metabolism of Human Calcitonin-Derived Cell-Penetrating Peptides—Bioconjugate Chemistry—Jul. 24, 2008—pp. 1596-1603—vol. 19—No. 8—American Chemical Society—USA.

Ngo et al.—Computational Complexity, Protein Structure Prediction, and the Levinthal Paradox—The Protein Folding.Problem and Tertiary Structure Prediction—Merz et al. (Editors)—1994—pp. 433, 492-495—Birkhauser Boston—USA.

Noguchi et al.—Regulation of c-Myc through Phosphorylation at Ser-62 and Ser-71 by c-Jun N-Terminal Kinase—Journal of Biological Chemistry—Nov. 12, 1999—pp. 32580-32587—vol. 274—No. 46—The American Society for Biochemistry and Molecular Biology, Inc.—USA.

Nori et ai.—Tat-Conjugated Synthetic Macromolecules Facilitate Cytoplasmic Drug Delivery to Human Ovarian Carcinoma Cells—Bioconjugate Chemistry—Nov. 16, 2002—pp. 44-50—vol. 14—No. 1—American Chemical Society—USA.

Aarts et al.—Treatment of Ischemic Brain Damage by Perturbing NMDA Receptor—PSD-95 Protein Interactions—Science—Oct. 25, 2002—pp. 846-850—vol. 298—www.sciencemag.org—USA.

Abaza et al.—Effects of Amino Acid Substitutions Outside an Antigenic Site on Protein Binding to Monoclonal Antibodies of Predetermined Specificity Obtained by Peptide Immunization: Demonstration with Region 94-100 (Antigenic Site 3) of Myoglobin—Journal of Protein Chemistry—1992—pp. 433-444—vol. 11—No. 5—USA.

Agrawal, Vishal and Kishan, K.V. Radha—Promiscuous Binding Nature of SH3 Domains to their Target Proteins—Protein and Peptide Letters—2002—pp. 185-193—vol. 9—No. 3—Bentham Science Publishers Ltd.—USA.

Aldrian-Herrada et al.—A Peptide Nucleic Acid (PNA) is More Rapidly Internalized in Cultured Neurons when Coupled to a Retro-Inverso Delivery Peptide. The Antisense Activity Depresses the Target mRNA and Protein in Magnocellular Oxytocin Neurons—Nucleic Acids Research—1998—pp. 4910-4916—vol. 26—No. 21—Oxford University Press—UK.

Assi et al.—The Specific JNK Inhibitor SP600125 Targets Tumour Necrosis Factor-α Production and Epithelial Cell Apoptosis in Acute Murine Colitis—Immunology—2006—pp. 112-121—Blackwell Publishing Ltd.—USA.

Barr et al.—Identification of the Critical Features of a Small Peptide Inhibitor of JNK Activity—Mar. 20, 2002—pp. 10987-10997—vol. 277—No. 13—USA.

Berendsen, Herman J.C.—A Glimpse of the Holy Grail?—Oct. 23, 1998—pp. 642-643—vol. 282—No. 5389—Science—Research Library—USA.

(56) References Cited

OTHER PUBLICATIONS

Bessalle et al.—All-D-Magainin: Chirality, Antimicrobial Activity and Proteolytic Resistance—FEBS Letters—Nov. 12, 1990—pp. 151-155—vol. 274—Nos. 1/2—Federation of European Biochemical Societies—Elsevier Science Publishes B.V.—The Netherlands.
Bonny et al.,—Cell-Permeable Peptide Inhibitors of JNK: Novel Blockers of Beta-Cell Death—Diabetes—Jan. 2001—pp. 77-82—vol. 50—No. 1—USA.
Bonny et al.—IB1, A JIP-1-Related Nuclear Protein Present in Insulin-Secreting Cells—Journal of Biological Chemistry—Jan. 23, 1998—pp. 1843-1846—vol. 273—No. 4—USA.
Bonny et al.—Pancreatic-Specific Expression of the Glucose Transporter Type 2 Gene: Identification of cis-Elements and Islet-Specific trans-Acting Factors—MOL ENDO—Molecular Endocrinology—1995—pp. 1413-1426—vol. 9—No. 10—The Endocrine Society—USA.
Bonny et al.—Targeting the JNK Pathway as a Therapeutic Protective Strategy for Nervous Systems Diseases—2005—pp. 57-67—vol. 16—No. 1—Freund & Pettman—United Kingdom.
Borsello et al.—A Peptide Inhibitor of c-Jun N-Terminal Kinase Protects Against Excitotoxicity and Cerebral Ischemia—Aug. 24, 2003 (Sep. 2003)—pp. 1180-1186—vol. 9—No. 9—Nature Medicine—USA.
Borsello, Tiziana and Bonny, Christophe—Use of Cell-Permeable Peptides to Prevent Neuronal Degeneration—Trends in Molecular Medicine—May 2004—pp. 239-244—vol. 10—No. 5—Elsevier Ltd—www.sciencedirect.com—USA.
Bradley, Christina Marchette and Barrick, Doug—Limits of Cooperativity in a Structurally Modular Protein: Response of the Notch Ankyrin Dpmaon to Analogous Alanine Substitutions in Each Repeat—JMB—Journal of Molecular Biology—Nov. 22, 2002—pp. 373-386—vol. 324—USA.
Branden et al.—A Peptide Nucleic Acid-Nuclear Localization Signal Fusion that Mediates Nuclear Transport of DNA—Nature Biotechnology—Aug. 1999—pp. 784-787—vol. 17—Nature America Inc.—USA.
Branden, Carl and Tooze, Carl—Introduction to Protein—Second Edition—1999—Garland Publishing, Inc.—p. 382—USA.
Branden, Carl and Tooze, Carl—Introduction to Protein—1991—Garland Publishing, Inc.—p. 247—USA.
Cardozo et al.—Cell-Permeable Peptides Induce Dose- and Length-Dependent Cytotoxic Effects—Biochimica et Biophysica Acta—Jun. 14, 2007—pp. 2222-2234—No. 1768—ScienceDirect—Elsevier B.V.—The Netherlands.
Chaloin et al.—Design of Carrier Peptide-Oligonucleotide Conjugates with Rapid Membrane Translocation and Nuclear Localization Properties—Biochemical and Biophysical Research Communications—Article No. RC978050—1998—pp. 601-608—vol. 243—No. 2—Academic Press—Elsevier B.V.—The Nethlands.
Creighton, Thomas E. (Editor)—Janin, Jaël—Protein—Protein Interactions—Encyclopedia of Molecular Biology—1999—pp. 2027-2033—vol. 1—A Wiley-Interscience Publication—John Wiley & Sons, Inc.—USA.
Derossi et al.—Cell Internalization of the Third Helix of the Antennapedia Homeodomain Is Receptor-independent—The Journal of Biological Chemistry—Jul. 26, 1996—pp. 18188-18193—vol. 271—No. 30—The American Society for Biochemistry and Molecular Biology, Inc.—USA.
Designing Custom Peptides—Sigma Genosys—Technical Bulletin—Dec. 16, 2004—2 pages—<http://www.sigma-genosys.com/peptide_design.asp>—USA.
Dickens et al.—Database—Uniprot—Retrieved from EBI—Database Accession No. Q9WVI9—Abstracts—Feb. 28, 2003—Document No. XP-002366175—USA.
Dickens et al.—A Cytoplasmic Inhibitor of the JNK Signal Transduction Pathway—Science—Aug. 1, 1997—pp. 693-696—vol. 277—No. 5326—Science Magazine—USA.
Dietz, Gunner P.H. and Bahr, Mathias—Review—Delivery of Bioactive Molecules into the Cell: The Trojan Horse Approach—Molecular and Cellular Neuroscience—2004—pp. 85-131—vol. 27—Elsevier Inc.—The Netherlands.
Dominguez-Bendala et al.—TAT-Mediated Neurogenin 3 Protein Transduction Stimulates Pancreatic Endocrine Differentiation in Vitro—Diabetes—Mar. 2005—pp. 720-726—vol. 54—The American Diabetes Association—USA.
Fawell et al.—Tat-Mediated Delivery of Heterologous Proteins into Cells—Cell Biology—Proceedings of the National Academy of Sciences—Jan. 8, 1994—pp. 664-668—vol. 9—Biogen Inc.—USA.
Fornoni et al.—The L-Isoform but not D-Isoforms of a JNK Inhibitory Peptide Protects Pancreatic β-cells—Biochemical and Biophysical Research Communications—Jan. 2, 2007—pp. 227-233—vol. 354—ScienceDirect—Elsevier Inc.—USA.
Frankel, Alan D. and Pabo, Carl O.—Cellular Uptake of the Tat Protein from Human Immunodeficiency Virus—Cell—Dec. 23, 1988—pp. 1189-1193—vol. 55—Cell Press—USA.
Futaki et al.—Arginine-rich Peptides—An Abundant Source of Membrane-Permeable Peptides Having Potential as Carriers for Intracellular Protein Delivery—The Journal of Biological Chemistry—Feb. 23, 2001—pp. 5836-5840—vol. 276—No. 8—The American Society of Biochemistry and Molecular Biology, Inc.—USA.
Gammon et al.—Quantitative Analysis of Permeation Peptide Complexes Labeled with Technetium-99m: Chiral and Sequence-Specific Effects on Net Cell Uptake—Bioconjugate Chemistry—Mar. 4, 2003—pp. 368-376—vol. 14—No. 2—American Chemical Society—USA.
Gotthardt et al.—Interactions of the Low Density Lipoprotein Receptor Gene Family with Cytosolic Adaptor and Scaffold Proteins Suggest Diverse Biological Functions in Cellular Communication and Signal Transduction—The Journal of Biological Chemistry—Aug. 18, 2000—pp. 25616-25624—vol. 275—No. 33—The American Society for Biochemistry and Molecular Biology, Inc.—USA.
Guichard et al.—Antigenic Mimicry of Natural L-Peptides with Retro-Inverso-Peptidomimetics—Proceedings of the National Academy of Sciences—Immunology—Oct. 1994—pp. 9765-9769—vol. 91—The National Academy of Sciences—USA.
Gunaseelan et al.—Synthesis of Poly(ethylene glycol)-Based Saquinavir Prodrug Conjugates and Assessment of Release and Anti-HIV-1 Bioactivity Using a Novel Protease Inhibition Assay—Bioconjugate Chemistry—Oct. 28, 2004—pp. 1322-1333—vol. 15—No. 6—American Chemical Society—USA.
Gura, Trisha—Cancer Models: Systems for Identifying New Drugs Are Often Faulty—Science—Nov. 7, 1997—pp. 1041-1042—No. 278 (5340)—USA.
Hawiger, Jacek—Noninvasive Intracellular Delivery of Functional Peptides and Proteins—Current Opinion in Chemical Biology—1999—pp. 89-94—vol. 3—Elsevier Science Ltd—USA.
Hayashi et al.—Development of Oligoarginine-Drug Conjugates Linked to New Peptidic Self-Cleavable Spacers Toward Effective Intestinal Absorption—Bioorganic and Medicinal Chemistry Letters—Jul. 7, 2007—pp. 5129-5132—vol. 17—ScienceDirect—Elsevier Ltd—USA.
Heemskerk et al.—From Chemical to Drug: Neurodegeneration Drug Screening and the Ethics of Clinical Trials—Commentary—Nature Neuroscience Supplement—Nov. 2002—pp. 1027-1029—vol. 5—Nature Publishing Group—http://www.nature.com/natureneuroscience—USA.
Herve et al.—On the Immunogenic Properties of Retro-Inverso Peptides. Total Retro-Inversion of T-Cell Epitopes Causes a Loss of Binding to MHC II Molecules—Molecular Immunology—1997—pp. 157-163—vol. 34—No. 2—Elsevier Science Ltd.—United Kingdom.
Hillier et al.—*Homo sapiens*—The WashU-Merck EST Project—EMBL Sequence Database—R85141—Aug. 17, 1995—p. 1—XP-002076858—USA.
Ho et al.—Synthetic Protein Transduction Domains: Enhanced Transduction Potential in Vitro and in Vivo—Advances in Brief—Cancer Research—Jan. 15, 2001—pp. 474-477—vol. 61—USA.
Holinger et al.—Bak BH3 Peptides Antagonize Bcl-xL Function and Induce Apoptosis through Cytochrome c-independent Activation of Caspases—The Journal of Biological Chemistry—May 7, 1999—pp. 13298-13304—vol. 274—No. 19—The American Society for Biochemistry and Molecular Biology, Inc.—USA.

(56) References Cited

OTHER PUBLICATIONS

Holzberg et al.—Disruption of the c-JUN-JNK Complex by a Cell-permeable Peptide Containing the c-Jun δ Domain Induces Apoptosis and Affects a Distinct Set of Interleukin-1-induced Inflammatory Genes—The Journal of Biological Chemistry—Oct. 10, 2003—pp. 40213-40223—vol. 278—No. 41—The American Society for Biochemistry and Molecular Biology, Inc.—USA.

Houghten, Richard A.—General Method for the Rapid Solid-Phase Synthesis of Large Numbers of Peptides: Specificity of Antigen-Antibody Interaction at the Level of Individual Amino Acids—Proceedings of the National Academy of Sciences—Immunology—Aug. 1985—pp. 5131-5135—vol. 82—The National Academy of Sciences—USA.

Huq et al.—Specific Recognition of HIV-1 TAR RNA by a D-Tat Peptide—Comment—Nature Structural Biology—Nov. 1997—pp. 881-882—vol. 4—No. 11—Nature Publishing Group—http://www.nature.com/nsmb—USA.

Johnson, Gary L. and Nakamura, Kazuhiro—The c-jun Kinase/Stress-Activated Pathway: Regulation, Function and Role in Human Disease—Biochimica et Biophysica Acta—Jan. 4, 2007—pp. 1341-1348—vol. 1773—ScienceDirect—Elsevier B.V.—The Netherlands.

Jung, Günther (Editor)—Chapter 5—The Versatility of Nonsupport-Bound Combinatorial Libraries—Pinilla et al.—Combinatorial Peptide and Nonpeptide Libraries—A Handbook—May 1997—pp. 139-171—Wiley-VCH—USA.

Jung, Günther (Editor)—Chapter 11—Cyclic Peptide Libraries: Recent Developments—Spatola, Arno F. and Romanovskis, Peteris—Combinatorial Peptide and Nonpeptide Libraries—A Handbook—May 1997—pp. 327-347—Wiley-VCH—USA.

\* cited by examiner

Peptide sequences, Human, Mouse and Rat

A
```
                    ::   **.:
IB2    :  IPSPSVEEPHKHRPTTLRL--TTLGAQDS
IB1    :  PGTGCGDTYRPKRPTTLNLFPQVPRSQDT
c-Jun  :  GAYGYSNPKILKQSMTLNLADPVGNLKPH
ATF2   :  TNEDHLAVHKHKHEMTLKFGPARNDSVIV
```

B
```
             :. . ***** *       **:
L-IB1(s) :  ---RPKRPTTLNLFPQVPRSQD
L-IB1    :  DTYRPKRPTTLNLFPQVPRSQDT
             ooo  o
```

C
```
L-TAT        :  NH2-GRKKRRQRRR-COOH
L-TAT-IB1(s) :  NH2-GRKKRRQRRPP---RPKRPTTLNLFPQVPRSQD-COOH
L-TAT-IB1    :  NH2-GRKKRRQRRPPDTYRPKRPTTLNLFPQVPRSQDT-COOH

D-TAT        :  NH2-RRRQRRKKRG-COOH
D-TAT-IB1(s) :  NH2---DQSRPVQPFLNLTTPRKPR---PPRRRQRRKKRG-COOH
D-TAT-IB1    :  NH2-TDQSRPVQPFLNLTTPRKPRYTDPPRRRQRRKKRG-COOH
```

Fig. 1

Generic Sequences, Human, Mouse and Rat

L-generic-TAT(s)    : NH$_2$-XXXXRKKRRQRRRXXXX-COOH
L-TAT-IB (generic) (s): NH$_2$-XXXXXXXRKKRRQRRRXXXXXRPTTLXLXXXXXXQDX-COOH
L-TAT-IB (generic)   : NH$_2$-XXXXXXXRKKRRQRRRXXXXXXXRPTTLXLXXXXXXQDS/TX-COOH D-generic-TAT(s)    : NH$_2$-XXXXRRRQRRKKRXXXX-COOH
D-TAT-IB (generic) (s): NH$_2$-XDQXXXXXLXLTTPRXXXXXRRRQRRKKRXXXXXXX-COOH
D-TAT-IB (generic)   : NH$_2$-XT/SDQXXXXXLXLTTPRXXXXXXXRRRQRRKKRXXXXXXX-COOH

Fig. 2

```
                       SEQUENCE LISTING

<160> NUMBER OF SEQ ID NOS: 150

<210> SEQ ID NO 1
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Pro Lys Arg Pro Thr Thr Leu Asn Leu Phe Pro Gln Val Pro Arg
1               5                   10                  15

Ser Gln Asp

<210> SEQ ID NO 2
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Asp Gln Ser Arg Pro Val Gln Pro Phe Leu Asn Leu Thr Thr Pro Arg
1               5                   10                  15

Lys Pro Arg

<210> SEQ ID NO 3
<211> LENGTH: 77
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(30)
<223> OTHER INFORMATION: Variable amino acid; region may or may not be
      present
<220> FEATURE:
<221> NAME/KEY: MOD_RES
<222> LOCATION: (31)..(31)
<223> OTHER INFORMATION: Variable amino acid or not present
<220> FEATURE:
<221> NAME/KEY: MOD_RES
<222> LOCATION: (37)..(37)
<223> OTHER INFORMATION: Variable amino acid
<220> FEATURE:
<221> NAME/KEY: MOD_RES
```

```
<222> LOCATION: (39)..(45)
<223> OTHER INFORMATION: Variable amino acid
<220> FEATURE:
<221> NAME/KEY: MOD_RES
<222> LOCATION: (48)..(77)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 3

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Arg
                20                  25                  30

Pro Thr Thr Leu Xaa Leu Xaa Xaa Xaa Xaa Xaa Xaa Gln Asp Xaa
                35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa
65                  70                  75

<210> SEQ ID NO 4
<211> LENGTH: 77
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(30)
<223> OTHER INFORMATION: Variable amino acid; region may or may not be
      present
<220> FEATURE:
<221> NAME/KEY: MOD_RES
<222> LOCATION: (33)..(39)
<223> OTHER INFORMATION: Variable amino acid
<220> FEATURE:
<221> NAME/KEY: MOD_RES
<222> LOCATION: (41)..(41)
<223> OTHER INFORMATION: Variable amino acid
<220> FEATURE:
<221> NAME/KEY: MOD_RES
<222> LOCATION: (47)..(47)
<223> OTHER INFORMATION: Variable amino acid or not present
<220> FEATURE:
<221> NAME/KEY: MOD_RES
<222> LOCATION: (48)..(77)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 4

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Asp Gln
                20                  25                  30

Xaa Xaa Xaa Xaa Xaa Xaa Xaa Leu Xaa Leu Thr Thr Pro Arg Xaa Xaa
                35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa
65                  70                  75
```

```
<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Arg Lys Lys Arg Arg Gln Arg Arg Arg
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Arg Arg Gln Arg Arg Lys Lys Arg Gly
1               5                   10

<210> SEQ ID NO 7
<211> LENGTH: 69
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(30)
<223> OTHER INFORMATION: Variable amino acid; region may or may not be
      present
<220> FEATURE:
<221> NAME/KEY: MOD_RES
<222> LOCATION: (40)..(69)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 7

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Arg Lys
            20                  25                  30

Lys Arg Arg Gln Arg Arg Arg Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa
65

<210> SEQ ID NO 8
<211> LENGTH: 69
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(30)
<223> OTHER INFORMATION: Variable amino acid; region may or may not be
```

```
                                present
<220> FEATURE:
<221> NAME/KEY: MOD_RES
<222> LOCATION: (40)..(69)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 8

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Arg Arg
            20                  25                  30

Arg Gln Arg Arg Lys Lys Arg Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa
65

<210> SEQ ID NO 9
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Arg Lys Lys Arg Arg Gln Arg Arg Pro Pro Arg Pro Lys Arg
1               5                   10                  15

Pro Thr Thr Leu Asn Leu Phe Pro Gln Val Pro Arg Ser Gln Asp
            20                  25                  30

<210> SEQ ID NO 10
<211> LENGTH: 116
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(30)
<223> OTHER INFORMATION: Variable amino acid; region may or may not be
      present
<220> FEATURE:
<221> NAME/KEY: MOD_RES
<222> LOCATION: (40)..(69)
<223> OTHER INFORMATION: Variable amino acid; region may or may not be
      present
<220> FEATURE:
<221> NAME/KEY: MOD_RES
<222> LOCATION: (70)..(70)
<223> OTHER INFORMATION: Variable amino acid or not present
<220> FEATURE:
<221> NAME/KEY: MOD_RES
<222> LOCATION: (76)..(76)
<223> OTHER INFORMATION: Variable amino acid
<220> FEATURE:
<221> NAME/KEY: MOD_RES
<222> LOCATION: (78)..(84)
<223> OTHER INFORMATION: Variable amino acid
<220> FEATURE:
<221> NAME/KEY: MOD_RES
<222> LOCATION: (87)..(116)
<223> OTHER INFORMATION: Variable amino acid; region may or may not be
      present
```

<220> FEATURE:
<223> OTHER INFORMATION: See specification as filed for detailed
     description of substitutions and preferred embodiments

<400> SEQUENCE: 10

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Arg Lys
                20                  25                  30

Lys Arg Arg Gln Arg Arg Arg Xaa Xaa Xaa Xaa Xaa Xaa Xaa Xaa
                35                  40                  45

Xaa Xaa Xaa Xaa Xaa Xaa Xaa Xaa Xaa Xaa Xaa Xaa Xaa Xaa Xaa
        50                  55                  60

Xaa Xaa Xaa Xaa Xaa Xaa Arg Pro Thr Thr Leu Xaa Leu Xaa Xaa Xaa
65                  70                  75                  80

Xaa Xaa Xaa Xaa Gln Asp Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa
        115

<210> SEQ ID NO 11
<211> LENGTH: 31
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 11

Asp Gln Ser Arg Pro Val Gln Pro Phe Leu Asn Leu Thr Thr Pro Arg
1               5                   10                  15

Lys Pro Arg Pro Pro Arg Arg Arg Gln Arg Arg Lys Lys Arg Gly
                20                  25                  30

<210> SEQ ID NO 12
<211> LENGTH: 116
<212> TYPE: PRT
<213> ORGANISM: Artificial Sequence
<220> FEATURE:
<223> OTHER INFORMATION: Description of Artificial Sequence: Synthetic
     peptide
<220> FEATURE:
<221> NAME/KEY: MOD_RES
<222> LOCATION: (1)..(30)
<223> OTHER INFORMATION: Variable amino acid; region may or may not be
     present
<220> FEATURE:
<221> NAME/KEY: MOD_RES
<222> LOCATION: (33)..(39)
<223> OTHER INFORMATION: Variable amino acid
<220> FEATURE:
<221> NAME/KEY: MOD_RES
<222> LOCATION: (41)..(41)
<223> OTHER INFORMATION: Variable amino acid
<220> FEATURE:
<221> NAME/KEY: MOD_RES
<222> LOCATION: (47)..(47)
<223> OTHER INFORMATION: Variable amino acid or not present
<220> FEATURE:
<221> NAME/KEY: MOD_RES
<222> LOCATION: (48)..(77)
<223> OTHER INFORMATION: Variable amino acid; region may or may not be
     present
<220> FEATURE:
<221> NAME/KEY: MOD_RES
<222> LOCATION: (87)..(116)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 12

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Asp Gln
            20                  25                  30

Xaa Xaa Xaa Xaa Xaa Xaa Xaa Leu Xaa Leu Thr Thr Pro Arg Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Arg Arg Arg
65                  70                  75                  80

Gln Arg Arg Lys Lys Arg Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa
        115

<210> SEQ ID NO 13
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Pro Gly Thr Gly Cys Gly Asp Thr Tyr Arg Pro Lys Arg Pro Thr Thr
1               5                   10                  15

Leu Asn Leu Phe Pro Gln Val Pro Arg Ser Gln Asp Thr
            20                  25

<210> SEQ ID NO 14
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ile Pro Ser Pro Ser Val Glu Glu Pro His Lys His Arg Pro Thr Thr
1               5                   10                  15

Leu Arg Leu Thr Thr Leu Gly Ala Gln Asp Ser
            20                  25

<210> SEQ ID NO 15
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Ala Tyr Gly Tyr Ser Asn Pro Lys Ile Leu Lys Gln Ser Met Thr

```
1               5                   10                  15
Leu Asn Leu Ala Asp Pro Val Gly Asn Leu Lys Pro His
                20                  25

<210> SEQ ID NO 16
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Thr Asn Glu Asp His Leu Ala Val His Lys His Lys His Glu Met Thr
1               5                   10                  15
Leu Lys Phe Gly Pro Ala Arg Asn Asp Ser Val Ile Val
                20                  25

<210> SEQ ID NO 17
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Asp Thr Tyr Arg Pro Lys Arg Pro Thr Thr Leu Asn Leu Phe Pro Gln
1               5                   10                  15
Val Pro Arg Ser Gln Asp Thr
                20

<210> SEQ ID NO 18
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Thr Asp Gln Ser Arg Pro Val Gln Pro Phe Leu Asn Leu Thr Thr Pro
1               5                   10                  15
Arg Lys Pro Arg Tyr Thr Asp
                20

<210> SEQ ID NO 19
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Variable amino acid
<220> FEATURE:
<221> NAME/KEY: MOD_RES
<222> LOCATION: (7)..(7)
<223> OTHER INFORMATION: Variable amino acid
<220> FEATURE:
<221> NAME/KEY: MOD_RES
<222> LOCATION: (9)..(15)
<223> OTHER INFORMATION: Variable amino acid
<220> FEATURE:
<221> NAME/KEY: MOD_RES
<222> LOCATION: (18)..(18)
```

```
<223> OTHER INFORMATION: Ser or Thr
<220> FEATURE:
<221> NAME/KEY: MOD_RES
<222> LOCATION: (19)..(19)
<223> OTHER INFORMATION: Variable amino acid

<400> SEQUENCE: 19

Xaa Arg Pro Thr Thr Leu Xaa Leu Xaa Xaa Xaa Xaa Xaa Xaa Gln
1               5                   10                  15

Asp Xaa Xaa

<210> SEQ ID NO 20
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Variable amino acid
<220> FEATURE:
<221> NAME/KEY: MOD_RES
<222> LOCATION: (2)..(2)
<223> OTHER INFORMATION: Ser or Thr
<220> FEATURE:
<221> NAME/KEY: MOD_RES
<222> LOCATION: (5)..(11)
<223> OTHER INFORMATION: Variable amino acid
<220> FEATURE:
<221> NAME/KEY: MOD_RES
<222> LOCATION: (13)..(13)
<223> OTHER INFORMATION: Variable amino acid
<220> FEATURE:
<221> NAME/KEY: MOD_RES
<222> LOCATION: (19)..(19)
<223> OTHER INFORMATION: Variable amino acid

<400> SEQUENCE: 20

Xaa Xaa Asp Gln Xaa Xaa Xaa Xaa Xaa Xaa Xaa Leu Xaa Leu Thr Thr
1               5                   10                  15

Pro Arg Xaa

<210> SEQ ID NO 21
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Variable amino acid
<220> FEATURE:
<221> NAME/KEY: MOD_RES
<222> LOCATION: (14)..(17)
<223> OTHER INFORMATION: Variable amino acid

<400> SEQUENCE: 21

Xaa Xaa Xaa Xaa Arg Lys Lys Arg Arg Gln Arg Arg Arg Xaa Xaa Xaa
1               5                   10                  15

Xaa

<210> SEQ ID NO 22
<211> LENGTH: 17
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Variable amino acid
<220> FEATURE:
<221> NAME/KEY: MOD_RES
<222> LOCATION: (14)..(17)
<223> OTHER INFORMATION: Variable amino acid

<400> SEQUENCE: 22

Xaa Xaa Xaa Xaa Arg Arg Arg Gln Arg Arg Lys Lys Arg Xaa Xaa Xaa
1               5                   10                  15

Xaa

<210> SEQ ID NO 23
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Arg Lys Lys Arg Arg Gln Arg Arg Pro Pro Asp Thr Tyr Arg
1               5                   10                  15

Pro Lys Arg Pro Thr Thr Leu Asn Leu Phe Pro Gln Val Pro Arg Ser
                20                  25                  30

Gln Asp Thr
        35

<210> SEQ ID NO 24
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(7)
<223> OTHER INFORMATION: Variable amino acid
<220> FEATURE:
<221> NAME/KEY: MOD_RES
<222> LOCATION: (17)..(24)
<223> OTHER INFORMATION: Variable amino acid
<220> FEATURE:
<221> NAME/KEY: MOD_RES
<222> LOCATION: (30)..(30)
<223> OTHER INFORMATION: Variable amino acid
<220> FEATURE:
<221> NAME/KEY: MOD_RES
<222> LOCATION: (32)..(38)
<223> OTHER INFORMATION: Variable amino acid
<220> FEATURE:
<221> NAME/KEY: MOD_RES
<222> LOCATION: (41)..(41)
<223> OTHER INFORMATION: Ser or Thr
<220> FEATURE:
<221> NAME/KEY: MOD_RES
<222> LOCATION: (42)..(42)
<223> OTHER INFORMATION: Variable amino acid

<400> SEQUENCE: 24

Xaa Xaa Xaa Xaa Xaa Xaa Xaa Arg Lys Lys Arg Arg Gln Arg Arg
1               5                   10                  15

Xaa Xaa Xaa Xaa Xaa Xaa Xaa Xaa Arg Pro Thr Thr Leu Xaa Leu Xaa
                20                  25                  30
```

Xaa Xaa Xaa Xaa Xaa Xaa Gln Asp Xaa Xaa
         35                  40

<210> SEQ ID NO 25
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Thr Asp Gln Ser Arg Pro Val Gln Pro Phe Leu Asn Leu Thr Thr Pro
1               5                   10                  15

Arg Lys Pro Arg Tyr Thr Asp Pro Pro Arg Arg Arg Gln Arg Arg Lys
            20                  25                  30

Lys Arg Gly
        35

<210> SEQ ID NO 26
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Variable amino acid
<220> FEATURE:
<221> NAME/KEY: MOD_RES
<222> LOCATION: (2)..(2)
<223> OTHER INFORMATION: Ser or Thr
<220> FEATURE:
<221> NAME/KEY: MOD_RES
<222> LOCATION: (5)..(11)
<223> OTHER INFORMATION: Variable amino acid
<220> FEATURE:
<221> NAME/KEY: MOD_RES
<222> LOCATION: (13)..(13)
<223> OTHER INFORMATION: Variable amino acid
<220> FEATURE:
<221> NAME/KEY: MOD_RES
<222> LOCATION: (19)..(26)
<223> OTHER INFORMATION: Variable amino acid
<220> FEATURE:
<221> NAME/KEY: MOD_RES
<222> LOCATION: (36)..(42)
<223> OTHER INFORMATION: Variable amino acid

<400> SEQUENCE: 26

Xaa Xaa Asp Gln Xaa Xaa Xaa Xaa Xaa Xaa Xaa Leu Xaa Leu Thr Thr
1               5                   10                  15

Pro Arg Xaa Xaa Xaa Xaa Xaa Xaa Xaa Xaa Arg Arg Arg Gln Arg Arg
            20                  25                  30

Lys Lys Arg Xaa Xaa Xaa Xaa Xaa Xaa Xaa
        35                  40

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 27
cgcttgatga gtcagccgga a                                              21

```
<210> SEQ ID NO 28
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gln Ser Arg Pro Val Gln Pro Phe Leu Asn Leu Thr Thr Pro Arg Lys
1               5                   10                  15

Pro Arg

<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ser Arg Pro Val Gln Pro Phe Leu Asn Leu Thr Thr Pro Arg Lys Pro
1               5                   10                  15

Arg

<210> SEQ ID NO 30
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Pro Val Gln Pro Phe Leu Asn Leu Thr Thr Pro Arg Lys Pro Arg
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Pro Val Gln Pro Phe Leu Asn Leu Thr Thr Pro Arg Lys Pro Arg
1               5                   10                  15

<210> SEQ ID NO 32
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Val Gln Pro Phe Leu Asn Leu Thr Thr Pro Arg Lys Pro Arg
1               5                   10

<210> SEQ ID NO 33
<211> LENGTH: 18
<212> TYPE: PRT
```

<213> ORGANISM: Artificial Sequence
<220> FEATURE:
<223> OTHER INFORMATION: Description of Artificial Sequence: Synthetic peptide

<400> SEQUENCE: 33

Asp Gln Ser Arg Pro Val Gln Pro Phe Leu Asn Leu Thr Thr Pro Arg
1               5                   10                  15

Lys Pro

<210> SEQ ID NO 34
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 34

Asp Gln Ser Arg Pro Val Gln Pro Phe Leu Asn Leu Thr Thr Pro Arg
1               5                   10                  15

Lys

<210> SEQ ID NO 35
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 35

Asp Gln Ser Arg Pro Val Gln Pro Phe Leu Asn Leu Thr Thr Pro Arg
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 36

Asp Gln Ser Arg Pro Val Gln Pro Phe Leu Asn Leu Thr Thr Pro
1               5                   10                  15

<210> SEQ ID NO 37
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 37

Asp Gln Ser Arg Pro Val Gln Pro Phe Leu Asn Leu Thr Thr
1               5                   10

<210> SEQ ID NO 38
<211> LENGTH: 17
<212> TYPE: PRT
<213> ORGANISM: Artificial Sequence
<220> FEATURE:
<223> OTHER INFORMATION: Description of Artificial Sequence: Synthetic peptide

```
<400> SEQUENCE: 38

Gln Ser Arg Pro Val Gln Pro Phe Leu Asn Leu Thr Thr Pro Arg Lys
1               5                   10                  15

Pro

<210> SEQ ID NO 39
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ser Arg Pro Val Gln Pro Phe Leu Asn Leu Thr Thr Pro Arg Lys Pro
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ser Arg Pro Val Gln Pro Phe Leu Asn Leu Thr Thr Pro Arg Lys
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Arg Pro Val Gln Pro Phe Leu Asn Leu Thr Thr Pro Arg Lys Pro
1               5                   10                  15

<210> SEQ ID NO 42
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Arg Pro Val Gln Pro Phe Leu Asn Leu Thr Thr Pro Arg Lys
1               5                   10

<210> SEQ ID NO 43
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Pro Val Gln Pro Phe Leu Asn Leu Thr Thr Pro
1               5                   10

<210> SEQ ID NO 44
```

```
<211> LENGTH: 59
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Variable amino acid or not present
<220> FEATURE:
<221> NAME/KEY: MOD_RES
<222> LOCATION: (20)..(49)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 44

Gln Ser Arg Pro Val Gln Pro Phe Leu Asn Leu Thr Thr Pro Arg Lys
1               5                   10                  15

Pro Arg Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Arg Arg Arg Gln Arg Arg Lys Lys Arg Gly
    50                  55

<210> SEQ ID NO 45
<211> LENGTH: 58
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Variable amino acid or not present
<220> FEATURE:
<221> NAME/KEY: MOD_RES
<222> LOCATION: (19)..(48)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 45

Ser Arg Pro Val Gln Pro Phe Leu Asn Leu Thr Thr Pro Arg Lys Pro
1               5                   10                  15

Arg Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Arg Arg Arg Gln Arg Arg Lys Lys Arg Gly
    50                  55

<210> SEQ ID NO 46
<211> LENGTH: 57
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
```

```
<223> OTHER INFORMATION: Variable amino acid or not present
<220> FEATURE:
<221> NAME/KEY: MOD_RES
<222> LOCATION: (18)..(47)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 46

Arg Pro Val Gln Pro Phe Leu Asn Leu Thr Thr Pro Arg Lys Pro Arg
1               5                   10                  15

Xaa Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa Arg
            35                  40                  45

Arg Arg Gln Arg Arg Lys Lys Arg Gly
        50                  55

<210> SEQ ID NO 47
<211> LENGTH: 56
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Variable amino acid or not present
<220> FEATURE:
<221> NAME/KEY: MOD_RES
<222> LOCATION: (17)..(46)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 47

Pro Val Gln Pro Phe Leu Asn Leu Thr Thr Pro Arg Lys Pro Arg Xaa
1               5                   10                  15

Xaa Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Arg Arg
            35                  40                  45

Arg Gln Arg Arg Lys Lys Arg Gly
        50                  55

<210> SEQ ID NO 48
<211> LENGTH: 55
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Variable amino acid or not present
<220> FEATURE:
<221> NAME/KEY: MOD_RES
<222> LOCATION: (16)..(45)
<223> OTHER INFORMATION: Variable amino acid; region may or may not be
      present
<220> FEATURE:
<223> OTHER INFORMATION: See specification as filed for detailed
      description of substitutions and preferred embodiments
```

```
<400> SEQUENCE: 48

Val Gln Pro Phe Leu Asn Leu Thr Thr Pro Arg Lys Pro Arg Xaa Xaa
1               5                   10                  15

Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Arg Arg Arg
        35                  40                  45

Gln Arg Arg Lys Lys Arg Gly
    50                  55

<210> SEQ ID NO 49
<211> LENGTH: 59
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Variable amino acid or not present
<220> FEATURE:
<221> NAME/KEY: MOD_RES
<222> LOCATION: (20)..(49)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 49

Asp Gln Ser Arg Pro Val Gln Pro Phe Leu Asn Leu Thr Thr Pro Arg
1               5                   10                  15

Lys Pro Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Arg Arg Arg Gln Arg Arg Lys Lys Arg Gly
    50                  55

<210> SEQ ID NO 50
<211> LENGTH: 58
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Variable amino acid or not present
<220> FEATURE:
<221> NAME/KEY: MOD_RES
<222> LOCATION: (19)..(48)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 50

Asp Gln Ser Arg Pro Val Gln Pro Phe Leu Asn Leu Thr Thr Pro Arg
1               5                   10                  15

Lys Xaa Xaa Xaa Xaa Xaa Xaa Xaa Xaa Xaa Xaa Xaa Xaa Xaa Xaa Xaa
            20                  25                  30
```

```
Xaa Xaa Xaa Xaa Xaa Xaa Xaa Xaa Xaa Xaa Xaa Xaa Xaa Xaa
            35                  40                  45

Arg Arg Arg Gln Arg Arg Lys Lys Arg Gly
 50                  55

<210> SEQ ID NO 51
<211> LENGTH: 57
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Variable amino acid or not present
<220> FEATURE:
<221> NAME/KEY: MOD_RES
<222> LOCATION: (18)..(47)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 51

Asp Gln Ser Arg Pro Val Gln Pro Phe Leu Asn Leu Thr Thr Pro Arg
 1               5                  10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Arg
            35                  40                  45

Arg Arg Gln Arg Arg Lys Lys Arg Gly
 50                  55

<210> SEQ ID NO 52
<211> LENGTH: 56
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Variable amino acid or not present
<220> FEATURE:
<221> NAME/KEY: MOD_RES
<222> LOCATION: (17)..(46)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 52

Asp Gln Ser Arg Pro Val Gln Pro Phe Leu Asn Leu Thr Thr Pro Xaa
 1               5                  10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Arg Arg
            35                  40                  45

Arg Gln Arg Arg Lys Lys Arg Gly
 50                  55

<210> SEQ ID NO 53
<211> LENGTH: 55
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Variable amino acid or not present
<220> FEATURE:
<221> NAME/KEY: MOD_RES
<222> LOCATION: (16)..(45)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 53

Asp Gln Ser Arg Pro Val Gln Pro Phe Leu Asn Leu Thr Thr Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Arg Arg Arg
        35                  40                  45

Gln Arg Arg Lys Lys Arg Gly
    50                  55

<210> SEQ ID NO 54
<211> LENGTH: 58
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Variable amino acid or not present
<220> FEATURE:
<221> NAME/KEY: MOD_RES
<222> LOCATION: (19)..(48)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 54

Gln Ser Arg Pro Val Gln Pro Phe Leu Asn Leu Thr Thr Pro Arg Lys
1               5                   10                  15

Pro Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Arg Arg Arg Gln Arg Arg Lys Lys Arg Gly
    50                  55

<210> SEQ ID NO 55
<211> LENGTH: 57
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Variable amino acid or not present
```

-continued

```
<220> FEATURE:
<221> NAME/KEY: MOD_RES
<222> LOCATION: (18)..(47)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 55

Ser Arg Pro Val Gln Pro Phe Leu Asn Leu Thr Thr Pro Arg Lys Pro
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Arg
        35                  40                  45

Arg Arg Gln Arg Arg Lys Lys Arg Gly
    50                  55

<210> SEQ ID NO 56
<211> LENGTH: 56
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Variable amino acid or not present
<220> FEATURE:
<221> NAME/KEY: MOD_RES
<222> LOCATION: (17)..(46)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 56

Ser Arg Pro Val Gln Pro Phe Leu Asn Leu Thr Thr Pro Arg Lys Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Arg Arg
        35                  40                  45

Arg Gln Arg Arg Lys Lys Arg Gly
    50                  55

<210> SEQ ID NO 57
<211> LENGTH: 56
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Variable amino acid or not present
<220> FEATURE:
<221> NAME/KEY: MOD_RES
<222> LOCATION: (17)..(46)
<223> OTHER INFORMATION: Variable amino acid; region may or may not be
      present
<220> FEATURE:
<223> OTHER INFORMATION: See specification as filed for detailed
      description of substitutions and preferred embodiments
```

-continued

```
<400> SEQUENCE: 57

Arg Pro Val Gln Pro Phe Leu Asn Leu Thr Thr Pro Arg Lys Pro Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Arg Arg
        35                  40                  45

Arg Gln Arg Arg Lys Lys Arg Gly
    50                  55

<210> SEQ ID NO 58
<211> LENGTH: 55
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Variable amino acid or not present
<220> FEATURE:
<221> NAME/KEY: MOD_RES
<222> LOCATION: (16)..(45)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 58

Arg Pro Val Gln Pro Phe Leu Asn Leu Thr Thr Pro Arg Lys Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Arg Arg Arg
        35                  40                  45

Gln Arg Arg Lys Lys Arg Gly
    50                  55

<210> SEQ ID NO 59
<211> LENGTH: 52
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Variable amino acid or not present
<220> FEATURE:
<221> NAME/KEY: MOD_RES
<222> LOCATION: (13)..(42)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 59

Pro Val Gln Pro Phe Leu Asn Leu Thr Thr Pro Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Arg Arg Arg Gln Arg Arg
```

Lys Lys Arg Gly
    50

<210> SEQ ID NO 60
<211> LENGTH: 58
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Variable amino acid or not present
<220> FEATURE:
<221> NAME/KEY: MOD_RES
<222> LOCATION: (20)..(49)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 60

Gln Ser Arg Pro Val Gln Pro Phe Leu Asn Leu Thr Thr Pro Arg Lys
1               5                   10                  15

Pro Arg Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Arg Arg Arg Gln Arg Arg Lys Lys Arg
    50                  55

<210> SEQ ID NO 61
<211> LENGTH: 57
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Variable amino acid or not present
<220> FEATURE:
<221> NAME/KEY: MOD_RES
<222> LOCATION: (20)..(49)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 61

Gln Ser Arg Pro Val Gln Pro Phe Leu Asn Leu Thr Thr Pro Arg Lys
1               5                   10                  15

Pro Arg Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Arg Arg Arg Gln Arg Arg Lys Lys
    50                  55

<210> SEQ ID NO 62
<211> LENGTH: 58
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Variable amino acid or not present
<220> FEATURE:
<221> NAME/KEY: MOD_RES
<222> LOCATION: (20)..(49)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 62

Gln Ser Arg Pro Val Gln Pro Phe Leu Asn Leu Thr Thr Pro Arg Lys
1               5                   10                  15

Pro Arg Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Arg Arg Gln Arg Arg Lys Lys Arg Gly
    50                  55

<210> SEQ ID NO 63
<211> LENGTH: 57
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Variable amino acid or not present
<220> FEATURE:
<221> NAME/KEY: MOD_RES
<222> LOCATION: (20)..(49)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 63

Gln Ser Arg Pro Val Gln Pro Phe Leu Asn Leu Thr Thr Pro Arg Lys
1               5                   10                  15

Pro Arg Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Arg Gln Arg Arg Lys Lys Arg Gly
    50                  55

<210> SEQ ID NO 64
<211> LENGTH: 57
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Variable amino acid or not present
<220> FEATURE:
```

```
<221> NAME/KEY: MOD_RES
<222> LOCATION: (20)..(49)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 64

Gln Ser Arg Pro Val Gln Pro Phe Leu Asn Leu Thr Thr Pro Arg Lys
1               5                   10                  15

Pro Arg Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Arg Arg Gln Arg Arg Lys Lys Arg
    50                  55

<210> SEQ ID NO 65
<211> LENGTH: 56
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Variable amino acid or not present
<220> FEATURE:
<221> NAME/KEY: MOD_RES
<222> LOCATION: (20)..(49)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 65

Gln Ser Arg Pro Val Gln Pro Phe Leu Asn Leu Thr Thr Pro Arg Lys
1               5                   10                  15

Pro Arg Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Arg Gln Arg Arg Lys Lys Arg
    50                  55

<210> SEQ ID NO 66
<211> LENGTH: 55
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Variable amino acid or not present
<220> FEATURE:
<221> NAME/KEY: MOD_RES
<222> LOCATION: (20)..(49)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 66
```

```
Gln Ser Arg Pro Val Gln Pro Phe Leu Asn Leu Thr Thr Pro Arg Lys
1               5                   10                  15

Pro Arg Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Arg Gln Arg Arg Lys Lys
    50                  55

<210> SEQ ID NO 67
<211> LENGTH: 58
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Variable amino acid or not present
<220> FEATURE:
<221> NAME/KEY: MOD_RES
<222> LOCATION: (20)..(49)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 67

Gln Ser Arg Pro Val Gln Pro Phe Leu Asn Leu Thr Thr Pro Arg Lys
1               5                   10                  15

Pro Arg Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Arg Arg Arg Gln Arg Arg Lys Lys Arg
    50                  55

<210> SEQ ID NO 68
<211> LENGTH: 57
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Variable amino acid or not present
<220> FEATURE:
<221> NAME/KEY: MOD_RES
<222> LOCATION: (19)..(48)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 68

Ser Arg Pro Val Gln Pro Phe Leu Asn Leu Thr Thr Pro Arg Lys Pro
1               5                   10                  15

Arg Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45
```

```
Arg Arg Arg Gln Arg Arg Lys Lys Arg
    50                  55

<210> SEQ ID NO 69
<211> LENGTH: 56
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Variable amino acid or not present
<220> FEATURE:
<221> NAME/KEY: MOD_RES
<222> LOCATION: (18)..(47)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 69

Arg Pro Val Gln Pro Phe Leu Asn Leu Thr Thr Pro Arg Lys Pro Arg
1               5                   10                  15

Xaa Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa Arg
            35                  40                  45

Arg Arg Gln Arg Arg Lys Lys Arg
    50                  55

<210> SEQ ID NO 70
<211> LENGTH: 55
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Variable amino acid or not present
<220> FEATURE:
<221> NAME/KEY: MOD_RES
<222> LOCATION: (17)..(46)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 70

Pro Val Gln Pro Phe Leu Asn Leu Thr Thr Pro Arg Lys Pro Arg Xaa
1               5                   10                  15

Xaa Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Arg Arg
            35                  40                  45

Arg Gln Arg Arg Lys Lys Arg
    50                  55

<210> SEQ ID NO 71
<211> LENGTH: 54
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Variable amino acid or not present
<220> FEATURE:
<221> NAME/KEY: MOD_RES
<222> LOCATION: (16)..(45)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 71

Val Gln Pro Phe Leu Asn Leu Thr Thr Pro Arg Lys Pro Arg Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Arg Arg Arg
            35                  40                  45

Gln Arg Arg Lys Lys Arg
    50

<210> SEQ ID NO 72
<211> LENGTH: 58
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Variable amino acid or not present
<220> FEATURE:
<221> NAME/KEY: MOD_RES
<222> LOCATION: (20)..(49)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 72

Asp Gln Ser Arg Pro Val Gln Pro Phe Leu Asn Leu Thr Thr Pro Arg
1               5                   10                  15

Lys Pro Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
            35                  40                  45

Xaa Arg Arg Arg Gln Arg Arg Lys Lys Arg
    50                  55

<210> SEQ ID NO 73
<211> LENGTH: 57
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Variable amino acid or not present
<220> FEATURE:
<221> NAME/KEY: MOD_RES
```

<222> LOCATION: (19)..(48)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 73

Asp Gln Ser Arg Pro Val Gln Pro Phe Leu Asn Leu Thr Thr Pro Arg
1               5                   10                  15

Lys Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Arg Arg Arg Gln Arg Arg Lys Lys Arg
    50                  55

<210> SEQ ID NO 74
<211> LENGTH: 56
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Variable amino acid or not present
<220> FEATURE:
<221> NAME/KEY: MOD_RES
<222> LOCATION: (18)..(47)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 74

Asp Gln Ser Arg Pro Val Gln Pro Phe Leu Asn Leu Thr Thr Pro Arg
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Arg
        35                  40                  45

Arg Arg Gln Arg Arg Lys Lys Arg
    50                  55

<210> SEQ ID NO 75
<211> LENGTH: 55
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Variable amino acid or not present
<220> FEATURE:
<221> NAME/KEY: MOD_RES
<222> LOCATION: (17)..(46)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 75

```
Asp Gln Ser Arg Pro Val Gln Pro Phe Leu Asn Leu Thr Thr Pro Xaa
1               5                  10                 15

Xaa Xaa Xaa Xaa Xaa Xaa Xaa Xaa Xaa Xaa Xaa Xaa Xaa Xaa Xaa
            20                  25                 30

Xaa Xaa Xaa Xaa Xaa Xaa Xaa Xaa Xaa Xaa Xaa Xaa Xaa Arg Arg
        35                  40                 45

Arg Gln Arg Arg Lys Lys Arg
    50                  55

<210> SEQ ID NO 76
<211> LENGTH: 54
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Variable amino acid or not present
<220> FEATURE:
<221> NAME/KEY: MOD_RES
<222> LOCATION: (16)..(45)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 76

Asp Gln Ser Arg Pro Val Gln Pro Phe Leu Asn Leu Thr Thr Xaa Xaa
1               5                  10                 15

Xaa Xaa Xaa Xaa Xaa Xaa Xaa Xaa Xaa Xaa Xaa Xaa Xaa Xaa Xaa
            20                  25                 30

Xaa Xaa Xaa Xaa Xaa Xaa Xaa Xaa Xaa Xaa Xaa Xaa Arg Arg Arg
        35                  40                 45

Gln Arg Arg Lys Lys Arg
    50

<210> SEQ ID NO 77
<211> LENGTH: 57
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Variable amino acid or not present
<220> FEATURE:
<221> NAME/KEY: MOD_RES
<222> LOCATION: (19)..(48)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 77

Gln Ser Arg Pro Val Gln Pro Phe Leu Asn Leu Thr Thr Pro Arg Lys
1               5                  10                 15

Pro Xaa Xaa Xaa Xaa Xaa Xaa Xaa Xaa Xaa Xaa Xaa Xaa Xaa Xaa
            20                  25                 30

Xaa Xaa Xaa Xaa Xaa Xaa Xaa Xaa Xaa Xaa Xaa Xaa Xaa Xaa Xaa
        35                  40                 45
```

```
Arg Arg Arg Gln Arg Arg Lys Lys Arg
    50                  55

<210> SEQ ID NO 78
<211> LENGTH: 56
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Variable amino acid or not present
<220> FEATURE:
<221> NAME/KEY: MOD_RES
<222> LOCATION: (18)..(47)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 78

Ser Arg Pro Val Gln Pro Phe Leu Asn Leu Thr Thr Pro Arg Lys Pro
1               5                   10                  15

Xaa Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa Arg
            35                  40                  45

Arg Arg Gln Arg Arg Lys Lys Arg
    50                  55

<210> SEQ ID NO 79
<211> LENGTH: 55
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Variable amino acid or not present
<220> FEATURE:
<221> NAME/KEY: MOD_RES
<222> LOCATION: (17)..(46)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 79

Ser Arg Pro Val Gln Pro Phe Leu Asn Leu Thr Thr Pro Arg Lys Xaa
1               5                   10                  15

Xaa Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Arg Arg
            35                  40                  45

Arg Gln Arg Arg Lys Lys Arg
    50                  55

<210> SEQ ID NO 80
<211> LENGTH: 55
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Variable amino acid or not present
<220> FEATURE:
<221> NAME/KEY: MOD_RES
<222> LOCATION: (17)..(46)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 80

Arg Pro Val Gln Pro Phe Leu Asn Leu Thr Thr Pro Arg Lys Pro Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Arg Arg
        35                  40                  45

Arg Gln Arg Arg Lys Lys Arg
    50                  55

<210> SEQ ID NO 81
<211> LENGTH: 54
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Variable amino acid or not present
<220> FEATURE:
<221> NAME/KEY: MOD_RES
<222> LOCATION: (16)..(45)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 81

Arg Pro Val Gln Pro Phe Leu Asn Leu Thr Thr Pro Arg Lys Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Arg Arg Arg
        35                  40                  45

Gln Arg Arg Lys Lys Arg
    50

<210> SEQ ID NO 82
<211> LENGTH: 51
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Variable amino acid or not present
<220> FEATURE:
<221> NAME/KEY: MOD_RES
<222> LOCATION: (13)..(42)
```

```
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 82

Pro Val Gln Pro Phe Leu Asn Leu Thr Thr Pro Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Arg Arg Arg Gln Arg Arg
        35                  40                  45

Lys Lys Arg
    50

<210> SEQ ID NO 83
<211> LENGTH: 57
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Variable amino acid or not present
<220> FEATURE:
<221> NAME/KEY: MOD_RES
<222> LOCATION: (20)..(49)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 83

Gln Ser Arg Pro Val Gln Pro Phe Leu Asn Leu Thr Thr Pro Arg Lys
1               5                   10                  15

Pro Arg Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Arg Arg Arg Gln Arg Arg Lys Lys
    50                  55

<210> SEQ ID NO 84
<211> LENGTH: 58
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Variable amino acid or not present
<220> FEATURE:
<221> NAME/KEY: MOD_RES
<222> LOCATION: (19)..(48)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 84

Ser Arg Pro Val Gln Pro Phe Leu Asn Leu Thr Thr Pro Arg Lys Pro
```

```
 1               5                   10                  15
Arg Xaa Xaa Xaa Xaa Xaa Xaa Xaa Xaa Xaa Xaa Xaa Xaa Xaa
                20                  25                  30
Xaa Xaa Xaa Xaa Xaa Xaa Xaa Xaa Xaa Xaa Xaa Xaa Xaa Xaa
                35                  40                  45
Arg Arg Arg Gln Arg Arg Lys Lys Arg Gly
    50                  55

<210> SEQ ID NO 85
<211> LENGTH: 55
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Variable amino acid or not present
<220> FEATURE:
<221> NAME/KEY: MOD_RES
<222> LOCATION: (18)..(47)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 85

Arg Pro Val Gln Pro Phe Leu Asn Leu Thr Thr Pro Arg Lys Pro Arg
1               5                   10                  15
Xaa Xaa Xaa Xaa Xaa Xaa Xaa Xaa Xaa Xaa Xaa Xaa Xaa Xaa Xaa
                20                  25                  30
Xaa Xaa Xaa Xaa Xaa Xaa Xaa Xaa Xaa Xaa Xaa Xaa Xaa Xaa Arg
            35                  40                  45
Arg Arg Gln Arg Arg Lys Lys
    50                  55

<210> SEQ ID NO 86
<211> LENGTH: 54
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Variable amino acid or not present
<220> FEATURE:
<221> NAME/KEY: MOD_RES
<222> LOCATION: (17)..(46)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 86

Pro Val Gln Pro Phe Leu Asn Leu Thr Thr Pro Arg Lys Pro Arg Xaa
1               5                   10                  15
Xaa Xaa Xaa Xaa Xaa Xaa Xaa Xaa Xaa Xaa Xaa Xaa Xaa Xaa Xaa
                20                  25                  30
Xaa Xaa Xaa Xaa Xaa Xaa Xaa Xaa Xaa Xaa Xaa Xaa Xaa Arg Arg
            35                  40                  45
Arg Gln Arg Arg Lys Lys
```

<210> SEQ ID NO 87
<211> LENGTH: 53
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Variable amino acid or not present
<220> FEATURE:
<221> NAME/KEY: MOD_RES
<222> LOCATION: (16)..(45)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 87

Val Gln Pro Phe Leu Asn Leu Thr Thr Pro Arg Lys Pro Arg Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Arg Arg Arg
        35                  40                  45

Gln Arg Arg Lys Lys
    50

<210> SEQ ID NO 88
<211> LENGTH: 57
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Variable amino acid or not present
<220> FEATURE:
<221> NAME/KEY: MOD_RES
<222> LOCATION: (20)..(49)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 88

Asp Gln Ser Arg Pro Val Gln Pro Phe Leu Asn Leu Thr Thr Pro Arg
1               5                   10                  15

Lys Pro Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Arg Arg Arg Gln Arg Arg Lys Lys
    50                  55

<210> SEQ ID NO 89
<211> LENGTH: 56
<212> TYPE: PRT
<213> ORGANISM: Artificial Sequence
<220> FEATURE:
<223> OTHER INFORMATION: Description of Artificial Sequence: Synthetic

```
       peptide
<220> FEATURE:
<221> NAME/KEY: MOD_RES
<222> LOCATION: (18)..(18)
<223> OTHER INFORMATION: Variable amino acid or not present
<220> FEATURE:
<221> NAME/KEY: MOD_RES
<222> LOCATION: (19)..(48)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 89

Asp Gln Ser Arg Pro Val Gln Pro Phe Leu Asn Leu Thr Thr Pro Arg
1               5                   10                  15

Lys Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Arg Arg Arg Gln Arg Arg Lys Lys
    50                  55

<210> SEQ ID NO 90
<211> LENGTH: 55
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Variable amino acid or not present
<220> FEATURE:
<221> NAME/KEY: MOD_RES
<222> LOCATION: (18)..(47)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 90

Asp Gln Ser Arg Pro Val Gln Pro Phe Leu Asn Leu Thr Thr Pro Arg
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Arg
        35                  40                  45

Arg Arg Gln Arg Arg Lys Lys
    50                  55

<210> SEQ ID NO 91
<211> LENGTH: 54
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Variable amino acid or not present
<220> FEATURE:
<221> NAME/KEY: MOD_RES
<222> LOCATION: (17)..(46)
<223> OTHER INFORMATION: Variable amino acid; region may or may not be
``` present
<220> FEATURE:
<223> OTHER INFORMATION: See specification as filed for detailed
      description of substitutions and preferred embodiments

<400> SEQUENCE: 91

Asp Gln Ser Arg Pro Val Gln Pro Phe Leu Asn Leu Thr Thr Pro Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Arg Arg
        35                  40                  45

Arg Gln Arg Arg Lys Lys
    50

<210> SEQ ID NO 92
<211> LENGTH: 53
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Variable amino acid or not present
<220> FEATURE:
<221> NAME/KEY: MOD_RES
<222> LOCATION: (16)..(45)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 92

Asp Gln Ser Arg Pro Val Gln Pro Phe Leu Asn Leu Thr Thr Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Arg Arg Arg
        35                  40                  45

Gln Arg Arg Lys Lys
    50

<210> SEQ ID NO 93
<211> LENGTH: 56
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Variable amino acid or not present
<220> FEATURE:
<221> NAME/KEY: MOD_RES
<222> LOCATION: (19)..(48)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 93

Gln Ser Arg Pro Val Gln Pro Phe Leu Asn Leu Thr Thr Pro Arg Lys
1               5                   10                  15

```
Pro Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Arg Arg Arg Gln Arg Arg Lys Lys
    50                  55
```

<210> SEQ ID NO 94
<211> LENGTH: 55
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Variable amino acid or not present
<220> FEATURE:
<221> NAME/KEY: MOD_RES
<222> LOCATION: (18)..(47)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 94

```
Ser Arg Pro Val Gln Pro Phe Leu Asn Leu Thr Thr Pro Arg Lys Pro
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Arg
        35                  40                  45

Arg Arg Gln Arg Arg Lys Lys
    50                  55
```

<210> SEQ ID NO 95
<211> LENGTH: 54
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Variable amino acid or not present
<220> FEATURE:
<221> NAME/KEY: MOD_RES
<222> LOCATION: (17)..(46)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 95

```
Ser Arg Pro Val Gln Pro Phe Leu Asn Leu Thr Thr Pro Arg Lys Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Arg Arg
        35                  40                  45

Arg Gln Arg Arg Lys Lys
    50
```

```
<210> SEQ ID NO 96
<211> LENGTH: 54
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Variable amino acid or not present
<220> FEATURE:
<221> NAME/KEY: MOD_RES
<222> LOCATION: (17)..(46)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 96

Arg Pro Val Gln Pro Phe Leu Asn Leu Thr Thr Pro Arg Lys Pro Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Arg Arg
        35                  40                  45

Arg Gln Arg Arg Lys Lys
    50

<210> SEQ ID NO 97
<211> LENGTH: 53
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Variable amino acid or not present
<220> FEATURE:
<221> NAME/KEY: MOD_RES
<222> LOCATION: (16)..(45)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 97

Arg Pro Val Gln Pro Phe Leu Asn Leu Thr Thr Pro Arg Lys Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Arg Arg Arg
        35                  40                  45

Gln Arg Arg Lys Lys
    50

<210> SEQ ID NO 98
<211> LENGTH: 50
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (12)..(12)
<223> OTHER INFORMATION: Variable amino acid or not present
<220> FEATURE:
<221> NAME/KEY: MOD_RES
<222> LOCATION: (13)..(42)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 98

Pro Val Gln Pro Phe Leu Asn Leu Thr Thr Pro Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Arg Arg Gln Arg Arg
        35                  40                  45

Lys Lys
    50

<210> SEQ ID NO 99
<211> LENGTH: 57
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Variable amino acid or not present
<220> FEATURE:
<221> NAME/KEY: MOD_RES
<222> LOCATION: (20)..(49)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 99

Gln Ser Arg Pro Val Gln Pro Phe Leu Asn Leu Thr Thr Pro Arg Lys
1               5                   10                  15

Pro Arg Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Arg Arg Gln Arg Arg Lys Lys Arg
    50                  55

<210> SEQ ID NO 100
<211> LENGTH: 56
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Variable amino acid or not present
<220> FEATURE:
<221> NAME/KEY: MOD_RES
<222> LOCATION: (19)..(48)
<223> OTHER INFORMATION: Variable amino acid; region may or may not be
      present
```

```
<220> FEATURE:
<223> OTHER INFORMATION: See specification as filed for detailed
      description of substitutions and preferred embodiments

<400> SEQUENCE: 100

Ser Arg Pro Val Gln Pro Phe Leu Asn Leu Thr Thr Pro Arg Lys Pro
1               5                   10                  15

Arg Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa Xaa
            35                  40                  45

Arg Arg Gln Arg Arg Lys Lys Arg
        50                  55

<210> SEQ ID NO 101
<211> LENGTH: 55
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Variable amino acid or not present
<220> FEATURE:
<221> NAME/KEY: MOD_RES
<222> LOCATION: (18)..(47)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 101

Arg Pro Val Gln Pro Phe Leu Asn Leu Thr Thr Pro Arg Lys Pro Arg
1               5                   10                  15

Xaa Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa Arg
            35                  40                  45

Arg Gln Arg Arg Lys Lys Arg
        50                  55

<210> SEQ ID NO 102
<211> LENGTH: 54
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Variable amino acid or not present
<220> FEATURE:
<221> NAME/KEY: MOD_RES
<222> LOCATION: (17)..(46)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 102

Pro Val Gln Pro Phe Leu Asn Leu Thr Thr Pro Arg Lys Pro Arg Xaa
1               5                   10                  15
```

```
Xaa Xaa Xaa Xaa Xaa Xaa Xaa Xaa Xaa Xaa Xaa Xaa Xaa
        20                  25                  30

Xaa Xaa Xaa Xaa Xaa Xaa Xaa Xaa Xaa Xaa Xaa Xaa Xaa Arg Arg
        35                  40                  45

Gln Arg Arg Lys Lys Arg
    50

<210> SEQ ID NO 103
<211> LENGTH: 53
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Variable amino acid or not present
<220> FEATURE:
<221> NAME/KEY: MOD_RES
<222> LOCATION: (16)..(45)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 103

Val Gln Pro Phe Leu Asn Leu Thr Thr Pro Arg Lys Pro Arg Xaa Xaa
1               5                  10                  15

Xaa Xaa Xaa Xaa Xaa Xaa Xaa Xaa Xaa Xaa Xaa Xaa Xaa Xaa
        20                  25                  30

Xaa Xaa Xaa Xaa Xaa Xaa Xaa Xaa Xaa Xaa Xaa Xaa Arg Arg Gln
        35                  40                  45

Arg Arg Lys Lys Arg
    50

<210> SEQ ID NO 104
<211> LENGTH: 57
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Variable amino acid or not present
<220> FEATURE:
<221> NAME/KEY: MOD_RES
<222> LOCATION: (20)..(49)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 104

Asp Gln Ser Arg Pro Val Gln Pro Phe Leu Asn Leu Thr Thr Pro Arg
1               5                  10                  15

Lys Pro Xaa Xaa Xaa Xaa Xaa Xaa Xaa Xaa Xaa Xaa Xaa Xaa Xaa
        20                  25                  30

Xaa Xaa Xaa Xaa Xaa Xaa Xaa Xaa Xaa Xaa Xaa Xaa Xaa Xaa
        35                  40                  45

Xaa Arg Arg Gln Arg Arg Lys Lys Arg
    50                  55
```

```
<210> SEQ ID NO 105
<211> LENGTH: 56
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Variable amino acid or not present
<220> FEATURE:
<221> NAME/KEY: MOD_RES
<222> LOCATION: (19)..(48)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 105

Asp Gln Ser Arg Pro Val Gln Pro Phe Leu Asn Leu Thr Thr Pro Arg
1               5                   10                  15

Lys Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa Xaa
            35                  40                  45

Arg Arg Gln Arg Arg Lys Lys Arg
    50                  55

<210> SEQ ID NO 106
<211> LENGTH: 55
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Variable amino acid or not present
<220> FEATURE:
<221> NAME/KEY: MOD_RES
<222> LOCATION: (18)..(47)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 106

Asp Gln Ser Arg Pro Val Gln Pro Phe Leu Asn Leu Thr Thr Pro Arg
1               5                   10                  15

Xaa Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa Arg
            35                  40                  45

Arg Gln Arg Arg Lys Lys Arg
    50                  55

<210> SEQ ID NO 107
<211> LENGTH: 54
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (16)..(16)
<223> OTHER INFORMATION: Variable amino acid or not present
<220> FEATURE:
<221> NAME/KEY: MOD_RES
<222> LOCATION: (17)..(46)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 107

Asp Gln Ser Arg Pro Val Gln Pro Phe Leu Asn Leu Thr Thr Pro Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Arg Arg
        35                  40                  45

Gln Arg Arg Lys Lys Arg
    50

<210> SEQ ID NO 108
<211> LENGTH: 53
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Variable amino acid or not present
<220> FEATURE:
<221> NAME/KEY: MOD_RES
<222> LOCATION: (16)..(45)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 108

Asp Gln Ser Arg Pro Val Gln Pro Phe Leu Asn Leu Thr Thr Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Arg Arg Gln
        35                  40                  45

Arg Arg Lys Lys Arg
    50

<210> SEQ ID NO 109
<211> LENGTH: 56
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Variable amino acid or not present
<220> FEATURE:
<221> NAME/KEY: MOD_RES
<222> LOCATION: (19)..(48)
<223> OTHER INFORMATION: Variable amino acid; region may or may not be
      present
<220> FEATURE:
```

<223> OTHER INFORMATION: See specification as filed for detailed
      description of substitutions and preferred embodiments

<400> SEQUENCE: 109

Gln Ser Arg Pro Val Gln Pro Phe Leu Asn Leu Thr Thr Pro Arg Lys
1               5                   10                  15

Pro Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Arg Arg Gln Arg Arg Lys Lys Arg
    50                  55

<210> SEQ ID NO 110
<211> LENGTH: 56
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Variable amino acid or not present
<220> FEATURE:
<221> NAME/KEY: MOD_RES
<222> LOCATION: (18)..(47)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 110

Ser Arg Pro Val Gln Pro Phe Leu Asn Leu Thr Thr Pro Arg Lys Pro
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Arg
        35                  40                  45

Arg Gln Arg Arg Lys Lys Arg Gly
    50                  55

<210> SEQ ID NO 111
<211> LENGTH: 55
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Variable amino acid or not present
<220> FEATURE:
<221> NAME/KEY: MOD_RES
<222> LOCATION: (17)..(46)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 111

Ser Arg Pro Val Gln Pro Phe Leu Asn Leu Thr Thr Pro Arg Lys Xaa
1               5                   10                  15

Xaa Xaa Xaa Xaa Xaa Xaa Xaa Xaa Xaa Xaa Xaa Xaa Xaa Xaa Xaa Xaa

```
                20              25                  30
Xaa Xaa Xaa Xaa Xaa Xaa Xaa Xaa Xaa Xaa Xaa Xaa Xaa Arg Arg
        35                  40                  45

Gln Arg Arg Lys Lys Arg Gly
    50                  55

<210> SEQ ID NO 112
<211> LENGTH: 55
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Variable amino acid or not present
<220> FEATURE:
<221> NAME/KEY: MOD_RES
<222> LOCATION: (17)..(46)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 112

Arg Pro Val Gln Pro Phe Leu Asn Leu Thr Thr Pro Arg Lys Pro Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Arg Arg
        35                  40                  45

Gln Arg Arg Lys Lys Arg Gly
    50                  55

<210> SEQ ID NO 113
<211> LENGTH: 54
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Variable amino acid or not present
<220> FEATURE:
<221> NAME/KEY: MOD_RES
<222> LOCATION: (16)..(45)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 113

Arg Pro Val Gln Pro Phe Leu Asn Leu Thr Thr Pro Arg Lys Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Arg Arg Gln
        35                  40                  45

Arg Arg Lys Lys Arg Gly
    50
```

```
<210> SEQ ID NO 114
<211> LENGTH: 51
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Variable amino acid or not present
<220> FEATURE:
<221> NAME/KEY: MOD_RES
<222> LOCATION: (13)..(42)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 114

Pro Val Gln Pro Phe Leu Asn Leu Thr Thr Pro Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Arg Arg Gln Arg Arg Lys
        35                  40                  45

Lys Arg Gly
    50

<210> SEQ ID NO 115
<211> LENGTH: 58
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Variable amino acid or not present
<220> FEATURE:
<221> NAME/KEY: MOD_RES
<222> LOCATION: (20)..(49)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 115

Gln Ser Arg Pro Val Gln Pro Phe Leu Asn Leu Thr Thr Pro Arg Lys
1               5                   10                  15

Pro Arg Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Arg Arg Gln Arg Arg Lys Lys Arg Gly
    50                  55

<210> SEQ ID NO 116
<211> LENGTH: 57
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (18)..(18)
<223> OTHER INFORMATION: Variable amino acid or not present
<220> FEATURE:
<221> NAME/KEY: MOD_RES
<222> LOCATION: (19)..(48)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 116

Ser Arg Pro Val Gln Pro Phe Leu Asn Leu Thr Thr Pro Arg Lys Pro
1               5                   10                  15

Arg Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Arg Arg Gln Arg Arg Lys Lys Arg Gly
    50                  55

<210> SEQ ID NO 117
<211> LENGTH: 56
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Variable amino acid or not present
<220> FEATURE:
<221> NAME/KEY: MOD_RES
<222> LOCATION: (18)..(47)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 117

Arg Pro Val Gln Pro Phe Leu Asn Leu Thr Thr Pro Arg Lys Pro Arg
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Arg
        35                  40                  45

Arg Gln Arg Arg Lys Lys Arg Gly
    50                  55

<210> SEQ ID NO 118
<211> LENGTH: 55
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Variable amino acid or not present
<220> FEATURE:
<221> NAME/KEY: MOD_RES
<222> LOCATION: (17)..(46)
<223> OTHER INFORMATION: Variable amino acid; region may or may not be
      present
<220> FEATURE:
<223> OTHER INFORMATION: See specification as filed for detailed
``` description of substitutions and preferred embodiments

<400> SEQUENCE: 118

Pro Val Gln Pro Phe Leu Asn Leu Thr Thr Pro Arg Lys Pro Arg Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Arg Arg
        35                  40                  45

Gln Arg Arg Lys Lys Arg Gly
    50                  55

<210> SEQ ID NO 119
<211> LENGTH: 54
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Variable amino acid or not present
<220> FEATURE:
<221> NAME/KEY: MOD_RES
<222> LOCATION: (16)..(45)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 119

Val Gln Pro Phe Leu Asn Leu Thr Thr Pro Arg Lys Pro Arg Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Arg Arg Gln
        35                  40                  45

Arg Arg Lys Lys Arg Gly
    50

<210> SEQ ID NO 120
<211> LENGTH: 58
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Variable amino acid or not present
<220> FEATURE:
<221> NAME/KEY: MOD_RES
<222> LOCATION: (20)..(49)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 120

Asp Gln Ser Arg Pro Val Gln Pro Phe Leu Asn Leu Thr Thr Pro Arg
1               5                   10                  15

Lys Pro Xaa Xaa Xaa Xaa Xaa Xaa Xaa Xaa Xaa Xaa Xaa Xaa Xaa Xaa
            20                  25                  30

```
Xaa Xaa Xaa Xaa Xaa Xaa Xaa Xaa Xaa Xaa Xaa Xaa Xaa Xaa
        35                  40                  45

Xaa Arg Gln Arg Arg Lys Lys Arg Gly
    50                  55

<210> SEQ ID NO 121
<211> LENGTH: 57
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Variable amino acid or not present
<220> FEATURE:
<221> NAME/KEY: MOD_RES
<222> LOCATION: (19)..(48)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 121

Asp Gln Ser Arg Pro Val Gln Pro Phe Leu Asn Leu Thr Thr Pro Arg
1               5                   10                  15

Lys Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Arg Arg Gln Arg Arg Lys Lys Arg Gly
    50                  55

<210> SEQ ID NO 122
<211> LENGTH: 56
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Variable amino acid or not present
<220> FEATURE:
<221> NAME/KEY: MOD_RES
<222> LOCATION: (18)..(47)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 122

Asp Gln Ser Arg Pro Val Gln Pro Phe Leu Asn Leu Thr Thr Pro Arg
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Arg
        35                  40                  45

Arg Gln Arg Arg Lys Lys Arg Gly
    50                  55

<210> SEQ ID NO 123
```

```
<211> LENGTH: 55
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Variable amino acid or not present
<220> FEATURE:
<221> NAME/KEY: MOD_RES
<222> LOCATION: (17)..(46)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 123

Asp Gln Ser Arg Pro Val Gln Pro Phe Leu Asn Leu Thr Thr Pro Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Arg Arg
        35                  40                  45

Gln Arg Arg Lys Lys Arg Gly
    50                  55

<210> SEQ ID NO 124
<211> LENGTH: 54
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Variable amino acid or not present
<220> FEATURE:
<221> NAME/KEY: MOD_RES
<222> LOCATION: (16)..(45)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 124

Asp Gln Ser Arg Pro Val Gln Pro Phe Leu Asn Leu Thr Thr Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Arg Arg Gln
        35                  40                  45

Arg Arg Lys Lys Arg Gly
    50

<210> SEQ ID NO 125
<211> LENGTH: 57
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
```

<223> OTHER INFORMATION: Variable amino acid or not present
<220> FEATURE:
<221> NAME/KEY: MOD_RES
<222> LOCATION: (19)..(48)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 125

Gln Ser Arg Pro Val Gln Pro Phe Leu Asn Leu Thr Thr Pro Arg Lys
1               5                   10                  15

Pro Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa Xaa
        35                  40                  45

Arg Arg Gln Arg Arg Lys Lys Arg Gly
    50                  55

<210> SEQ ID NO 126
<211> LENGTH: 56
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Variable amino acid or not present
<220> FEATURE:
<221> NAME/KEY: MOD_RES
<222> LOCATION: (18)..(47)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 126

Ser Arg Pro Val Gln Pro Phe Leu Asn Leu Thr Thr Pro Arg Lys Pro
1               5                   10                  15

Xaa Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa Arg
        35                  40                  45

Arg Gln Arg Arg Lys Lys Arg Gly
    50                  55

<210> SEQ ID NO 127
<211> LENGTH: 55
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Variable amino acid or not present
<220> FEATURE:
<221> NAME/KEY: MOD_RES
<222> LOCATION: (17)..(46)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 127

Ser Arg Pro Val Gln Pro Phe Leu Asn Leu Thr Thr Pro Arg Lys Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Arg Arg
        35                  40                  45

Gln Arg Arg Lys Lys Arg Gly
    50                  55

<210> SEQ ID NO 128
<211> LENGTH: 55
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Variable amino acid or not present
<220> FEATURE:
<221> NAME/KEY: MOD_RES
<222> LOCATION: (17)..(46)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 128

Arg Pro Val Gln Pro Phe Leu Asn Leu Thr Thr Pro Arg Lys Pro Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Arg Arg
        35                  40                  45

Gln Arg Arg Lys Lys Arg Gly
    50                  55

<210> SEQ ID NO 129
<211> LENGTH: 54
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Variable amino acid or not present
<220> FEATURE:
<221> NAME/KEY: MOD_RES
<222> LOCATION: (16)..(45)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 129

Arg Pro Val Gln Pro Phe Leu Asn Leu Thr Thr Pro Arg Lys Xaa Xaa
1               5                   10                  15

Xaa Xaa Xaa Xaa Xaa Xaa Xaa Xaa Xaa Xaa Xaa Xaa Xaa Xaa Xaa
            20                  25                  30

```
Xaa Xaa Xaa Xaa Xaa Xaa Xaa Xaa Xaa Xaa Xaa Arg Arg Gln
        35                  40                  45

Arg Arg Lys Lys Arg Gly
    50

<210> SEQ ID NO 130
<211> LENGTH: 51
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Variable amino acid or not present
<220> FEATURE:
<221> NAME/KEY: MOD_RES
<222> LOCATION: (13)..(42)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 130

Pro Val Gln Pro Phe Leu Asn Leu Thr Thr Pro Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Arg Arg Gln Arg Arg Lys
        35                  40                  45

Lys Arg Gly
    50

<210> SEQ ID NO 131
<211> LENGTH: 57
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Variable amino acid or not present
<220> FEATURE:
<221> NAME/KEY: MOD_RES
<222> LOCATION: (20)..(49)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 131

Gln Ser Arg Pro Val Gln Pro Phe Leu Asn Leu Thr Thr Pro Arg Lys
1               5                   10                  15

Pro Arg Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Arg Gln Arg Arg Lys Lys Arg Gly
    50                  55

<210> SEQ ID NO 132
<211> LENGTH: 56
```

<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Variable amino acid or not present
<220> FEATURE:
<221> NAME/KEY: MOD_RES
<222> LOCATION: (19)..(48)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 132

Ser Arg Pro Val Gln Pro Phe Leu Asn Leu Thr Thr Pro Arg Lys Pro
1               5                   10                  15

Arg Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Arg Gln Arg Arg Lys Lys Arg Gly
    50                  55

<210> SEQ ID NO 133
<211> LENGTH: 55
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Variable amino acid or not present
<220> FEATURE:
<221> NAME/KEY: MOD_RES
<222> LOCATION: (18)..(47)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 133

Arg Pro Val Gln Pro Phe Leu Asn Leu Thr Thr Pro Arg Lys Pro Arg
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Arg
        35                  40                  45

Gln Arg Arg Lys Lys Arg Gly
    50                  55

<210> SEQ ID NO 134
<211> LENGTH: 54
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Variable amino acid or not present

```
-continued

<220> FEATURE:
<221> NAME/KEY: MOD_RES
<222> LOCATION: (17)..(46)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 134

Pro Val Gln Pro Phe Leu Asn Leu Thr Thr Pro Arg Lys Pro Arg Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Arg Gln
        35                  40                  45

Arg Arg Lys Lys Arg Gly
    50

<210> SEQ ID NO 135
<211> LENGTH: 53
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Variable amino acid or not present
<220> FEATURE:
<221> NAME/KEY: MOD_RES
<222> LOCATION: (16)..(45)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 135

Val Gln Pro Phe Leu Asn Leu Thr Thr Pro Arg Lys Pro Arg Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Arg Gln Arg
        35                  40                  45

Arg Lys Lys Arg Gly
    50

<210> SEQ ID NO 136
<211> LENGTH: 57
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Variable amino acid or not present
<220> FEATURE:
<221> NAME/KEY: MOD_RES
<222> LOCATION: (20)..(49)
<223> OTHER INFORMATION: Variable amino acid; region may or may not be
      present
<220> FEATURE:
<223> OTHER INFORMATION: See specification as filed for detailed
      description of substitutions and preferred embodiments
```

<400> SEQUENCE: 136

Asp Gln Ser Arg Pro Val Gln Pro Phe Leu Asn Leu Thr Thr Pro Arg
1               5                   10                  15

Lys Pro Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa Xaa
            35                  40                  45

Xaa Arg Gln Arg Arg Lys Lys Arg Gly
    50                  55

<210> SEQ ID NO 137
<211> LENGTH: 56
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Variable amino acid or not present
<220> FEATURE:
<221> NAME/KEY: MOD_RES
<222> LOCATION: (19)..(48)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 137

Asp Gln Ser Arg Pro Val Gln Pro Phe Leu Asn Leu Thr Thr Pro Arg
1               5                   10                  15

Lys Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa Xaa
            35                  40                  45

Arg Gln Arg Arg Lys Lys Arg Gly
    50                  55

<210> SEQ ID NO 138
<211> LENGTH: 55
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Variable amino acid or not present
<220> FEATURE:
<221> NAME/KEY: MOD_RES
<222> LOCATION: (18)..(47)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 138

Asp Gln Ser Arg Pro Val Gln Pro Phe Leu Asn Leu Thr Thr Pro Arg
1               5                   10                  15

Xaa Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa Arg

```
                35                  40                  45

Gln Arg Arg Lys Lys Arg Gly
    50                  55

<210> SEQ ID NO 139
<211> LENGTH: 54
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Variable amino acid or not present
<220> FEATURE:
<221> NAME/KEY: MOD_RES
<222> LOCATION: (17)..(46)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 139

Asp Gln Ser Arg Pro Val Gln Pro Phe Leu Asn Leu Thr Thr Pro Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Arg Gln
        35                  40                  45

Arg Arg Lys Lys Arg Gly
    50

<210> SEQ ID NO 140
<211> LENGTH: 53
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Variable amino acid or not present
<220> FEATURE:
<221> NAME/KEY: MOD_RES
<222> LOCATION: (16)..(45)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 140

Asp Gln Ser Arg Pro Val Gln Pro Phe Leu Asn Leu Thr Thr Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Arg Gln Arg
        35                  40                  45

Arg Lys Lys Arg Gly
    50

<210> SEQ ID NO 141
<211> LENGTH: 56
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Variable amino acid or not present
<220> FEATURE:
<221> NAME/KEY: MOD_RES
<222> LOCATION: (19)..(48)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 141

Gln Ser Arg Pro Val Gln Pro Phe Leu Asn Leu Thr Thr Pro Arg Lys
1               5                   10                  15

Pro Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa Xaa
            35                  40                  45

Arg Gln Arg Arg Lys Lys Arg Gly
    50                  55

<210> SEQ ID NO 142
<211> LENGTH: 55
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Variable amino acid or not present
<220> FEATURE:
<221> NAME/KEY: MOD_RES
<222> LOCATION: (18)..(47)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 142

Ser Arg Pro Val Gln Pro Phe Leu Asn Leu Thr Thr Pro Arg Lys Pro
1               5                   10                  15

Xaa Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa Arg
            35                  40                  45

Gln Arg Arg Lys Lys Arg Gly
    50                  55

<210> SEQ ID NO 143
<211> LENGTH: 54
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Variable amino acid or not present
<220> FEATURE:
```

```
<221> NAME/KEY: MOD_RES
<222> LOCATION: (17)..(46)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 143

Ser Arg Pro Val Gln Pro Phe Leu Asn Leu Thr Thr Pro Arg Lys Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Arg Gln
        35                  40                  45

Arg Arg Lys Lys Arg Gly
    50

<210> SEQ ID NO 144
<211> LENGTH: 54
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Variable amino acid or not present
<220> FEATURE:
<221> NAME/KEY: MOD_RES
<222> LOCATION: (17)..(46)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 144

Arg Pro Val Gln Pro Phe Leu Asn Leu Thr Thr Pro Arg Lys Pro Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Arg Gln
        35                  40                  45

Arg Arg Lys Lys Arg Gly
    50

<210> SEQ ID NO 145
<211> LENGTH: 53
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Variable amino acid or not present
<220> FEATURE:
<221> NAME/KEY: MOD_RES
<222> LOCATION: (16)..(45)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 145
```

```
Arg Pro Val Gln Pro Phe Leu Asn Leu Thr Thr Pro Arg Lys Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Arg Gln Arg
        35                  40                  45

Arg Lys Lys Arg Gly
        50
```

<210> SEQ ID NO 146
<211> LENGTH: 50
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Variable amino acid or not present
<220> FEATURE:
<221> NAME/KEY: MOD_RES
<222> LOCATION: (13)..(42)
<223> OTHER INFORMATION: Variable amino acid; region may or may not be
      present
<220> FEATURE:
<223> OTHER INFORMATION: See specification as filed for detailed
      description of substitutions and preferred embodiments

<400> SEQUENCE: 146

```
Pro Val Gln Pro Phe Leu Asn Leu Thr Thr Pro Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Arg Gln Arg Arg Lys Lys
        35                  40                  45

Arg Gly
    50
```

<210> SEQ ID NO 147
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Variable amino acid
<220> FEATURE:
<221> NAME/KEY: MOD_RES
<222> LOCATION: (7)..(7)
<223> OTHER INFORMATION: Variable amino acid
<220> FEATURE:
<221> NAME/KEY: MOD_RES
<222> LOCATION: (9)..(15)
<223> OTHER INFORMATION: Variable amino acid
<220> FEATURE:
<221> NAME/KEY: MOD_RES
<222> LOCATION: (18)..(18)
<223> OTHER INFORMATION: Variable amino acid

<400> SEQUENCE: 147

```
Xaa Arg Pro Thr Thr Leu Xaa Leu Xaa Xaa Xaa Xaa Xaa Xaa Xaa Gln
1               5                   10                  15

Asp Xaa
```

<210> SEQ ID NO 148
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Variable amino acid
<220> FEATURE:
<221> NAME/KEY: MOD_RES
<222> LOCATION: (4)..(10)
<223> OTHER INFORMATION: Variable amino acid
<220> FEATURE:
<221> NAME/KEY: MOD_RES
<222> LOCATION: (12)..(12)
<223> OTHER INFORMATION: Variable amino acid
<220> FEATURE:
<221> NAME/KEY: MOD_RES
<222> LOCATION: (18)..(18)
<223> OTHER INFORMATION: Variable amino acid

<400> SEQUENCE: 148

Xaa Asp Gln Xaa Xaa Xaa Xaa Xaa Xaa Xaa Leu Xaa Leu Thr Thr Pro
1               5                   10                  15

Arg Xaa

<210> SEQ ID NO 149
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(7)
<223> OTHER INFORMATION: Variable amino acid
<220> FEATURE:
<221> NAME/KEY: MOD_RES
<222> LOCATION: (17)..(21)
<223> OTHER INFORMATION: Variable amino acid
<220> FEATURE:
<221> NAME/KEY: MOD_RES
<222> LOCATION: (27)..(27)
<223> OTHER INFORMATION: Variable amino acid
<220> FEATURE:
<221> NAME/KEY: MOD_RES
<222> LOCATION: (29)..(35)
<223> OTHER INFORMATION: Variable amino acid
<220> FEATURE:
<221> NAME/KEY: MOD_RES
<222> LOCATION: (38)..(38)
<223> OTHER INFORMATION: Variable amino acid

<400> SEQUENCE: 149

Xaa Xaa Xaa Xaa Xaa Xaa Xaa Arg Lys Lys Arg Arg Gln Arg Arg Arg
1               5                   10                  15

Xaa Xaa Xaa Xaa Xaa Arg Pro Thr Thr Leu Xaa Leu Xaa Xaa Xaa Xaa
            20                  25                  30

Xaa Xaa Xaa Gln Asp Xaa
        35

<210> SEQ ID NO 150
<211> LENGTH: 38
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Variable amino acid
<220> FEATURE:
<221> NAME/KEY: MOD_RES
<222> LOCATION: (4)..(10)
<223> OTHER INFORMATION: Variable amino acid
<220> FEATURE:
<221> NAME/KEY: MOD_RES
<222> LOCATION: (12)..(12)
<223> OTHER INFORMATION: Variable amino acid
<220> FEATURE:
<221> NAME/KEY: MOD_RES
<222> LOCATION: (18)..(22)
<223> OTHER INFORMATION: Variable amino acid
<220> FEATURE:
<221> NAME/KEY: MOD_RES
<222> LOCATION: (32)..(38)
<223> OTHER INFORMATION: Variable amino acid

<400> SEQUENCE: 150

Xaa Asp Gln Xaa Xaa Xaa Xaa Xaa Xaa Xaa Leu Xaa Leu Thr Thr Pro
1               5                   10                  15

Arg Xaa Xaa Xaa Xaa Xaa Arg Arg Arg Gln Arg Arg Lys Lys Arg Xaa
            20                  25                  30

Xaa Xaa Xaa Xaa Xaa Xaa
        35
```

CELL-PERMEABLE PEPTIDE INHIBITORS OF THE JNK SIGNAL TRANSDUCTION PATHWAY

SEQUENCE LISTING INFORMATION

A computer readable text file, entitled "067802-5016-01-SequenceListing.txt" created on or about March 24,2014, with a file size of about 118kb contains the sequence listing for this application and is hereby incorporated by reference in its entirety.

The present invention refers to protein kinase inhibitors and more specifically to inhibitors of the protein kinase c-Jun amino terminal kinase. Additionally, the present invention provides JNK inhibitor sequences, chimeric peptides, nucleic acids encoding same as well as pharmaceutical compositions for treating pathophysiologies associated with JNK signaling.

The c-Jun amino terminal kinase (JNK) is a member of the stress-activated group of mitogen-activated protein (MAP) kinases. These kinases have been implicated in the control of cell growth and differentiation, and, more generally, in the response of cells to environmental stimuli. The JNK signal transduction pathway is activated in response to environmental stress and by the engagement of several classes of cell surface receptors. These receptors can include cytokine receptors, serpentine receptors and receptor tyrosine kinases. In mammalian cells, JNK has been implicated in biological processes such as oncogenic transformation and mediating adaptive responses to environmental stress. JNK has also been associated with modulating immune responses, including maturation and differentiation of immune cells, as well effecting programmed cell death in cells identified for destruction by the immune system. This unique property makes JNK signaling a promising target for developing pharmacological intervention. Among several neurological disorders, JNK signaling is particularly implicated in ischemic stroke and Parkinson's disease.

One approach in combating disorders strongly related to JNK signaling is the provision of inhibitors of the JNK signaling pathway. Such inhibitors as already known in the prior art particularly include e.g. upstream kinase inhibitors (for example, CEP-1347), small chemical inhibitors of JNK (SP600125and AS601245), which directly affect kinase activity e.g. by competing with the ATP-binding site of the protein kinase, and peptide inhibitors of the interaction between JNK and its substrates (D-JNKI and I-JIP) (see e.g. Kuan et al., Current Drug Targets—CNS & Neurological Disorders, February 2005, vol. 4, no. 1, pp. 63-67(5)).

The upstream kinase inhibitor CEP-1347(KT7515) is a semisynthetic inhibitor of the mixed lineage kinase family. CEP-1347(KT7515) promotes neuronal survival at dosages that inhibit activation of the c-Jun amino-terminal kinases (JNKs) in primary embryonic cultures and differentiated PC12 cells after trophic withdrawal and in mice treated with 1-methyl-4-phenyl tetrahydropyridine. Further, CEP-1347 (KT7515) can promote long term-survival of cultured chick embryonic dorsal root ganglion, sympathetic, ciliary and motor neurons (see e.g. Borasio et al., Neuroreport. 9(7): 1435-1439, May 11, 1998.).

The small chemical JNK inhibitor SP600125was found to reduce the levels of c-Jun phosphorylation, to protect dopaminergic neurons from apoptosis, and to partly restore the level of dopamine in MPTP-induced PD in C57BL/6N mice (Wang et al., Neurosci Res. 2004February; 48(2); 195-202). These results furthermore indicate that JNK pathway is the major mediator of the neurotoxic effects of MPTP in vivo and inhibiting JNK activity may represent a new and effective strategy to treat PD.

A further example of small chemical inhibitors is the aforementioned JNK-Inhibitor AS601245. AS601245inhibits the JNK signalling pathway and promotes cell survival after cerebral ischemia. In vivo, AS601245provided significant protection against the delayed loss of hippocampal CA1 neurons in a gerbil model of transient global ischemia. This effect is mediated by JNK inhibition and therefore by c-Jun expression and phosphorylation (see e.g. Carboni et al., J Pharmacol Exp Ther. 2004July; 310(1):25-32. Epub 2004 Feb. 26).

A third class of inhibitors of the JNK signaling pathway represent peptide inhibitors of the interaction between JNK and its substrates, as mentioned above. As a starting point for construction of such JNK inhibitor peptides a sequence alignment of naturally occurring JNK proteins may be used. Typically, these proteins comprise JNK binding domains (JBDs) and occur in various insulin binding (IB) proteins, such as IB1 or IB2. The results of such an exemplary sequence alignment is e.g. a sequence alignment between the JNK binding domains of IB1[SEQ ID NO: 13], IB2 [SEQ ID NO: 14], c-Jun [SEQ ID NO: 15] and ATF2 [SEQ ID NO: 16] (see e.g. FIGS. 1A-1C). Such an alignment reveals a partially conserved 8amino acid sequence (see e.g. FIG. 1A). A comparison of the JBDs of IB1 and IB2further reveals two blocks of seven and three amino acids that are highly conserved between the two sequences.

Sequences constructed on basis of such an alignment are e.g. disclosed in WO 01/27268. Particularly, WO 01/27268discloses small cell permeable fusion peptides, comprising a so-called TAT cell permeation sequence derived from the basic trafficking sequence of the HIV-TAT protein and a minimum 20amino acid inhibitory sequence of IB1. Both components are covalently linked to each other. Exemplary (and at present the only) inhibitors of the MAPK-JNK signaling pathway disclosed in WO 01/27268, are e.g. L-JNKI1(JNK-inhibitor peptide composed of L amino acids) or the protease resistant D-JNKI1 peptides (JNK-inhibitor peptide composed of non-native D amino acids). These JNK-inhibitor (JNKI) peptides are specific for JNK (JNK1, JNK2 and JNK3). In contrast to those small compound inhibitors as discussed above, the inhibitor sequences in WO 01/27268, e.g. JNKI1, rather inhibit the interaction between JNK and its substrate. By its trafficking sequence derived from TAT, the fusion peptide is efficiently transported into cells. Due to the novel properties obtained by the trafficking component the fusion peptides are actively transported into cells, where they remain effective until proteolytic degradation.

However, peptides according to WO 01/27268are still easily accessible by phosphorylases (kinases). Any amino acid of a peptide serving as a target for kinases and, therefore, may be subjected to phosphorylation, represents an important factor for inactivating such peptides. Therefore, it is a first object of the present invention to provide novel inhibitor sequences for the JNK signaling pathway, which retain the functional properties of the peptides as disclosed in WO 01/27268but provide enhanced stability towards phosphorylases (kinases).

Furthermore, inhibitor sequences according to WO 01/27268require an expensive recovery and purification step, particularly if prepared in large scale amounts (e.g. for industrial production). Thus, it is a second object of the present invention to provide inhibitor sequences which allow easier and more cost efficient production and recovery than those of the state of the art.

These objects are solved by a JNK inhibitor sequence comprising less than 150amino acids in length, wherein the JNK inhibitor sequence comprises or consists of at least one amino acid sequence according to SEQ ID NOs: 1, 2, 3 or 4, or a variant, fragment or derivative thereof.

Preferably, the inventive JNK inhibitor sequence binds JNK and/or inhibits the activation of at least one JNK activated transcription factor, e.g. c-Jun or ATF2 (see e.g. SEQ ID NOs: 15 and 16, respectively) or Elk1.

Typically, JNK inhibitor sequences according to the present invention comprise a total length of less than 150 amino acid residues, preferably a range of 5 to 150 amino acid residues, more preferably 10 to 100 amino acid residues, even more preferably 10 to 75 amino acid residues and most preferably a range of 15 to 50 amino acid residues.

The inventive JNK inhibitor sequence preferably contains or consists of at least one amino acid sequence according to SEQ ID NOs: 1, 2, 3 or 4, or a fragment, derivative or variant thereof. More preferably, the inventive JNK inhibitor sequence may contain 1, 2, 3, 4 or even more copies of an amino acid sequence according to SEQ ID NOs: 1, 2, 3 or 4, or a variant, fragment or derivative thereof. If present in more than one copy, these inventive amino acid sequences according to SEQ ID NOs: 1, 2, 3 or 4, or variants, fragments, or derivatives thereof may be directly linked with each other without any linker sequence or via a linker sequence comprising 1 to 10, preferably 1 to 5 amino acids. Amino acids forming the linker sequence are preferably selected from glycine or proline as amino acid residues. More preferably, these inventive amino acid sequences according to SEQ ID NOs: 1, 2, 3 or 4, or fragments, variants or derivatives thereof, may be separated by each other by a hinge of two, three or more proline residues.

The inventive JNK inhibitor sequences as defined above may be composed of L-amino acids, D-amino acids, or a combination of both. Preferably, the inventive JNK inhibitor sequences comprise at least 1, preferably at least 3, more preferably at least 6 and even more preferably at least 10 D- and/or L-amino acids, wherein the D- and/or L-amino acids may be arranged in the inventive JNK inhibitor sequences in a blockwise, a non-blockwise or in an alternate manner.

According to one preferred embodiment the inventive JNK inhibitor sequences may be exclusively composed of L-amino acids. The inventive JNK inhibitor sequences may then comprise or consist of at least one "native JNK inhibitor sequence" according to SEQ ID NO: 1 or 3. In this context, the term "native" or "native JNK inhibitor sequence(s)" is referred to non-altered inventive JNK inhibitor sequences according to any of SEQ ID NOs: 1 or 3, entirely composed of L-amino acids.

Accordingly, the inventive JNK inhibitor sequence may comprise or consist of at least one (native) amino acid sequence NH$_2$-X$_n^b$-X$_n^a$-RPTTLXLXXXXXXXQD-X$_n^b$-COOH [SEQ ID NO: 3]. As used in this context, each X represents an amino acid residue, preferably selected from any (native) amino acid residue. X$_n^a$ represents one amino acid residue, preferably selected from any amino acid residue except serine or threonine, wherein n is 0 or 1. Furthermore, each X$_n^b$ may be selected from any amino acid residue, wherein n is 0-5, 5-10, 10-15, 15-20, 20-30 or more, provided that if n is 0 for X$_n^a$, X$_n^b$ must not comprise a serine or threonine at its C-terminus, in order to avoid a serine or threonine at this position. Preferably, X$_n^b$ represents a contiguous stretch of peptide residues derived from SEQ ID NO: 1 or 3. More preferably, the inventive JNK inhibitor sequence further may comprise or consist of at least one (native) amino acid sequence NH$_2$-RPKRPTTLNLFPQVPRSQD-COOH [SEQ ID NO: 1]. X$_n^a$ and X$_n^b$ represent either D or L amino acids.

According to another preferred embodiment the inventive JNK inhibitor sequences may be composed in part or exclusively of D-amino acids. More preferably, these inventive JNK inhibitor sequences composed of D-amino acids are non-native D retro-inverso sequences of the above (native) JNK inhibitor sequences. The term "retro-inverso sequences" refers to an isomer of a linear peptide sequence in which the direction of the sequence is reversed and the chirality of each amino acid residue is inverted (see e.g. Jameson et al., Nature, 368, 744-746 (1994); Brady et al., Nature, 368, 692-693 (1994)). The advantage of combining D-enantiomers and reverse synthesis is that the positions of carbonyl and amino groups in each amide bond are exchanged, while the position of the side-chain groups at each alpha carbon is preserved. Unless specifically stated otherwise, it is presumed that any given L-amino acid sequence or peptide according to the present invention may be converted into an D retro-inverso sequence or peptide by synthesizing a reverse of the sequence or peptide for the corresponding native L-amino acid sequence or peptide.

The inventive D retro-inverso sequences as defined above have a variety of useful properties. For example, inventive D retro-inverso sequences enter cells as efficiently as L-amino acid sequences according to the present invention, whereas the inventive D retro-inverso sequences are more stable than the corresponding L-amino acid sequences.

Accordingly, the inventive JNK inhibitor sequences may comprise or consist of at least one D retro-inverso sequence according to the amino acid sequence NH$_2$-X$_n^b$-DQXXXXXXXLXLTTPR-X$_n^a$-X$_n^b$-COOH [SEQ ID NO: 4]. As used in this context, X, X$_n^a$ and X$_n^b$ are as defined above (preferably, representing D amino acids), wherein X$_n^b$ preferably represents a contiguous stretch of residues derived from SEQ ID NO: 2 or 4. More preferably, the inventive JNK inhibitor sequences may comprise or consist of at least one D retro-inverso sequence according to the amino acid sequence NH$_2$-DQSRPVQPFLNLTTPRKPR-COOH [SEQ ID NO: 2].

The inventive JNK inhibitor sequences as disclosed above are presented in Table 1 (SEQ ID NOs: 1-4). The table presents the name of the inventive JNK inhibitor sequences, as well as their sequence identifier number, their length, and amino acid sequence. Additionally, prior art sequences according to WO 01/27268 (SEQ ID NOs: 17-26) are also given for comparative reasons. These prior art sequences are not disclosed herein as inventive JNK inhibitor sequences or inventive chimeric peptides and are therefore explicitly excluded from the scope of the present invention by way of a disclaimer.

TABLE 1

| SEQUENCE/PEPTIDE NAME | SEQ ID NO | AA | SEQUENCE |
|---|---|---|---|
| L-IB1 (s) | 1 | 19 | RPKRPTTLNL FPQVPRSQD (NH$_2$-RPKRPTTLNLFPQVPRSQD-COOH) |
| D-IB1 (s) | 2 | 19 | DQSRPVQPFL NLTTPRKPR (NH$_2$-DQSRPVQPFLNLTTPRKPR-COOH) |

TABLE 1 -continued

| SEQUENCE/PEPTIDE NAME | SEQ ID NO | AA | SEQUENCE |
|---|---|---|---|
| L-IB (generic) (s) | 147 and 3, respectively | 18 | XRPTTLXLXX XXXXXQDX  (NH$_2$-X$_n^b$-X$_n^a$-RPTTLXLXXXXXXXQD-X$_n^b$-COOH) |
| D-IB (generic) (s) | 148 and 4, respectively | 18 | XDQXXXXXXX LXLTTPRX  (NH$_2$-X$_n^b$-DQXXXXXXXLXLTTPR-X$_n^a$-X$_n^b$-COOH) |
| L-TAT | 5 | 10 | GRKKRRQRRR  (NH$_2$-GRKKRRQRRR-COOH) |
| D-TAT | 6 | 10 | RRRQRRKKRG  (NH$_2$-RRRQRRKKRG-COOH) |
| L-generic-TAT (s) | 21 and 7, respectively | 17 | XXXXRKKRRQ RRRXXXX  (NH$_2$-X$_n^b$-RKKRRQRRR-X$_n^b$-COOH) |
| D-generic-TAT (s) | 22 and 8, respectively | 17 | XXXXRRRQRR KKRXXXX  (NH$_2$-X$_n^b$-RRRQRRKKR-X$_n^b$-COON) |
| L-TAT-IB1 (s) | 9 | 31 | GRKKRRQRRR PPRPKRPTTL NLFPQVPRSQ D  (NH$_2$-GRKKRRQRRRPPRPKRPTTLNLFPQVPRSQD-COOH) |
| L-TAT-IB (generic) (s) | 149 and 10, respectively | 38 | XXXXXXXXRKK RRQRRRXXXX XRPTTLXLXX XXXXXQDX  (NH$_2$-X$_n^b$-RKKRRQRRR-X$_n^b$-X$_n^a$-RPTTLXLXXXXXXXQD-X$_n^b$-COOH ) |
| D-TAT-IB1 (s) | 11 | 31 | DQSRPVQPFL NLTTPRKPRP PRRRQRRKKR G  (NH$_2$-DQSRPVQPFLNLTTPRKPRPPRRRQRRKKRG-COOH) |
| D-TAT-IB (generic) (s) | 150 and 12, respectively | 38 | XDQXXXXXXX LXLTTPRXXX XXRRRQRRKK RXXXXXXX  (NH$_2$-X$_n^b$-DQXXXXXXXLXLTTPR-X$_n^a$-X$_n^b$-RRRQRRKKR-X$_n^b$-COOH ) |
| IB1-long | 13 | 29 | PGTGCGDTYR PKRPTTLNLF PQVPRSQDT |
| IB2-long | 14 | 27 | IPSPSVEEPH KHRPTTLRLT TLGAQDS |
| c-Jun | 15 | 29 | GAYGYSNPKI LKQSMTLNLA DPVGNLKPH |
| ATF2 | 16 | 29 | TNEDHLAVHK HKHEMTLKFG PARNDSVIV |
| L-IB1 | 17 | 23 | DTYRPKRPTT LNLFPQVPRS QDT |
| D-IB1 | 18 | 23 | TDQSRPVQPF LNLTTPRKPR YTD |
| L-IB (generic) | 19 | 19 | XRPTTLXLXX XXXXXQDS/TX |
| D-IB (generic) | 20 | 19 | XS/TDQXXXXXX XLXLTTPRX |
| L-generic-TAT | 21 | 17 | XXXXRKKRRQ RRRXXXX |
| D-generic-TAT | 22 | 17 | XXXXRRRQRR KKRXXXX |
| L-TAT-IB1 | 23 | 35 | GRKKRRQRRR PPDTYRPKRP TTLNLFPQVP RSQDT |
| L-TAT-IB (generic) | 24 | 42 | XXXXXXXXRKK RRQRRRXXXX XXXXRPTTLX LXXXXXXXQD S/TX |
| D-TAT-IB1 | 25 | 35 | TDQSRPVQPF LNLTTPRKPR YTDPPRRRQR RKKRG |
| D-TAT-IB (generic) | 26 | 42 | XT/SDQXXXXXX XLXLTTPRXX XXXXXXRRRQ RRKKRXXXX XX |

(In Table 1 exemplary sequences as well as their generic formulas are shown for SEQ ID NO's: 1, 2, 5, 6, 9 and 11 and SEQ ID NO's: 3, 4, 7, 8, 10 and 12, respectively).

According to another preferred embodiment, the inventive JNK inhibitor sequence comprises or consists of at least one variant, fragment and/or derivative of the above defined inventive native or non-native amino acid sequences according to SEQ ID NOs: 1, 2, 3 or 4. Preferably, these variants, fragments and/or derivatives retain biological activity of the above disclosed inventive native or non-native JNK inhibitor sequences, particularly of native or non-native amino acid sequences according to SEQ ID NOs: 1, 2, 3 or 4, i.e. binding JNK and/or inhibiting the activation of at least one JNK activated transcription factor, e.g. c-Jun, ATF2 or Elk1. Functionality may be tested by various tests, e.g. binding tests of the peptide to its target molecule or by biophysical methods, e.g. spectroscopy, computer modeling, structural analysis, etc. Particularly, an inventive JNK inhibitor sequence or variants, fragments and derivatives thereof may be analyzed by hydrophilicity analysis (see e.g. Hopp and Woods, 1981. Proc Natl Acad Sci USA 78: 3824-3828) that can be utilized to identify the hydrophobic and hydrophilic regions of the peptides, thus aiding in the design of substrates for experimental manipulation, such as in binding experiments, or for antibody synthesis. Secondary structural analysis may also be performed to identify regions of an (inventive) JNK inhibitor sequence or of variants, fragments and/or derivatives thereof that assume specific structural motifs (see e.g. Chou and Fasman, 1974, Biochem 13: 222-223). Manipulation, translation, secondary structure prediction, hydrophilicity and hydrophobicity profiles, open reading frame prediction and plotting, and determination of sequence homologies can be accomplished using computer software programs available in the art. Other methods of structural analysis include, e.g. X-ray crystallography (see e.g. Engstrom, 1974. Biochem Exp Biol 11: 7-13), mass spectroscopy and gas chromatography (see e.g. METHODS IN PROTEIN SCIENCE, 1997, J. Wiley and Sons, New York, N.Y.) and computer modeling (see e.g. Fletterick and Zoller, eds., 1986. Computer Graphics and Molecular Modeling, In: CURRENT COMMUNICATIONS IN MOLECULAR BIOLOGY, Cold Spring Harbor Laboratory Press, Cold Spring Harbor, N.Y.) may also be employed.

Accordingly, the inventive JNK inhibitor sequence may comprise or consist of at least one variant of (native or non-native) amino acid sequences according to SEQ ID NOs: 1, 2, 3 or 4. In the context of the present invention, a "variant of a (native or non-native) amino acid sequence according to SEQ ID NOs: 1, 2, 3 or 4" is preferably a sequence derived from any of the sequences according to SEQ ID NOs: 1, 2, 3 or 4, wherein the variant comprises amino acid alterations of the amino acid sequences according to SEQ ID NOs: 1, 2, 3 or 4. Such alterations typically comprise 1 to 20, preferably 1 to 10 and more preferably 1 to 5 substitutions, additions and/or deletions of amino acids according to SEQ ID NOs: 1, 2, 3 or 4, wherein the variant exhibits a sequence identity with any of the sequences according to SEQ ID NOs: 1, 2, 3 or 4 of at least about 30%, 50%, 70%, 80%, 90%, 95%, 98% or even 99%.

If variants of inventive (native or non-native) amino acid sequences according to SEQ ID NOs: 1, 2, 3 or 4 are obtained by substitution of specific amino acids, such substitutions preferably comprise conservative amino acid substitutions. Conservative amino acid substitutions may include synonymous amino acid residues within a group which have sufficiently similar physicochemical properties, so that a substitution between members of the group will preserve the biological activity of the molecule (see e.g. Grantham, R. (1974), Science 185, 862-864). It is evident to the skilled person that amino acids may also be inserted and/or deleted in the above-defined sequences without altering their function, particularly if the insertions and/or deletions only involve a few amino acids, e.g. less than twenty, and preferably less than ten, and do not remove or displace amino acids which are critical to functional activity. Moreover, substitutions shall be avoided in inventive variants, which lead to additional threonines at amino acid positions which are accessible for a phosphorylase, preferably a kinase, in order to avoid inactivation of the inventive JNK-inhibitor sequence or of the inventive chimeric peptide in vivo or in vitro.

Preferably, synonymous amino acid residues, which are classified into the same groups and are typically exchangeable by conservative amino acid substitutions, are defined in Table 2.

TABLE 2

Preferred Groups of Synonymous Amino Acid Residues

| Amino Acid | Synonymous Residue |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, (Thr), Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, (Thr), Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, (Thr), Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

A specific form of a variant of SEQ ID NOs: 1, 2, 3 or 4 according to the invention is a fragment of the inventive (native or non-native) amino acid sequences according to SEQ ID NOs: 1,2,3 or 4", which is typically altered by at least one deletion as compared to SEQ ID NOs 1,2,3 or 4. Preferably, a fragment comprises at least 4 contiguous amino acids of any of SEQ ID NOs: 1 2,3 or 4, a length typically sufficient to allow for specific recognition of an epitope from any of these sequences. Even more preferably, the fragment comprises 4 to 18, 4 to 15, or most preferably 4 to 10 contiguous amino acids of any of SEQ ID NOs: 1,2,3 or 4. Deleted amino acids may occur at any position of SEQ ID NOs: 1, 2,3 or 4, preferably N- or C-terminally. In particular, peptides of SEQ ID NO: 2 (DQSRPVQPFLNLTTPRKPR) may be deleted at its N- and/or C-terminus by 1,2,3,4, or 5 amino acids. In other words, preferred shorter versions of SEQ ID NO: 2 may have the sequence QSRPVQPFLNLTTPRKPR (SEQ ID NO: 28), SRPVQPFLNLTTPRKPR (SEQ ID NO: 29), RPVQPFLNLTTPRKPR (SEQ ID NO: 30), PVQPFLNLTTPRKPR (SEQ ID NO: 31), or VQPFLNLTTPRKPR (SEQ ID NO: 32) or, respectively, DQSRPVQPFLNLTTPRKP (SEQ ID NO: 33), DQSRPVQPFLNLTTPRK (SEQ ID NO: 34), DQSRPVQPFLNLTTPR (SEQ ID NO: 35), DQSRPVQPFLNLTTP (SEQ ID NO: 36), DQSRPVQPFLNLTT (SEQ ID NO: 37), or QSRPVQPFLNLTTPRKP (SEQ ID NO: 38), SRPVQPFLNLTTPRKP (SEQ ID NO: 39), SRPVQPFLNLTTPRK (SEQ ID NO: 40), RPVQPFLNLTTPRKP (SEQ ID NO: 41), RPVQPFLNLTTPRK (SEQ ID NO: 42) or PVQPFLNLTTP (SEQ ID NO: 43). The shorter the inventive peptide sequence used, the lower its unspecific cell toxicity. In certain embodiments, the peptides used shall have the shortest sequence possible, which still retains the biological function, e.g. the JNK inhibitory function.

Furthermore, a fragment of the inventive (native or non-native) amino acid sequences according to SEQ ID NOs: 1, 2, 3 or 4 may be defined as a sequence sharing a sequence identity with any of the sequences according to SEQ ID NOs: 1, 2, 3 or 4 of at least about 30%, 50%, 70%, 80%, 90%, 95%, 98%, or even 99%.

The inventive JNK inhibitor sequences may further comprise or consist of at least one derivative of (native or non-native) amino acid sequences according to SEQ ID NOs: 1, 2, 3 or 4. In this context, a "derivative of an (native or non-native) amino acid sequence according to SEQ ID NOs: 1, 2, 3 or 4" is preferably an amino acid sequence derived from any of the sequences according to SEQ ID NOs: 1, 2, 3 or 4, wherein the derivative comprises at least one modified L- or D-amino acid (forming non-natural amino acid(s)), preferably 1 to 20, more preferably 1 to 10, and even more preferably 1 to 5 modified L- or D-amino acids. Derivatives of variants or fragments also fall under the scope of the present invention.

Any of the peptides disclosed herein may have a modification at their termini, either C- or N-terminus or both. The C-Terminus may preferably be modified by an amide modification, whereas the N-terminus may be modified by any suitable NH2-protection group, such as e.g. acylation.

"A modified amino acid" in this respect may be any amino acid which is altered e.g. by different glycosylation in various organisms, by phosphorylation or by labeling specific amino acids. Such a label is then typically selected from the group of labels comprising:
(i) radioactive labels, i.e. radioactive phosphorylation or a radioactive label with sulphur, hydrogen, carbon, nitrogen, etc.;
(ii) colored dyes (e.g. digoxygenin, etc.);
(iii) fluorescent groups (e.g. fluorescein, etc.);
(iv) chemoluminescent groups;
(v) groups for immobilization on a solid phase (e.g. His-tag, biotin, strep-tag, flag-tag, antibodies, antigen, etc.); and
(vi) a combination of labels of two or more of the labels mentioned under (i) to (v).

In the above context, an amino acid sequence having a sequence "sharing a sequence identity" of at least, for example, 95% to a query amino acid sequence of the present invention, is intended to mean that the sequence of the subject amino acid sequence is identical to the query sequence except that the subject amino acid sequence may include up to five amino acid alterations per each 100 amino acids of the query amino acid sequence. In other words, to obtain an amino acid sequence having a sequence of at least 95% identity to a query amino acid sequence, up to 5% (5 of 100) of the amino acid residues in the subject sequence may be inserted or substituted with another amino acid or deleted.

For sequences without exact correspondence, a "% identity" of a first sequence may be determined with respect to a second sequence. In general, these two sequences to be compared are aligned to give a maximum correlation between the sequences. This may include inserting "gaps" in either one or both sequences, to enhance the degree of alignment. A % identity may then be determined over the whole length of each of the sequences being compared (so-called global alignment), that is particularly suitable for sequences of the same or similar length, or over shorter, defined lengths (so-called local alignment), that is more suitable for sequences of unequal length.

Methods for comparing the identity and homology of two or more sequences are well known in the art. Thus for instance, programs available in the Wisconsin Sequence Analysis Package, version 9.1 (Devereux et al., 1984, Nucleic Acids Res. 12, 387-395.), for example the programs BESTFIT and GAP, may be used to determine the % identity between two polynucleotides and the % identity and the % homology between two polypeptide sequences. BESTFIT uses the "local homology" algorithm of (Smith and Waterman (1981), J. Mol. Biol. 147, 195-197.) and finds the best single region of similarity between two sequences. Other programs for determining identity and/or similarity between sequences are also known in the art, for instance the BLAST family of programs (Altschul et al., 1990, J. Mol. Biol. 215, 403-410), accessible through the home page of the NCBI at world wide web site ncbi.nlm.nih.gov) and FASTA (Pearson (1990), Methods Enzymol. 183, 63-98; Pearson and Lipman (1988), Proc. Natl. Acad. Sci. U.S.A 85, 2444-2448.).

JNK-inhibitor sequences according to the present invention may be obtained or produced by methods well-known in the art, e.g. by chemical synthesis or by genetic engineering methods as discussed below. For example, a peptide corresponding to a portion of an inventive JNK inhibitor sequence including a desired region of said JNK inhibitor sequence, or that mediates the desired activity in vitro or in vivo, may be synthesized by use of a peptide synthesizer.

According to a second aspect the present invention provides a chimeric peptide including at least one first domain and at least one second domain, wherein the first domain comprises a trafficking sequence, while the second domain comprises an inventive JNK inhibitor sequence as defined above.

Typically, chimeric peptides according to the present invention have a length of at least 25 amino acid residues, e.g. 25 to 250 amino acid residues, more preferably 25 to 200 amino acid residues, even more preferably 25 to 150 amino acid residues, 25 to 100 and most preferably amino acid 25 to 50 amino acid residues.

As a first domain the inventive chimeric peptide preferably comprises a trafficking sequence, which is typically selected from any sequence of amino acids that directs a peptide (in which it is present) to a desired cellular destination. Thus, the trafficking sequence, as used herein, typically directs the peptide across the plasma membrane, e.g. from outside the cell, through the plasma membrane, and into the cytoplasm. Alternatively, or in addition, the trafficking sequence may direct the peptide to a desired location within the cell, e.g. the nucleus, the ribosome, the endoplasmic reticulum (ER), a lysosome, or peroxisome, by e.g. combining two components (e.g. a component for cell permeability and a component for nuclear location) or by one single component having e.g. properties of cell membrane transport and targeted e.g. intranuclear transport. The trafficking sequence may additionally comprise another component, which is capable of binding a cytoplasmic component or any other component or compartment of the cell (e.g. endoplasmic reticulum, mitochondria, gloom apparatus, lysosomal vesicles). Accordingly, e.g. the trafficking sequence of the first domain and the JNK inhibitor sequence of the second domain may be localized in the cytoplasm or any other compartment of the cell. This allows to determine localization of the chimeric peptide in the cell upon uptake.

Preferably, the trafficking sequence (being included in the first domain of the inventive chimeric peptide) has a length of 5 to 150 amino acid sequences, more preferably a length of 5 to 100 and most preferably a length of from 5 to 50, 5 to 30 or even 5 to 15 amino acids.

More preferably, the trafficking sequence (contained in the first domain of the inventive chimeric peptide) may occur as a continuous amino acid sequence stretch in the first domain. Alternatively, the trafficking sequence in the first domain may be cleaved into two or more fragments, wherein all of these fragments resemble the entire trafficking sequence and may be separated from each other by 1 to 10, preferably 1 to 5 amino acids, provided that the trafficking sequence as such retains its carrier properties as disclosed above. These amino acids separating the fragments of the trafficking sequence may e.g. be selected from amino acid sequences differing from the trafficking sequence. Alternatively, the first domain may contain a trafficking sequence composed of more than one component, each component with its own function for the transport of the cargo JNK inhibitor sequence of the second domain to e.g. a specific cell compartment.

The trafficking sequence as defined above may be composed of L-amino acids, D-amino acids, or a combination of both. Preferably, the inventive trafficking sequences comprise at least 1, preferably at least 3, more preferably at least 6 and even more preferably at least 10 L-amino acids and/or D-amino acids, wherein the D- and/or L-amino acids may be arranged in the inventive JNK trafficking sequences in a blockwise, a non-blockwise or in an alternate manner.

According to one alternative embodiment, the trafficking sequence of the inventive chimeric peptide may be exclusively composed of L-amino acids. More preferably, the trafficking sequence of the inventive chimeric peptide comprises or consists of at least one "native" trafficking sequence as defined above. In this context, the term "native" is referred to non-altered trafficking sequences, entirely composed of L-amino acids.

According to another alternative embodiment the trafficking sequence of the inventive chimeric peptide may be exclusively composed of D-amino acids. More preferably, the trafficking sequence of the inventive chimeric peptide may comprise a D retro-inverso peptide of the sequences as presented above.

The trafficking sequence of the first domain of the inventive chimeric peptide may be obtained from naturally occurring sources or can be produced by using genetic engineering techniques or chemical synthesis (see e.g. Sambrook, J., Fritsch, E. F., Maniatis, T. (1989) Molecular cloning: A laboratory manual. 2nd edition. Cold Spring Harbor Laboratory Press, Cold Spring Harbor, N.Y.).

Sources for the trafficking sequence of the first domain may be employed including, e.g. native proteins such as e.g. the TAT protein (e.g. as described in U.S. Pat. Nos. 5,804,604 and 5,674,980, each of these references being incorporated herein by reference), VP22 (described in e.g. WO 97/05265; Elliott and O'Hare, Cell 88: 223-233 (1997)), non-viral proteins (Jackson et al, Proc. Natl. Acad. Sci. USA 89: 10691-10695 (1992)), trafficking sequences derived from Antennapedia (e.g. the antennapedia carrier sequence) or from basic peptides, e.g. peptides having a length of 5 to 15 amino acids, preferably 10 to 12 amino acids and comprising at least 80%, more preferably 85% or even 90% basic amino acids, such as e.g. arginine, lysine and/or histidine. Furthermore, variants, fragments and derivatives of one of the native proteins used as trafficking sequences are disclosed herewith. With regard to variants, fragments and derivatives it is referred to the definition given above for JNK inhibitor sequences. Variants, fragments as well as derivatives are correspondingly defined as set forth above for JNK inhibitor sequences. Particularly, in the context of the trafficking sequence, a variant or fragment or derivative may be defined as a sequence sharing a sequence identity with one of the native proteins used as trafficking sequences as defined above of at least about 30%, 50%, 70%, 80%, 90%, 95%, 98%, or even 99%.

In a preferred embodiment of the inventive chimeric peptide, the trafficking sequence of the first domain comprises or consists of a sequence derived from the human immunodeficiency virus (HIV)1 TAT protein, particularly some or all of the 86 amino acids that make up the TAT protein.

For an inventive trafficking sequence, partial sequences of the full-length TAT protein may be used forming a functionally effective fragment of a TAT protein, i.e. a TAT peptide that includes the region that mediates entry and uptake into cells. As to whether such a sequence is a functionally effective fragment of the TAT protein can be determined using known techniques (see e.g. Franked et al., Proc. Natl. Acad. Sci, USA 86: 7397-7401 (1989)). Thus, the trafficking sequence in the first domain of the inventive chimeric peptide may be derived from a functionally effective fragment or portion of a TAT protein sequence that comprises less than 86 amino acids, and which exhibits uptake into cells, and optionally the uptake into the cell nucleus. More preferably, partial sequences (fragments) of TAT to be used as carrier to mediate permeation of the chimeric peptide across the cell membrane, are intended to comprise the basic region (amino acids 48 to 57 or 49 to 57) of full-length TAT.

According to a more preferred embodiment, the inventive trafficking sequence may comprise or consist of an amino acid sequence containing TAT residues 48-57 or 49 to 57, and most preferably a generic TAT sequence $NH_2$-$X_n^b$-RKKRRQRRR-$X_n^b$-COOH [SEQ ID NO: 7], wherein $X_n^b$ is as defined above. Alternatively, the inventive trafficking sequence may comprise or consist of a peptide containing e.g. the amino acid sequence $NH_2$-GRKKRRQRRR-COOH [SEQ ID NO: 5].

According to another more preferred embodiment the inventive trafficking sequence may comprise a D retro-inverso peptide of the sequences as presented above, i.e. the D retro-inverso sequence of the generic TAT sequence having the sequence $NH_2$-$X_n^b$-RRRQRRKKR-$X_n^b$-COOH [SEQ ID NO: 8]. Also here, $X_n^b$ is as defined above (preferably representing D amino acids). Furthermore, the number of "$X_n^b$" residues in any of SEQ ID NOs: 7-8 is not limited to the one depicted, and may vary as described above. Most preferably, the inventive trafficking sequence may comprise the D retro-inverso sequence $NH_2$-RRRQRRKKRG-COOH [SEQ ID NO: 6].

According to another embodiment the inventive trafficking sequence may comprise or consist of variants of the trafficking sequences as defined above. A "variant of a trafficking sequence" is preferably a sequence derived from a trafficking sequence as defined above, wherein the variant comprises a modification, for example, addition, (internal) deletion (leading to fragments) and/or substitution of at least one amino acid present in the trafficking sequence as defined above. Such (a) modification(s) typically comprise(s) 1 to 20, preferably 1 to 10 and more preferably 1 to 5 substitutions, additions and/or deletions of amino acids. Furthermore, the variant preferably exhibits a sequence identity with the trafficking sequence as defined above, more preferably with any of SEQ ID NOs: 5 to 8, of at least about 30%, 50%, 70%, 80%, 90%, 95%, 98% or even 99%.

Preferably, such a modification of the trafficking sequence leads to a trafficking sequence with increased or decreased stability. Alternatively, variants of the trafficking sequence can be designed to modulate intracellular localization of the inventive chimeric peptide. When added exogenously, such variants as defined above are typically designed such that the ability of the trafficking sequence to enter cells is retained (i.e. the uptake of the variant of the trafficking sequence into the cell is substantially similar to that of the native protein used a trafficking sequence). For example, alteration of the basic region thought to be important for nuclear localization (see e.g. Dang and Lee, J. Biol. Chem. 264: 18019-18023 (1989); Hauber et al., J. Virol. 63: 1181-1187 (1989); et al., J. Virol. 63: 1-8 (1989)) can result in a cytoplasmic location or partially cytoplasmic location of the trafficking sequence, and therefore, of the JNK inhibitor sequence as component of the inventive chimeric peptide. Additional to the above, further modifications may be introduced into the variant, e.g. by linking e.g. cholesterol or other lipid moieties to the trafficking sequence to produce a trafficking sequence having increased membrane solubility. Any of the above disclosed variants of the inventive trafficking sequences can be produced using techniques typically known to a skilled person (see e.g. Sambrook, J., Fritsch, E. F., Maniatis, T. (1989) Molecular cloning: A laboratory manual. 2nd edition. Cold Spring Harbor Laboratory, Cold Spring Harbor, N.Y.)

As a second domain the inventive chimeric peptide typically comprises an inventive JNK inhibitor sequence, selected from any of the inventive JNK inhibitor sequences as defined above, including variants, fragments and/or derivatives of these inventive JNK inhibitor sequences.

Both domains, i.e. the first and the second domain(s) of the inventive chimeric peptide, may be linked such as to form a functional unit. Any method for linking the first and second domain(s) as generally known in the art may be applied.

According to an alternative specific embodiment the inventive chimeric peptide comprises or consists of D-amino acid chimeric peptides of the above disclosed L-amino acid chimeric peptides. Exemplary D retro-inverso chimeric peptides according to the present invention are e.g. the generic D -TAT-IB peptide [NH$_2$-X$_n$$^b$-DQXXXXXXXLXLTTPR-X$_n$$^a$-X$_n$$^b$-RRRQRRKKR-X$_n$$^b$-COOH, SEQ ID NO: 12]. Herein, X, X$_n$$^a$ and X$_n$$^b$ are preferably as defined above (preferably representing D amino acids). More preferably, the inventive chimeric peptide comprises or consists of D-amino acid chimeric peptides according to the TAT-IB1peptide [NH$_2$-DQSRPVQPFLNLTTPRKPRPPRRRQRRKKRG-COOH, SEQ ID NO: 11]. However, the linking portion of the first and second domain (instead of PP) may be composed of -X$_n$$^a$-X$_n$$^b$-, which are as defined above. In particular, the second domain(s) of SEQ ID NO: 11, eventually with -X$_n$$^a$-X$_n$$^b$- instead of (PP), may be deleted at their N- and/or C-terminus by 1,2,3,4, or 5amino acids. In another preferred embodiment, the first domain of SEQ ID NO: 11may be deleted at its N- and or C-terminus by 1or 2amino acids. This/these deletion/s may be combined with the deletion/s disclosed for the amino acid residues of the termini of the second domain. Accordingly, preferred variants of SEQ ID NO: 11 are e.g. the following sequences with deletions of the second domain at their N- and/or C-terminus/i: QSRPVQPFLNLTTPRKPR-X$_n$$^a$-X$_n$$^b$-RRRQRRKKRG (SEQ ID NO: 44), SRPVQPFLNLTTPRKPR-X$_n$$^a$-X$_n$$^b$-RRRQRRKKRG (SEQ ID NO: 45), RPVQPFLNLTTPRKPR-X$_n$$^a$-X$_n$$^b$-RRRQRRKKRG (SEQ ID NO: 46), PVQPFLNLTTPRKPR-X$_n$$^a$-X$_n$$^b$-RRRQRRKKRG (SEQ ID NO: 47 ), or VQPFLNLTTPRKPR-X$_n$$^a$-X$_n$$^b$-RRRQRRKKRG (SEQ ID NO: 48) or, respectively, DQSRPVQPFLNLTTPRKP-X$_n$$^a$-X$_n$$^b$-RRRQRRKKRG (SEQ ID NO: 49), DQSRPVQPFLNLTTPRK-X$_n$$^a$-X$_n$$^b$-RRRQRRKKRG (SEQ ID NO: 50), DQSRPVQPFLNLT-TPR-X$_n$$^a$-X$_n$$^b$-RRRQRRKKRG (SEQ ID NO: 51), DQSR-PVQPFLNLTTP-X$_n$$^a$-X$_n$$^b$-RRRQRRKKRG (SEQ ID NO: 52), DQSRPVQPFLNLTT-X$_n$$^a$-X$_n$$^b$-RRRQRRKKRG (SEQ ID NO: 53), or QSRPVQPFLNLTTPRKP-X$_n$$^a$-X$_n$$^b$-RRRQRRKKRG (SEQ ID NO: 54), SRPVQPFLNLT-TPRKP-X$_n$$^a$-X$_n$$^b$-RRRQRRKKRG (SEQ ID NO: 55), SRPVQPFLNLTTPRK-X$_n$$^a$-X$_n$$^b$-RRRQRRKKRG (SEQ ID NO: 56), RPVQPFLNLTTPRKP-X$_n$$^a$-X$_n$$^b$-RRRQRRKKRG (SEQ ID NO: 57), RPVQPFLNLTTPRK-X$_n$$^a$-X$_n$$^b$-RRRQR-RKKRG (SEQ ID NO: 58) or PVQPFLNLTTP-X$_n$$^a$-X$_n$$^b$-RRRQRRKKRG (SEQ ID NO: 59). Preferred embodiments containing merely deletions at the terminus/i of the first domain are: QSRPVQPFLNLTTPRKPR-X$_n$$^a$-X$_n$$^b$-RRRQR-RKKR (SEQ ID NO: 60), QSRPVQPFLNLTTPRKPR-X$_n$$^a$-X$_n$$^b$-RRRQRRKK (SEQ ID NO: 61), QSRPVQPFLNLT-TPRKPR-X$_n$$^a$-X$_n$$^b$-RRRQRRKKRG (SEQ ID NO: 62), QSRPVQPFLNLTTPRKPR -X$_n$$^a$-X$_n$$^b$-RQRRKKRG (SEQ ID NO: 63), QSRPVQPFLNLTTPRKPR-X$_n$$^a$-X$_n$$^b$-RRQR-RKKR (SEQ ID NO: 64), QSRPVQPFLNLTTPRKPR-X$_n$$^a$-X$_n$$^b$-RQRRKKR (SEQ ID NO: 65), QSRPVQPFLNLT-TPRKPR-X$_n$$^a$-X$_n$$^b$-RQRRKK (SEQ ID NO: 66 . Examples of combinations of deletions in the first and second domain are: QSRPVQPFLNLTTPRKPR-X$_n$$^a$-X$_n$$^b$-RRRQRRKKR (SEQ ID NO: 67), SRPVQPFLNLTTPRKPR-X$_n$$^a$-X$_n$$^b$-RRRQRRKKR (SEQ ID NO: 68), RPVQPFLNLTTPRKPR-X$_n$$^a$-X$_n$$^b$-RRRQRRKKR (SEQ ID NO: 69), PVQPFLNLT-TPRKPR-X$_n$$^a$-X$_n$$^b$-RRRQRRKKR (SEQ ID NO: 70), or VQPFLNLTTPRKPR-X$_n$$^a$-X$_n$$^b$-RRRQRRKKR (SEQ ID NO: 71) or, respectively, DQSRPVQPFLNLTTPRKP-X$_n$$^a$-X$_n$$^b$-RRRQRRKKR (SEQ ID NO: 72), DQSRPVQPFLNLT-TPRK-X$_n$$^a$-X$_n$$^b$-RRRQRRKKR (SEQ ID NO: 73), DQSR-PVQPFLNLTTPR-X$_n$$^a$-X$_n$$^b$-RRRQRRKKR (SEQ ID NO: 74), DQSRPVQPFLNLTTP-X$_n$$^a$-X$_n$$^b$-RRRQRRKKR (SEQ ID NO: 75), DQSRPVQPFLNLTT-X$_n$$^a$-X$_n$$^b$-RRRQRRKKR (SEQ ID NO: 76), or QSRPVQPFLNLTTPRKP-X$_n$$^a$-X$_n$$^b$-RRRQRRKKR (SEQ ID NO: 77), SRPVQPFLNLTTPRKP-X$_n$$^a$-X$_n$$^b$-RRRQRRKKR (SEQ ID NO: 78), SRPVQPFLN-LTTPRK-X$_n$$^a$-X$_n$$^b$-RRRQRRKKR (SEQ ID NO: 79), RPVQPFLNLTTPRKP-X$_n$$^a$-X$_n$$^b$-RRRQRRKKR (SEQ ID NO: 80), RPVQPFLNLTTPRK-X$_n$$^a$-X$_n$$^b$-RRRQRRKKR (SEQ ID NO: 81) or PVQPFLNLTTP -X$_n$$^a$-X$_n$$^b$-RRRQR-RKKR (SEQ ID NO: 82), QSRPVQPFLNLTTPRKPR-X$_n$$^a$-X$_n$$^b$-RRRQRRKK (SEQ ID NO: 83), SRPVQPFLNLT-TPRKPR-X$_n$$^a$-X$_n$$^b$-RRRQRRKKRG (SEQ ID NO: 84), RPVQPFLNLTTPRKPR-X$_n$$^a$-X$_n$$^b$-RRRQRRKK (SEQ ID NO: 85), PVQPFLNLTTPRKPR-X$_n$$^a$- X$_n$$^b$-RRRQRRKK (SEQ ID NO: 86), or VQPFLNLTTPRKPR-X$_n$$^a$-X$_n$$^b$-RRRQRRKK (SEQ ID NO: 87) or, respectively, DQSR-PVQPFLNLTTPRKP-X$_n$$^a$-X$_n$$^b$-RRRQRRKK (SEQ ID NO: 88), DQSRPVQPFLNLTTPRK-X$_n$$^a$-X$_n$$^b$-RRRQRRKK (SEQ ID NO: 89), DQSRPVQPFLNLTTPR -X$_n$$^a$-X$_n$$^b$-RRRQRRKK (SEQ ID NO: 90), DQSRPVQPFLNLTTP-X$_n$$^a$-X$_n$$^b$-RRRQRRKK (SEQ ID NO: 91), DQSRPVQPFLN-LTT-X$_n$$^a$-X$_n$$^b$-RRRQRRKK (SEQ ID NO: 92), or QSRPVQPFLNLTTPRKP-X$_n$$^a$-X$_n$$^b$-RRRQRRKK (SEQ ID NO: 93), SRPVQPFLNLTTPRKP-X$_n$$^a$-X$_n$$^b$-RRRQRRKK (SEQ ID NO: 94), SRPVQPFLNLTTPRK-X$_n$$^a$-X$_n$$^b$-RRRQRRKK (SEQ ID NO: 95), RPVQPFLNLTTPRKP-X$_n$$^a$-X$_n$$^b$-RRRQRRKK (SEQ ID NO: 96), RPVQPFLNLT-TPRK-X$_n$$^a$-X$_n$$^b$-RRRQRRKK (SEQ ID NO: 97) or PVQPFLNLTTP-X$_n$$^a$-X$_n$$^b$-RRRQRRKK (SEQ ID NO: 98, QSRPVQPFLNLTTPRKPR-X$_n$a-X$_n$$^b$-RRQRRKKR (SEQ ID NO: 99), SRPVQPFLNLTTPRKPR-X$_n$$^a$-X$_n$$^b$-RRQR-RKKR (SEQ ID NO: 100), RPVQPFLNLTTPRKPR-X$_n$$^a$-X$_n$$^b$-RRQRRKKR (SEQ ID NO: 101), PVQPFLNLT-TPRKPR-X$_n$$^a$-X$_n$$^b$-RRQRRKKR (SEQ ID NO: 102), or VQPFLNLTTPRKPR-X$_n$$^a$-X$_n$$^b$-RRQRRKKR (SEQ ID NO: 103) or, respectively, DQSRPVQPFLNLTTPRKP-X$_n$$^a$-X$_n$$^b$-RRQRRKKR (SEQ ID NO: 104), DQSRPVQPFLNLT-TPRK-X$_n$$^a$-X$_n$$^b$-RRQRRKKR (SEQ ID NO: 105), DQSR-PVQPFLNLTTPR-X$_n$$^a$-X$_n$$^b$-RRQRRKKR (SEQ ID NO: 106), DQSRPVQPFLNLTTP-X$_n$$^a$-X$_n$$^b$-RRQRRKKR (SEQ ID NO: 107), DQSRPVQPFLNLTT-X$_n$$^a$-X$_n$$^b$-RRQRRKKR (SEQ ID NO: 108), or QSRPVQPFLNLTTPRKP-X$_n$$^a$-X$_n$$^b$-RRQRRKKR (SEQ ID NO: 109), SRPVQPFLNLTTPRKP-X$_n$$^a$-X$_n$$^b$-RRQRRKKRG (SEQ ID NO: 110), SRPVQPFLN-LTTPRK-X$_n$$^a$-X$_n$$^b$-RRQRRKKRG (SEQ ID NO: 111), RPVQPFLNLTTPRKP-X$_n$$^a$-X$_n$$^b$-RRQRRKKRG (SEQ ID NO: 112), RPVQPFLNLTTPRK-X$_n$$^a$-X$_n$$^b$-RRQRRKKRG (SEQ ID NO: 113) or PVQPFLNLTTP-X$_n$$^a$-X$_n$$^b$-RRQR-RKKRG (SEQ ID NO: 114), QSRPVQPFLNLTTPRKPR-X$_n$$^a$-X$_n$$^b$-RRQRRKKRG (SEQ ID NO: 115), SRPVQPFLN-LTTPRKPR-X$_n$$^a$-X$_n$$^b$-RRQRRKKRG (SEQ ID NO: 116), RPVQPFLNLTTPRKPR-X$_n$$^a$-X$_n$$^b$-RRQRRKKRG (SEQ ID NO: 117, PVQPFLNLTTPRKPR-X$_n$$^a$-X$_n$$^b$-RRQRRKKRG (SEQ ID NO: 118), or VQPFLNLTTPRKPR-X$_n$$^a$-X$_n$$^b$-

RRQRRKKRG (SEQ ID NO: 119) or, respectively, DQSRPVQPFLNLTTPRKP-$X_n^a$-$X_n^b$-RRQRRKKRG (SEQ ID NO: 120), DQSRPVQPFLNLTTPRK-$X_n^a$-$X_n^b$-RRQRRKKRG (SEQ ID NO: 121), DQSRPVQPFLNLTTPR-$X_n^a$-$X_n^b$-RRQRRKKRG (SEQ ID NO: 122), DQSRPVQPFLNLTTP -$X_n^a$-$X_n^b$-RRQRRKKRG (SEQ ID NO: 123), DQSRPVQPFLNLTT-$X_n^a$-$X_n^b$-RRQRRKKRG (SEQ ID NO: 124), or QSRPVQPFLNLTTPRKP -$X_n^a$-$X_n^b$-RRQRRKKRG (SEQ ID NO: 125), SRPVQPFLNLTTPRKP-$X_n^a$-$X_n^b$-RRQRRKKRG (SEQ ID NO: 126), SRPVQPFLNLTTPRK-$X_n^a$-$X_n^b$-RRQRRKKRG (SEQ ID NO: 127), RPVQPFLNLTTPRKP -$X_n^a$-$X_n^b$-RRQRRKKRG (SEQ ID NO: 128), RPVQPFLNLTTPRK-$X_n^a$-$X_n^b$-RRQRRKKRG (SEQ ID NO: 129) or PVQPFLNLTTP-$X_n^a$-$X_n^b$-RRQRRKKRG (SEQ ID NO: 130), QSRPVQPFLNLTTPRKPR-$X_n^a$-$X_n^b$-RQRRKKRG (SEQ ID NO: 131), SRPVQPFLNLTTPRKPR-$X_n^a$-$X_n^b$-RQRRKKRG (SEQ ID NO: 132), RPVQPFLNLTTPRKPR-$X_n^a$-$X_n^b$-RQRRKKRG (SEQ ID NO: 133), PVQPFLNLTTPRKPR-$X_n^a$- $X_n^b$-RQRRKKRG (SEQ ID NO: 134), or VQPFLNLTTPRKPR-$X_n^a$-$X_n^b$-RQRRKKRG (SEQ ID NO: 135) or, respectively, DQSRPVQPFLNLTTPRKP-$X_n^a$-$X_n^b$-RQRRKKRG (SEQ ID NO: 136), DQSRPVQPFLNLTTPRK-$X_n^a$-$X_n^b$-RQRRKKRG (SEQ ID NO: 137), DQSRPVQPFLNLTTPR-$X_n^a$-$X_n^b$-RQRRKKRG (SEQ ID NO: 138), DQSRPVQPFLNLTTP-$X_n^a$-$X_n^b$-RQRRKKRG (SEQ ID NO: 139), DQSRPVQPFLNLTT-$X_n^a$-$X_n^b$-RQRRKKRG (SEQ ID NO: 140), or QSRPVQPFLNLTTPRKP-$X_n^a$-$X_n^b$-RQRRKKRG (SEQ ID NO: 141, SRPVQPFLNLTTPRKP-$X_n^a$-$X_n^b$-RQRRKKRG (SEQ ID NO: 142), SRPVQPFLNLTTPRK-$X_n^a$-$X_n^b$-RQRRKKRG (SEQ ID NO: 143), RPVQPFLNLTTPRKP-$X_n^a$-$X_n^b$-RQRRKKRG (SEQ ID NO: 144), RPVQPFLNLTTPRK-$X_n^a$-$X_n^b$-RQRRKKRG (SEQ ID NO: 145) or PVQPFLNLTTP-$X_n^a$-$X_n^b$-RQRRKKRG (SEQ ID NO: 146). Again, the shorter the peptides are, the less their (unspecific) cell toxicity. However, the peptides must retain their biological function, i.e. their cell membrane permeability (first domain) and their JNK inhibitory function (second domain).

The first and second domain(s) of the inventive chimeric peptide as defined above may be linked to each other by chemical or biochemical coupling carried out in any suitable manner known in the art, e.g. by establishing a peptide bond between the first and the second domain(s) e.g. by expressing the first and second domain(s) as a fusion protein, or e.g. by crosslinking the first and second domain(s) of the inventive chimeric peptide.

Many known chemical crosslinking methods are non-specific, i.e. they do not direct the point of coupling to any particular site on the transport polypeptide or cargo macromolecule. As a result, use of non-specific crosslinking agents may attack functional sites or sterically block active sites, rendering the conjugated proteins biologically inactive. Thus, preferably such crosslinking methods are used, which allow a more specific coupling of the first and second domain(s).

One way to increasing coupling specificity is a direct chemical coupling to a functional group present only once or a few times in one or both of the first and second domain(s) to be crosslinked. For example, cysteine, which is the only protein amino acid containing a thiol group, occurs in many proteins only a few times. Also, for example, if a polypeptide contains no lysine residues, a crosslinking reagent specific for primary amines will be selective for the amino terminus of that polypeptide. Successful utilization of this approach to increase coupling specificity requires that the polypeptide have the suitably rare and reactive residues in areas of the molecule that may be altered without loss of the molecule's biological activity.

Cysteine residues may be replaced when they occur in parts of a polypeptide sequence where their participation in a crosslinking reaction would otherwise likely interfere with biological activity. When a cysteine residue is replaced, it is typically desirable to minimize resulting changes in polypeptide folding. Changes in polypeptide folding are minimized when the replacement is chemically and sterically similar to cysteine. For these reasons, serine is preferred as a replacement for cysteine. As demonstrated in the examples below, a cysteine residue may be introduced into a polypeptide's amino acid sequence for crosslinking purposes.

When a cysteine residue is introduced, introduction at or near the amino or carboxy terminus is preferred. Conventional methods are available for such amino acid sequence modifications, wherein the polypeptide of interest is produced by chemical synthesis or via expression of recombinant DNA.

Coupling of the first and second domain(s) can also be accomplished via a coupling or conjugating agent. There are several intermolecular crosslinking reagents which can be utilized (see for example, Means and Feeney, CHEMICAL MODIFICATION OF PROTEINS, Holden-Day, 1974, pp. 39-43). Among these reagents are, for example, N-succinimidyl 3-(2-pyridyldithio) propionate (SPDP) or N,N'-(1,3-phenylene) bismaleimide (both of which are highly specific for sulfhydryl groups and form irreversible linkages); N,N'-ethylene-bis-(iodoacetamide) or other such reagent having 6 to 11 carbon methylene bridges (which are relatively specific for sulfhydryl groups); and 1,5-difluoro-2,4-dinitrobenzene (which forms irreversible linkages with amino and tyrosine groups). Other crosslinking reagents useful for this purpose include: p,p'-difluoro-m, m'-dinitrodiphenylsulfone which forms irreversible crosslinkages with amino and phenolic groups); dimethyl adipimidate (which is specific for amino groups); phenol-1,4 disulfonylchloride (which reacts principally with amino groups); hexamethylenediisocyanate or diisothiocyanate, or azophenyl-p-diisocyanate (which reacts principally with amino groups); glutaraldehyde (which reacts with several different side chains) and disdiazobenzidine (which reacts primarily with tyrosine and histidine).

Crosslinking reagents may be homobifunctional, i.e. having two functional groups that undergo the same reaction. A preferred homobifunctional crosslinking reagent is bismaleimidohexane ("BMH"). BMH contains two maleimide functional groups, which react specifically with sulfhydryl-containing compounds under mild conditions (pH 6.5-7.7). The two maleimide groups are connected by a hydrocarbon chain. Therefore, BMH is useful for irreversible crosslinking of polypeptides that contain cysteine residues.

Crosslinking reagents may also be heterobifunctional. Heterobifunctional crosslinking agents have two different functional groups, for example an amine-reactive group and a thiol-reactive group, that will crosslink two proteins having free amines and thiols, respectively.

Examples of heterobifunctional crosslinking agents are succinimidyl 4-(N-maleimidomethyl)cyclohexane-1-carboxylate ("SMCC"), m-maleimidobenzoyl-N-hydroxysuccinimide ester ("MBS"), and succinimide 4-(p-maleimidophenyl)butyrate ("SMPB"), an extended chain analog of MBS. The succinimidyl group of these crosslinkers reacts with a primary amine, and the thiol-reactive maleimide forms a covalent bond with the thiol of a cysteine residue.

Crosslinking reagents often have low solubility in water. A hydrophilic moiety, such as a sulfonate group, may be added to the crosslinking reagent to improve its water solubility. In this respect, Sulfo-MBS and Sulfo-SMCC are examples of crosslinking reagents modified for water solubility, which may be used according to the present invention.

Many crosslinking reagents yield a conjugate that is essentially non-cleavable under cellular conditions. However, some crosslinking reagents contain a covalent bond, such as a disulfide, that is cleavable under cellular conditions. For example, Traut's reagent, dithiobis(succinimidylpropionate) ("DSP"), and N-succinimidyl 3-(2-pyridyldithio)propionate ("SPDP") are well-known cleavable crosslinkers. The use of a cleavable crosslinking reagent permits the cargo moiety to separate from the transport polypeptide after delivery into the target cell. Direct disulfide linkage may also be useful.

Numerous crosslinking reagents, including the ones discussed above, are commercially available. Detailed instructions for their use are readily available from the commercial suppliers. A general reference on protein crosslinking and conjugate preparation is: Wong, CHEMISTRY OF PROTEIN CONJUGATION AND CROSSLINKING, CRC Press (1991).

Chemical crosslinking may include the use of spacer arms. Spacer arms provide intramolecular flexibility or adjust intramolecular distances between conjugated moieties and thereby may help preserve biological activity. A spacer arm may be in the form of a polypeptide moiety that includes spacer amino acids, e.g. proline. Alternatively, a spacer arm may be part of the crosslinking reagent, such as in "long-chain SPDP" (Pierce Chem. Co., Rockford, Ill., cat. No. 21651 H).

Furthermore, variants, fragments or derivatives of one of the above disclosed chimeric peptides are disclosed herewith. With regard to fragments and variants it is generally referred to the definition given above for JNK inhibitor sequences.

Particularly, in the context of the present invention, a "variant of a chimeric peptide" is preferably a sequence derived from any of the sequences according to SEQ ID NOs: 9 to 12, wherein the chimeric variant comprises amino acid alterations of the inventive chimeric peptides according to SEQ ID NOs: 9 to 12. Such alterations typically comprise 1 to 20, preferably 1 to 10 and more preferably 1 to 5 substitutions, additions and/or deletions (leading to fragments) of amino acids according to SEQ ID NOs: 9 to 12, wherein the altered inventive chimeric peptide exhibits a sequence identity with any of the sequences according to SEQ ID NOs: 9, 10, 11 or 12 of at least about 30%, 50%, 70%, 80%, or 95%, 98%, or even 99%. Preferably, these variants retain the biological activity of the first and the second domain as contained in the inventive chimeric peptide, i.e. the trafficking activity of the first domain as disclosed above and the activity of the second domain for binding JNK and/or inhibiting the activation of at least one JNK activated transcription factor.

Accordingly, the inventive chimeric peptide also comprises fragments of the afore disclosed inventive chimeric peptides, particularly of the inventive chimeric peptide sequences according to SEQ ID NOs: 9, 10, 11 or 12. Thus, in the context of the present invention, a "fragment of the inventive chimeric peptide" is preferably a sequence derived any of the sequences according to SEQ ID NOs: 9, 10, 11 or 12, wherein the fragment comprises at least 4 contiguous amino acids of any of SEQ ID NOs: 9, 10, 11 or 12. This fragment preferably comprises a length which is sufficient to allow specific recognition of an epitope from any of these sequences and to transport the sequence into the cells, the nucleus or a further preferred location. Even more preferably, the fragment comprises 4 to 18, 4 to 15, or most preferably 4 to 10 contiguous amino acids of any of SEQ ID NOs: 9, 10, 11 or 12. Fragments of the inventive chimeric peptide further may be defined as a sequence sharing a sequence identity with any of the sequences according to SEQ ID NOs: 9, 10, 11 or 12 of at least about 30%, 50%, 70%, 80%, or 95%, 98%, or even 99%.

Finally, the inventive chimeric peptide also comprises derivatives of the afore disclosed inventive chimeric peptides, particularly of the inventive chimeric peptide sequences according to SEQ ID NOs: 9, 10, 11 or 12.

The present invention additionally refers to nucleic acid sequences encoding inventive JNK inhibitor sequences, inventive chimeric peptides, or their fragments, variants or derivatives as defined above. A preferable suitable nucleic acid encoding an inventive JNK inhibitor sequence is chosen from human IB1 nucleic acid (GenBank Accession No. (AF074091), rat IB1 nucleic acid (GenBank Accession No. AF 108959), or human IB2 (GenBank Accession No AF218778).

Nucleic acids encoding the inventive JNK inhibitor sequences or chimeric peptides may be obtained by any method known in the art (e.g. by PCR amplification using synthetic primers hybridizable to the 3'- and 5'-termini of the sequence and/or by cloning from a cDNA or genomic library using an oligonucleotide sequence specific for the given gene sequence).

Additionally, nucleic acid sequences are disclosed herein as well, which hybridize under stringent conditions with the appropriate strand coding for a (native) inventive JNK inhibitor sequence or chimeric peptide as defined above. Preferably, such nucleic acid sequences comprise at least 6 (contiguous) nucleic acids, which have a length sufficient to allow for specific hybridization. More preferably, such nucleic acid sequences comprise 6 to 38, even more preferably 6 to 30, and most preferably 6 to 20 or 6 to 10 (contiguous) nucleic acids.

"Stringent conditions" are sequence dependent and will be different in different circumstances. Generally, stringent conditions can be selected to be about 5° C. lower than the thermal melting point (TM) for the specific sequence at a defined ionic strength and pH. The TM is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C. As other factors may affect the stringency of hybridization (including, among others, base composition and size of the complementary strands), the presence of organic solvents and the extent of base mismatching, the combination of parameters is more important than the absolute measure of any one.

"High stringency conditions" may comprise the following, e.g. Step 1: Filters containing DNA are pretreated for 8 hours to overnight at 65° C. in buffer composed of 6*SSC, 50 mM Tris-HCl (pH 7.5), 1 mM EDTA, 0.02% PVP, 0.02% Ficoll, 0.02% BSA, and 500 µg/ml denatured salmon sperm DNA. Step 2: Filters are hybridized for 48 hours at 65° C. in the above prehybridization mixture to which is added 100 mg/ml denatured salmon sperm DNA and 5-20*10$^6$ cpm of $^{32}$P-labeled probe. Step 3: Filters are washed for 1 hour at 37° C. in a solution containing 2*SSC, 0.01% PVP, 0.01% Ficoll, and 0.01% BSA. This is followed by a wash in 0.1*SSC at 50° C. for 45 minutes. Step 4: Filters are autoradiographed. Other conditions of high stringency that may be used are well known in the art (see e.g. Ausubel et al., (eds.), 1993, Current Protocols in Molecular Biology, John Wiley and Sons, NY; and Kriegler, 1990, Gene Transfer and Expression, a Laboratory Manual, Stockton Press, NY).

"Moderate stringency conditions" can include the following: Step 1: Filters containing DNA are pretreated for 6 hours at 55° C. in a solution containing 6*SSC, 5*Denhardt's solution, 0.5% SDS and 100 mg/ml denatured salmon sperm DNA. Step 2: Filters are hybridized for 18-20 hours at 55° C. in the same solution with 5-20*10$^6$ cpm $^{32}$P-labeled probe added. Step 3: Filters are washed at 37° C. for 1 hour in a solution containing 2*SSC, 0.1% SDS, then washed twice for 30 minutes at 60° C. in a solution containing 1*SSC and 0.1% SDS. Step 4: Filters are blotted dry and exposed for autoradiography. Other conditions of moderate stringency that may be used are well-known in the art (see e.g. Ausubel et al., (eds.), 1993, Current Protocols in Molecular Biology, John Wiley and Sons, NY; and Kriegler, 1990, Gene Transfer and Expression, a Laboratory Manual, Stockton Press, NY).

Finally, "low stringency conditions" can include: Step 1: Filters containing DNA are pretreated for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 Mg/ml denatured salmon sperm DNA. Step 2: Filters are hybridized for 18-20 hours at 40° C. in the same solution with the addition of 0.02% PVP, 0.02% Ficoll, 0.2% BSA, 100 µg/ml salmon sperm DNA, 10% (wt/vol) dextran sulfate, and 5-20×106 cpm $^{32}$P-labeled probe. Step 3: Filters are washed for 1.5 hours at 55 C. in a solution containing 2×SSC, 25 mM Tris-HCl (pH 7.4), 5 mM EDTA, and 0.1% SDS. The wash solution is replaced with fresh solution and incubated an additional 1.5 hours at 60° C. Step 4: Filters are blotted dry and exposed for autoradiography. If necessary, filters are washed for a third time at 65-68° C. and reexposed to film. Other conditions of low stringency that may be used are well known in the art (e.g. as employed for cross-species hybridizations). See e.g. Ausubel et al., (eds.), 1993, CURRENT PROTOCOLS IN MOLECULAR BIOLOGY, John Wiley and Sons, NY; and Kriegler, 1990, GENE TRANSFER AND EXPRESSION, A LABORATORY MANUAL, Stockton Press, NY.

The nucleic acid sequences provided by the present invention can be used to express inventive peptides, i.e. an inventive JNK inhibitor sequence or an inventive chimeric peptide for analysis, characterization or therapeutic use; as markers for tissues in which the corresponding (inventive) peptides are preferentially expressed (either constitutively or at a particular stage of tissue differentiation or development or in disease states). Other uses for the nucleic acids include, e.g. molecular weight markers in gel electrophoresis-based analysis of nucleic acids.

According to a further embodiment of the present invention, expression vectors are also provided for recombinant expression of one or more inventive JNK inhibitor sequences and/or chimeric peptides as defined above. The term "expression vector" is used herein to designate either circular or linear DNA or RNA, which is either double-stranded or single-stranded. It further comprises at least one inventive nucleic acid to be transferred into a host cell or into a unicellular or multicellular host organism. The inventive expression vector preferably comprises an inventive nucleic acid encoding the inventive JNK inhibitor sequence or a fragment or a variant thereof, or the inventive chimeric peptide, or a fragment or a variant thereof. Additionally, an expression vector according to the present invention preferably comprises appropriate elements for supporting expression including various regulatory elements, such as enhancers/promoters from viral, bacterial, plant, mammalian, and other eukaryotic sources that drive expression of the inserted polynucleotide in host cells, such as insulators, boundary elements, LCRs (e.g. described by Blackwood and Kadonaga (1998), Science 281, 61-63) or matrix/scaffold attachment regions (e.g. described by Li, Harju and Peterson, (1999), Trends Genet. 15, 403-408). In some embodiments, the regulatory elements are heterologous (i.e. not the native gene promoter). Alternately, the necessary transcriptional and translational signals may also be supplied by the native promoter for the genes and/or their flanking regions.

The term "promoter" as used herein refers to a region of DNA that functions to control the transcription of one or more inventive nucleic acid sequences, and that is structurally identified by the presence of a binding site for DNA-dependent RNA-polymerase and of other DNA sequences, which interact to regulate promoter function. A functional expression promoting fragment of a promoter is a shortened or truncated promoter sequence retaining the activity as a promoter. Promoter activity may be measured by any assay known in the art (see e.g. Wood, de Wet, Dewji, and DeLuca, (1984), Biochem Biophys. Res. Commun. 124, 592-596; Seliger and McElroy, (1960), Arch. Biochem. Biophys. 88, 136-141) or commercially available from Promega®).

An "enhancer region" as used in the inventive expression vector, typically refers to a region of DNA that functions to increase the transcription of one or more genes. More specifically, the term "enhancer", as used herein, is a DNA regulatory element that enhances, augments, improves, or ameliorates expression of a gene irrespective of its location and orientation vis-à-vis the gene to be expressed, and may be enhancing, augmenting, improving, or ameliorating expression of more than one promoter.

Promoter/enhancer sequences as defined above for the inventive expression vector, may utilize plant, animal, insect, or fungus regulatory sequences. For example, promoter/enhancer elements can be used from yeast and other fungi (e.g. the GAL4 promoter, the alcohol dehydrogenase promoter, the phosphoglycerol kinase promoter, the alkaline phosphatase promoter). Alternatively, or in addition, they may include animal transcriptional control regions, e.g. (i) the insulin gene control region active within pancreatic β-cells (see e.g. Hanahan, et al., 1985. Nature 315: 115-122); (ii) the immunoglobulin gene control region active within lymphoid cells (see e.g. Grosschedl, et al., 1984, Cell 38: 647-658); (iii) the albumin gene control region active within liver (see e.g. Pinckert, et al., 1987. Genes and Dev 1: 268-276; (iv) the myelin basic protein gene control region active within brain oligodendrocyte cells (see e.g. Readhead, et al., 1987, Cell 48: 703-712); and (v) the gonadotropin-releasing hormone gene control region active within the hypothalamus (see e.g. Mason, et al., 1986, Science 234: 1372-1378), and the like.

Additionally, the inventive expression vector may comprise an amplification marker. This amplification marker may be selected from the group consisting of, e.g. adenosine deaminase (ADA), dihydrofolate reductase (DHFR), multiple drug resistance gene (MDR), ornithine decarboxylase (ODC) and N-(phosphonacetyl)-L-aspartate resistance (CAD). Amplification of the gene encoding the above defined proteins, i.e. the protein of interest (POI) and/or the inventive fusion protein, allows to increase the expression level of these proteins upon integration of the vector in a cell (Kaufman et al. (1985), Mol. Cell. Biol. 5, 1750-1759).

Exemplary expression vectors or their derivatives suitable for the present invention particularly include, e.g. human or animal viruses (e.g. vaccinia virus or adenovirus); insect viruses (e.g. baculovirus); yeast vectors; bacteriophage vectors (e.g. lambda phage); plasmid vectors and cosmid vectors.

The present invention additionally provides a variety of host-vector systems, which may be utilized to express the peptide coding sequence(s) of inventive nucleic acids as defined above. These include, but are not limited to: (i) mammalian cell systems that are infected with vaccinia virus, adenovirus, and the like; (ii) insect cell systems infected with baculovirus and the like; (iii) yeast containing yeast vectors or (iv) bacteria transformed with bacteriophage, DNA, plasmid DNA, or cosmid DNA. Depending upon the host-vector system utilized, any one of a number of suitable transcription and translation elements may be used.

Preferably, a host cell strain, suitable for such a host-vector system, may be selected that modulates the expression of inserted sequences of interest, or modifies or processes expressed peptides encoded by the sequences in the specific manner desired. In addition, expression from certain promoters may be enhanced in the presence of certain inducers in a selected host strain; thus facilitating control of the expression of a genetically-engineered peptide. Moreover, different host cells possess characteristic and specific mechanisms for the translational and post-translational processing and modification (e.g. glycosylation, phosphorylation, and the like) of expressed peptides. Appropriate cell lines or host systems may thus be chosen to ensure the desired modification and processing of the foreign peptide is achieved. For example, peptide expression within a bacterial system can be used to produce an non-glycosylated core peptide; whereas expression within mammalian cells ensures "native" glycosylation of a heterologous peptide.

The present invention further provides antibodies directed against the inventive JNK inhibitor sequences and/or inventive chimeric peptides. Furthermore, efficient means for production of antibodies specific for JNK inhibitor sequences according to the present invention, or for inventive chimeric peptides containing such an inhibitor sequence, are provided.

According to the invention, JNK inhibitor sequences and/or inventive chimeric peptides, as well as, fragments, variants or derivatives thereof, may be utilized as immunogens to generate antibodies that immunospecifically bind these peptide components. Such antibodies include, e.g. polyclonal, monoclonal, chimeric, single chain, Fab fragments and a Fab expression library. In a specific embodiment the present invention provides antibodies to inventive chimeric peptides or to JNK inhibitor sequences as defined above. Various procedures known within the art may be used for the production of these inventive antibodies.

By way of example, various host animals may be immunized for production of polyclonal antibodies by injection with any inventive chimeric peptide or JNK inhibitor sequence as defined above. Various adjuvants may be used thereby to increase the immunological response which include, but are not limited to, Freund's (complete and incomplete) adjuvant, mineral gels (e.g. aluminum hydroxide), surface active substances (e.g. lysolecithin, pluronic polyols, polyanions, peptides, oil emulsions, dinitrophenol, etc.), CpG, polymers, Pluronics, and human adjuvants such as Bacille Calmette-Guerin and *Corynebacterium parvum*.

For preparation of monoclonal antibodies directed towards an inventive chimeric peptide or JNK inhibitor sequence as defined above, any technique may be utilized that provides for the production of antibody molecules by continuous cell line culture. Such techniques include, but are not limited to, the hybridoma technique (see Kohler and Milstein, 1975. Nature 256: 495-497); the trioma technique; the human B-cell hybridoma technique (see Kozbor, et al., 1983, Immunol Today 4: 72) and the EBV hybridoma technique to produce human monoclonal antibodies (see Cole, et al., 1985. In: Monoclonal Antibodies and Cancer Therapy, Alan R. Liss, Inc., pp. 77-96). Human monoclonal antibodies may be utilized in the practice of the present invention and may be produced by the use of human hybridomas (see Cote, et al., 1983. Proc Natl Acad Sci USA 80: 2026-2030) or by transforming human B-cells with Epstein Barr Virus in vitro (see Cole, et al., 1985. In: Monoclonal Antibodies and Cancer Therapy (Alan R. Liss, Inc., pp. 77-96).

According to the invention, techniques can be adapted for the production of single-chain antibodies specific to the inventive JNK inhibitor sequences and/or inventive chimeric peptides (see e.g. U.S. Pat. No. 4,946,778). In addition, methods can be adapted for the construction of Fab expression libraries (see e.g. Huse et al., 1989. Science 246: 1275-1281) to allow rapid and effective identification of monoclonal Fab fragments with the desired specificity for these inventive JNK inhibitor sequences and/or inventive chimeric peptides as defined above. Non-human antibodies can be "humanized" by techniques well known in the art (see e.g. U.S. Pat. No. 5,225,539). Antibody fragments that contain the idiotypes to a JNK inhibitor sequences and/or inventive chimeric peptide may be produced by techniques known in the art including, e.g. (i) a $F(ab')_2$ fragment produced by pepsin digestion of an antibody molecule; (ii) a Fab fragment generated by reducing the disulfide bridges of an $F(ab')_2$ fragment; (iii) a Fab fragment generated by the treatment of the antibody molecule with papain and a reducing agent and (iv) Fv fragments.

In one embodiment of this invention, methods for the screening of inventive antibodies that possess the desired specificity include, but are not limited to, enzyme-linked immunosorbent assay (ELISA) and other immunologically-mediated techniques known within the art. In a specific embodiment, selection of antibodies that are specific to a particular epitope of an inventive JNK inhibitor sequence and/or an inventive chimeric peptide (e.g. a fragment thereof typically comprising a length of from 5 to 20, preferably 8 to 18 and most preferably 8 to 11 amino acids) is facilitated by generation of hybridomas that bind to the fragment of an inventive JNK inhibitor sequence and/or an inventive chimeric peptide possessing such an epitope. These antibodies that are specific for an epitope as defined above are also provided herein.

The inventive antibodies may be used in methods known within the art referring to the localization and/or quantification of an inventive JNK inhibitor sequence (and/or correspondingly to an inventive chimeric peptide), e.g. for use in measuring levels of the peptide within appropriate physiological samples, for use in diagnostic methods, or for use in imaging the peptide, and the like.

The inventive JNK inhibitor sequences, chimeric peptides, and/or nucleic acids of the invention can be formulated in pharmaceutical compositions, also encompassed herewith. These compositions may comprise, in addition to one of these substances, a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal or patch routes.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as required. Whether it is a polypeptide, peptide, or nucleic acid molecule, other pharmaceutically useful compound according to the present invention that is to be given to an individual, administration is preferably in a "prophylactically effective amount or a "therapeutically effective amount" (as the case may be), this being sufficient to show benefit to the individual. The actual amount administered, and rate and time-course of administration, will depend on the nature and severity of what is being treated.

Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in REMINGTON'S PHARMACEUTICAL SCIENCES, 16th edition, Osol, A. (ed), 1980.

Alternatively, targeting therapies may be used to deliver the inventive JNK inhibitor sequences, chimeric peptides, and nucleic acids of the invention more specifically to certain types of cell, by the use of targeting systems such as (a targeting) antibody or cell specific ligands. Antibodies used for targeting are typically specific for cell surface proteins of cells associated with any of the diseases as defined below. By way of example, these antibodies may be directed to cell surface antibodies such as e.g. B cell-associated surface proteins such as MHC class II DR protein, CD18 (LFA-1 beta chain), CD45RO, CD40 or Bgp95, or cell surface proteins selected from e.g. CD2, CD2, CD4, CD5, CD7, CD8, CD9, CD10, CD13, CD16, CD19, CD20, CD21, CD22, CD23, CD24, CD25, CD30, CD33, CD34, CD38, CD39, CD4, CD43, CD45, CD52, CD56, CD68, CD71, CD138, etc. Targeting constructs may be typically prepared by covalently binding the inventive JNK inhibitor sequences, chimeric peptides, and nucleic acids to an antibody specific for a cell surface protein or by binding to a cell specific ligand. Proteins may e.g. be bound to such an antibody or may be attached thereto by a peptide bond or by chemical coupling, crosslinking, etc. The targeting therapy may then be carried out by administering the targeting construct in a pharmaceutically efficient amount to a patient by any of the administration routes as defined below, e.g. intraperitoneal, nasal, intravenous, oral and patch delivery routes. Preferably, the inventive JNK inhibitor sequences, chimeric peptides, or nucleic acids of the invention attached to the targeting antibodies or cell specific ligands as defined above, may be released in vitro or in vivo, e.g. by hydrolysis of the covalent bond, by peptidases or by any other suitable method. Alternatively, if the inventive JNK inhibitor sequences, chimeric peptides, or nucleic acids of the invention are attached to a small cell specific ligand, release of the ligand may not be carried out. If present at the cell surface, the inventive chimeric peptides may enter the cell upon the activity of its trafficking sequence. Targeting may be desirable for a variety of reasons; for example if the inventive JNK inhibitor sequences, chimeric peptides, and nucleic acids of the invention are unacceptably toxic or if it would otherwise require a too high dosage.

Instead of administering the inventive JNK inhibitor sequences and/or chimeric peptides of the invention directly, they could be produced in the target cells by expression from an encoding gene introduced into the cells, e.g. from a viral vector to be administered. The viral vector typically encodes the inventive JNK inhibitor sequences and/or chimeric peptides of the invention. The vector could be targeted to the specific cells to be treated. Moreover, the vector could contain regulatory elements, which are switched on more or less selectively by the target cells upon defined regulation. This technique represents a variant of the VDEPT technique (virus-directed enzyme prodrug therapy), which utilizes mature proteins instead of their precursor forms.

Alternatively, the inventive JNK inhibitor sequences and/ or chimeric peptides could be administered in a precursor form by use of an antibody or a virus. The inventive JNK inhibitor sequences and/or chimeric peptides may then be converted into the active form by an activating agent produced in, or targeted to, the cells to be treated. This type of approach is sometimes known as ADEPT (antibody-directed enzyme prodrug therapy) or VDEPT (virus-directed enzyme prodrug therapy); the former involving targeting the activating agent to the cells by conjugation to a cell-specific antibody, while the latter involves producing the activating agent, e.g. a JNK inhibitor sequence or the chimeric peptide, in a vector by expression from encoding DNA in a viral vector (see for example, EP-A-415731 and WO 90/07936).

The present invention further encompasses the use of inventive JNK inhibitor sequences, inventive chimeric peptides and/or inventive nucleic acid sequences, for preparing a pharmaceutical composition, e.g. as defined above, for preventing and/or treating cell-proliferative disorders associated with JNK activation in a subject ("JNK associated disorder"). Typically, such a pharmaceutical composition used according to the present invention includes as an active component, e.g.: (i) any one or more of the inventive JNK inhibitor sequences and/or inventive chimeric peptides, and/or variants, fragments or derivatives thereof; and/or (ii) nucleic acids encoding an inventive JNK inhibitor sequence and/or an inventive chimeric peptide and/or variants or fragments thereof, and/or (iii) cells comprising any one or more of the inventive JNK inhibitor sequences and/or inventive chimeric peptides, and/ or variants, fragments or derivatives thereof and/or (iv) cells transfected with a vector and/or nucleic acids encoding an inventive JNK inhibitor sequence and/or an inventive chimeric peptide and/or variants or fragments thereof.

Prevention and/or treatment according to the present invention typically includes administration of an inventive pharmaceutical composition as defined above. The term "modulate" includes the suppression of expression of JNK when it is over-expressed. It also includes suppression of phosphorylation of c-jun, ATF2 or NFAT4, for example, by using a peptide of any one or more of SEQ ID NOs: 1-4 and/or 9-12 as a competitive inhibitor of the natural c-jun, ATF2 and NFAT4 binding site in a cell. The term "modulate" also includes suppression of hetero- and homomeric complexes of transcription factors made up of c-jun, ATF2, or NFAT4 and their related partners, such as for example the AP-1 complex that is made up of c-jun, AFT2 and c-fos. When a cell proliferative disorder is associated with JNK overexpression, such suppressive JNK inhibitor sequences can be introduced to a cell. In some instances, "modulate" may include the increase of JNK expression, for example by use of an IB peptide-specific antibody that blocks the binding of an IB-peptide to JNK, thus preventing JNK inhibition by the IB-related peptide.

Prevention and/or treatment of a subject with the inventive pharmaceutical composition as disclosed above may be typically accomplished by administering (in vivo) an ("therapeutically effective") amount of said pharmaceutical composition to a subject, wherein the subject may be e.g. any mammal, e.g. a human, a primate, mouse, rat, dog, cat, cow, horse or pig. The term "therapeutically effective" means that the active component of the pharmaceutical composition is of sufficient quantity to ameliorate the JNK associated disorder.

The term "cell-proliferative disorder" or "JNK associated disorder" as used above typically denotes malignant as well as non-malignant cell populations in vivo and in vitro that often appear to differ morphologically and functionally from the surrounding tissue and which are typically characterized by aberrant levels of JNK. An "aberrant level of JNK" is intended to mean an increased or decreased level of JNK in a part of the subject to be treated relative to that present in an analogous unaffected part of a subject not having the disorder.

For example, the inventive pharmaceutical compositions may be useful in preventing, and/or treating malignancies of the various organ systems, in which activation of JNK has often been demonstrated, e.g. lung, breast, lymphoid, gastrointestinal, and genito-urinary tract as well as adenocarcinomas which include malignancies such as most colon cancers, renal-cell carcinoma, prostate cancer, non-small cell carcinoma of the lung, cancer of the small intestine and cancer of the esophagus. Leukemia, disorders or pathophysiologies associated with oncogenic transformation as well as cancers with Bcr-Abl oncogenic transformations that clearly require activation of JNK are also included.

The inventive pharmaceutical compositions are also applicable in preventing and/or treating non-malignant or immunological-related cell proliferative diseases such as psoriasis, pemphigus vulgaris, Behcet's syndrome, acute respiratory distress syndrome (ARDS), ischemic heart disease, post-dialysis syndrome, rheumatoid arthritis, acquired immune deficiency syndrome, vasculitis, septic shock and other types of acute inflammation, and lipid histiocytosis. Especially preferred are immunopathological disorders. Essentially, any disorder, which is etiologically linked to JNK kinase activity, is considered susceptible to prevention or treatment, e.g. disorders or pathophysiologies associated with activation of JNK in a cell or cells as defined above, e.g. restenosis, hearing loss, ear trauma, ischemia, stroke and/or disorders or pathophysiologies associated with maturation and differentiation of immune cells, reperfusion injuries, hypoxia, apoptosis-related diseases (e.g. occurring in viral infections (e.g. AIDS), autoimmune diseases, neurodegenerative disorders (e.g. stroke, brain trauma, spinal cord injury, amyotrophic lateral sclerosis (ALS), Huntington's disease, Alzheimer's disease, and Parkinson's disease), cardiovascular disease, osteoporosis and aging), response to stressful stimuli, and with secondary effects due to treatment with e.g. proinflammatory cytokines. The inventive pharmaceutical composition may also be used to treat or prevent effects associated with diabetes or with cellular shear stress, such as in pathological states induced by arterial hypertension, including heart and cardiac hypertrophy and arteriosclerotic lesions, and at bifurcations of blood vessels, and the like, by ionizing radiation, as used in radiotherapy and ultraviolet light (UV lights), by free radicals, DNA damaging agents, including chemotherapeutic drugs, by ischemia/reperfusion injuries, by hypoxia; and/or hypo-and hyperthermia. Finally, in the context of the above mentioned diseases, disorders or pathophysiologies, the inventive pharmaceutical composition may be used to inhibit expression of genes whose expression increases in the presence of an active JNK polypeptide. These genes and gene products typically include e.g. proinflammatory cytokines. Such cytokines are found in all forms of inflammatory, auto-inflammatory, immune and autoimmune diseases, degenerative diseases, myopathies, cardiomyopathies, and graft rejection.

The inventive JNK inhibitor sequences, inventive chimeric peptides or inventive nucleic acid sequences further may be used in any situation in which inhibition of JNK activity is desired, since JNKs and all its isoforms participate in the development and establishment of pathological states or in pathways thereof. Such use can include in vitro applications, ex vivo, and in vivo applications.

Accordingly, inventive nucleic acids as defined above may be utilized in a specific embodiment of the present invention to modulate activated JNK signaling pathways by way of gene therapy, preferably for treating one of the conditions, diseases, and/or disorders as defined above. In this context, gene therapy refers to therapy that is performed by administration of a specific inventive nucleic acid to a subject, e.g. by way of a pharmaceutical composition as defined above, wherein the inventive nucleic acid(s) exclusively comprise(s) L-amino acids. In this embodiment of the present invention, the nucleic acid produces its encoded peptide(s), which then serve(s) to exert a therapeutic effect by modulating function of the disease or disorder. Any of the methods relating to gene therapy available within the art may be used in the practice of the present invention (see e.g. Goldspiel, et al., 1993. Clin Pharm 12: 488-505).

In a preferred embodiment, the inventive nucleic acid used for gene therapy is part of an expression vector expressing any one or more of the inventive IB-related peptides, i.e. an inventive JNK inhibitor sequence and/or an inventive chimeric peptide, or fragments or derivatives thereof, within a suitable host. In a specific embodiment, such an expression vector possesses a promoter that is operably-linked to coding region(s) of a JNK inhibitor sequence. The promoter may be defined as above, e.g. inducible or constitutive, and, optionally, tissue-specific.

In another specific embodiment, a inventive nucleic acid molecule is used for gene therapy, in which the coding sequences of the inventive nucleic acid molecule (and any other desired sequences thereof) are flanked by regions that promote homologous recombination at a desired site within the genome, thus providing for intra-chromosomal expression of nucleic acids (see e.g. Koller and Smithies, 1989. Proc Natl Acad Sci USA 86: 8932-8935).

Delivery of the inventive nucleic acid for the into a patient purpose of gene therapy may be either direct (i.e. the patient is directly exposed to the nucleic acid or nucleic acid-containing vector) or indirect (i.e. cells are first transformed with the nucleic acid in vitro, then transplanted into the patient). These two approaches are known, respectively, as in vivo or ex vivo gene therapy. In a specific embodiment of the present invention, a nucleic acid is directly administered in vivo, where it is expressed to produce the encoded product. This may be accomplished by any of numerous methods known in the art including, e.g. constructing the nucleic acid as part of an appropriate nucleic acid expression vector and administering the same in a manner such that it becomes intracellular (e.g. by infection using a defective or attenuated retroviral or other viral vector; see U.S. Pat. No. 4,980,286); directly injecting naked DNA; using microparticle bombardment (e.g. a "GeneGun"; Biolistic, DuPont); coating the nucleic acids with lipids; using associated cell-surface receptors/transfecting agents; encapsulating in liposomes, microparticles, or microcapsules; administering it in linkage to a peptide that is known to enter the nucleus; or by administering it in linkage to a ligand predisposed to receptor-mediated endocytosis (see e.g. Wu and Wu, 1987. J Biol Chem 262:

4429-4432), which can be used to "target" cell types that specifically express the receptors of interest, etc.

An additional approach to gene therapy in the practice of the present invention involves transferring a gene into cells in in vitro tissue culture by such methods as electroporation, lipofection, calcium phosphate-mediated transfection, viral infection, or the like. Generally, the method of transfer includes the concomitant transfer of a selectable marker to the cells. The cells are then placed under selection pressure (e.g. antibiotic resistance) so as to facilitate the isolation of those cells that have taken up, and are expressing, the transferred gene. Those cells are then delivered to a patient. In a specific embodiment, prior to the in vivo administration of the resulting recombinant cell, the nucleic acid is introduced into a cell by any method known within the art including e.g. transfection, electroporation, microinjection, infection with a viral or bacteriophage vector containing the nucleic acid sequences of interest, cell fusion, chromosome-mediated gene transfer, microcell-mediated gene transfer, spheroplast fusion, and similar methods that ensure that the necessary developmental and physiological functions of the recipient cells are not disrupted by the transfer. See e.g. Loeffler and Behr, 1993. Meth Enzymol 217: 599-618. The chosen technique should provide for the stable transfer of the nucleic acid to the cell, such that the nucleic acid is expressible by the cell. Preferably, the transferred nucleic acid is heritable and expressible by the cell progeny.

In preferred embodiments of the present invention, the resulting recombinant cells may be delivered to a patient by various methods known within the art including, e.g. injection of epithelial cells (e.g. subcutaneously), application of recombinant skin cells as a skin graft onto the patient, and intravenous injection of recombinant blood cells (e.g. hematopoietic stem or progenitor cells). The total amount of cells that are envisioned for use depend upon the desired effect, patient state, and the like, and may be determined by one skilled within the art. Cells into which a nucleic acid can be introduced for purposes of gene therapy encompass any desired, available cell type, and may be xenogeneic, heterogeneic, syngeneic, or autogeneic. Cell types include, but are not limited to, differentiated cells such as epithelial cells, endothelial cells, keratinocytes, fibroblasts, muscle cells, hepatocytes and blood cells, or various stem or progenitor cells, in particular embryonic heart muscle cells, liver stem cells (International Patent Publication WO 94/08598), neural stem cells (Stemple and Anderson, 1992, Cell 71: 973-985), hematopoietic stem or progenitor cells, e.g. as obtained from bone marrow, umbilical cord blood, peripheral blood, fetal liver, and the like. In a preferred embodiment, the cells utilized for gene therapy are autologous to the patient.

According to a further embodiment, the inventive JNK inhibitor sequences, inventive chimeric peptides, inventive nucleic acid sequences or antibodies to inventive JNK inhibitor sequences or to inventive chimeric peptides may be utilized in (in vitro) assays (e.g. immunoassays) to detect, prognose, diagnose, or monitor various conditions, diseases, and/or disorders as defined above, or monitor the treatment thereof. The immunoassay may be performed by a method comprising contacting a sample derived from a patient with an antibody to an inventive JNK inhibitor sequence, an inventive chimeric peptide, or an inventive nucleic acid sequence, under conditions such that immunospecific-binding may occur, and subsequently detecting or measuring the amount of any immunospecific-binding by the antibody. In a specific embodiment, an antibody specific for an inventive JNK inhibitor sequence, inventive chimeric peptide or inventive nucleic acid sequence may be used to analyze a tissue or serum sample from a patient for the presence of JNK or a JNK inhibitor sequence; wherein an aberrant level of JNK is indicative of a diseased condition. The immunoassays that may be utilized include, but are not limited to, competitive and non-competitive assay systems using techniques such as Western Blots, radioimmunoassays (RIA), enzyme linked immunosorbent assay (ELISA), "sandwich" immunoassays, immunoprecipitation assays, precipitin reactions, gel diffusion precipitin reactions, immunodiffusion assays, agglutination assays, fluorescent immunoassays, complement-fixation assays, immunoradiometric assays, and protein-A immunoassays, etc. Alternatively, (in vitro) assays may be performed by delivering the inventive JNK inhibitor sequences, inventive chimeric peptides, inventive nucleic acid sequences or antibodies to inventive JNK inhibitor sequences or to inventive chimeric peptides to target cells typically selected from e.g. cultured animal cells, human cells or micro-organisms, and to monitor the cell response by biophysical methods typically known to a skilled person. The target cells typically used therein may be cultured cells (in vitro) or in vivo cells, i.e. cells composing the organs or tissues of living animals or humans, or microorganisms found in living animals or humans.

The present invention additionally provides kits for diagnostic or therapeutic use that include one or more containers containing inventive JNK inhibitor sequences, inventive chimeric peptides, inventive nucleic acid sequences and/or antibodies to inventive JNK inhibitor sequences or to inventive chimeric peptides, e.g. an anti-JNK inhibitor sequence antibody and, optionally, a labeled binding partner to the antibody. The label incorporated thereby into the antibody may include, but is not limited to, a chemiluminescent, enzymatic, fluorescent, colorimetric or radioactive moiety. In another specific embodiment, kits for diagnostic use are provided which comprise one or more containers containing nucleic acids that encode, or alternatively, that are the complement to, an inventive JNK inhibitor sequence and/or an inventive chimeric peptide, optionally, a labeled binding partner to these nucleic acids, are also provided. In an alternative specific embodiment, the kit may comprise, in one or more containers, a pair of oligonucleotide primers (e.g. each 6-30 nucleotides in length) that are capable of acting as amplification primers for polymerase chain reaction (PCR; see e.g. Innis, et al., 1990. PCR PROTOCOLS, Academic Press, Inc., San Diego, Calif.), ligase chain reaction, cyclic probe reaction, and the like, or other methods known within the art used in context with the inventive nucleic acids. The kit may, optionally, further comprise a predetermined amount of a purified inventive JNK inhibitor sequence, an inventive chimeric peptide, or nucleic acids encoding these, for use as a diagnostic, standard, or control in the assays.

The present invention is not to be limited in scope by the specific embodiments described herein. Indeed, various modifications of the invention in addition to those described herein will become apparent to those skilled in the art from the foregoing description and accompanying figures. Such modifications fall within the scope of the appended claims.

Various publications are cited herein, the disclosures of which are incorporated by reference in their entirety.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting. Other features and advantages of the invention will be apparent from the following detailed description and claims.

DESCRIPTION OF FIGURES

FIGS. 1A-C are diagrams showing alignments of conserved JBD domain regions in the indicated transcription factors. JNK inhibitor sequences were identified by inspecting these sequence alignments. The results of this alignment are exemplarily shown in FIGS. 1A-1C. FIG. 1A depicts the region of highest homology between the JBDs of IB1 (SEQ ID NO: 13, IB2 (SEQ ID NO: 14), c-Jun (SEQ ID NO: 15) and ATF2 (SEQ ID NO: 16). Panel B depicts the amino acid sequence of the JBDs of L-IB1(s) (SEQ ID NO: 1) and L-IB1 (SEQ ID NO: 17) for comparative reasons. Fully conserved residues are indicated by asterisks, while residues changed to Ala in the GFP-JBD$_{23mut}$ vector are indicated by open circles. FIG. 1C shows the amino acid sequences of chimeric proteins (SEQ ID NOS 5, 9, 23, 6, 11 and 25, respectively, in order of appearance) that include a JNK inhibitor sequence and a trafficking sequence. In the example shown, the trafficking sequence is derived from the human immunodeficiency virus (HIV) TAT polypeptide, and the JNK inhibitor sequence is derived from an IB1(s) polypeptide. Human, mouse, and rat sequences are identical in Panels B and C.

FIG. 2 is a diagram showing sequences of generic TAT-IB fusion peptides from human, mouse and rat (SEQ ID NOS 21, 149, 24, 22, 150 and 26, respectively, in order of appearance).

EXAMPLES

Example 1

Identification of JNK Inhibitor Sequences

Figure 3:
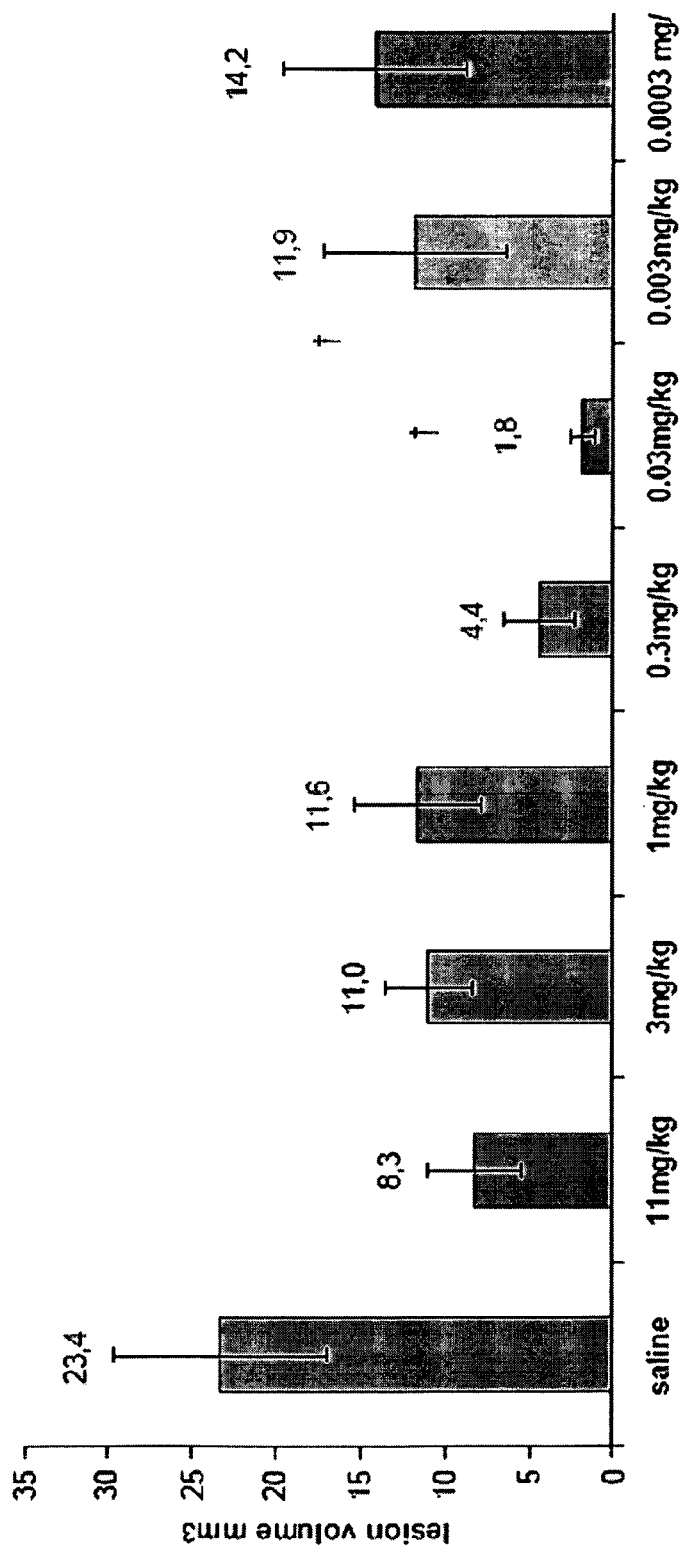
FIG. 3 depicts the results from the evaluation of the neuroprotection against focal cerebral ischemia in a permanent MCAO model. Determination of the efficacy of the protection was carried out at different doses (see FIG. 3). As can be seen from FIG. 3, at least doses of 11 mg/kg, 3 mg/kg, 0.3 mg/kg and 0.03 mg/kg, contribute to a cerebral protection. The best protection is observed at the dose of 0.03 mg/kg.

Amino acid sequences important for efficient interaction with JNK were identified by sequence alignments between known JBDs. A sequence comparison between the JBDs of IB1 [SEQ ID NO: 13], IB2 [SEQ ID NO: 14], c-Jun [SEQ ID NO: 15] and ATF2 [SEQ ID NO: 16] defined a weakly conserved 8 amino acid sequence (FIG. 1A). Since the JBDs of IB1 and IB2 are approximately 100 fold as efficient as c-Jun or ATF2 in binding JNK (Dickens et al. Science 277: 693 (1997), it was reasoned that conserved residues between IB1 and IB2 must be important to confer maximal binding. The comparison between the JBDs of IB1 and IB2 defined two blocks of seven and three amino acids that are highly conserved between the two sequences.

These two blocks are contained within a peptide sequence of 19 amino acids in L-IB1(s) [SEQ ID NO: 1] and are also shown for comparative reasons in a 23 aa peptide sequence derived from IB1 [SEQ ID NO: 17]. These sequences are shown in FIG. 1B, dashes in the L-IB1 sequence indicate a gap in the sequence in order to align the conserved residues with L-IB1(s).

Example 2

Preparation of JNK Inhibitor Fusion Proteins

Inventive JNK inhibitor fusion proteins according to SEQ ID NO: 9 were synthesized by covalently linking the C-terminal end of SEQ ID NO: 1 to a N-terminal 10 amino acid long carrier peptide derived from the HIV-TAT4g 57 (Vives et al., J. Biol. Chem. 272: 16010 (1997)) according to SEQ ID NO: 5 via a linker consisting of two proline residues. This linker was used to allow for maximal flexibility and prevent unwanted secondary structural changes. The basic constructs were also prepared and designated L-IB1(s) (SEQ ID NO: 1) and L-TAT [SEQ ID NO: 5], respectively.

All-D retro-inverso peptides according to SEQ ID NO: 11 were synthesized accordingly. The basic constructs were also prepared and designated D-IB1(s) [SEQ ID NO: 2] and D-TAT [SEQ ID NO: 6], respectively.

All inventive D and L fusion peptides according to SEQ ID NOs: 9, 10, 11 and 12 were produced by classical Fmock synthesis and further analysed by Mass Spectrometry. They were finally purified by HPLC. To determine the effects of the proline linker, two types of TAT peptide were produced one with and one without two prolines. The addition of the two prolines did not appear to modify the entry or the localization of the TAT peptide inside cells. Generic peptides showing the conserved amino acid residues are given in FIG. 2.

Example 3

Inhibition of Cell Death JBD19

Effects of the 19 aa long JBD sequence of IB1(s) on JNK biological activities were studied. The 19 aa sequence was linked N-terminal to the Green Fluorescent Protein (GFP JBD19 construct), and the effect of this construct on pancreatic β-cell apoptosis induced by IL1 was evaluated. This mode of apoptosis was previously shown to be blocked by transfection with $JBD_{1-280}$ whereas specific inhibitors of ERK1/2 or p38 did not protect (see Ammendrup et al., supra).

Oligonucleotides corresponding to JBD19 and comprising a conserved sequence of 19 amino acids as well as a sequence mutated at the fully conserved regions were synthesized and directionally inserted into the EcoRI and SalI sites of the pEGFP-N1 vector encoding the Green Fluorescent Protein (GFP) (from Clontech). Insulin producing βTC-3 cells were cultured in RPMI 1640 medium supplemented with 10% Fetal Calf Serum, 100 µg/mL Streptomycin, 100 units/mL Penicillin and 2 mM Glutamine. Insulin producing βTC-3 cells were transfected with the indicated vectors and IL-1β (10 ng/mL) was added to the cell culture medium. The number of apoptotic cells was counted at 48 hours after the addition of IL-1β using an inverted fluorescence microscope. Apoptotic cells were discriminated from normal cells by the characteristic "blebbing out" of the cytoplasm and were counted after two days.

GFP is Green Fluorescent protein expression vector used as a control; JBD19 is the vector expressing a chimeric GFP linked to the 19 aa sequence derived from the JBD of IB1; JBD19Mut is the same vector as GFP-JBD19, but with a JBD mutated at four conserved residues shown as FIG. 1B; and $JBD_{1-280}$ is the GFP vector linked to the entire JBD (aa 1-280). The GFP-JBD19 expressing construct prevented IL-1 β induced pancreatic β-cell apoptosis as efficiently as the entire $JBD_{1-280}$.

As additional controls, sequences mutated at fully conserved IB1(s) residues had greatly decreased ability to prevent apoptosis.

Example 4

Cellular Import of TAT-IB1(s) Peptides

The ability of the L- and D-enantiomeric forms of TAT and inventive TAT-IB1(s) peptides ("TAT-IB peptides") to enter cells was evaluated. L-TAT, D-TAT, inventive L-TAT-IB1(s), and inventive D-TAT-IB1(s) peptides [SEQ ID NOs: 5, 6, 9 and 12, respectively] were labeled by N-terminal addition of a glycine residue conjugated to fluorescein. Labeled peptides (1 µM) were added to βTC-3 cell cultures, which were maintained as described in Example 3. At predetermined times cells were washed with PBS and fixed for five minutes in ice-cold methanol-acetone (1:1) before being examined under a fluorescence microscope. Fluorescein-labeled BSA (1 µM, 12 moles/mole BSA) was used as a control. Results demonstrated that all the above fluorescein labeled peptides had efficiently and rapidly (less than five minutes) entered cells once added to the culture medium. Conversely, fluorescein labeled bovine serum albumin (1 µM BSA, 12 moles fluorescein/mole BSA) did not enter the cells.

A time course study indicated that the intensity of the fluorescent signal for the L-enantiomeric peptides decreased by 70% following a 24 hours period. Little to no signal was present at 48 hours. In contrast, D-TAT and inventive D-TAT-IB1(s) were extremely stable inside the cells.

Fluorescent signals from these all-D retro-inverso peptides were still very strong 1 week later, and the signal was only slightly diminished at 2 weeks post treatment.

Example 5

In Vitro Inhibition of c-JUN, ATF2 and Elk1 Phosphorylation

The effects of the peptides on JNKs-mediated phosphorylation of their target transcription factors were investigated in vitro. Recombinant and non activated JNK1, JNK2 and JNK3 were produced using a TRANSCRIPTION AND TRANSLATION rabbit reticulocyte lysate kit (Promega) and used in solid phase kinase assays with c-Jun, ATF2 and Elk1, either alone or fused to glutathione-S-transferase (GST), as substrates. Dose response studies were performed wherein inventive L-TAT or L-TAT-IB1(s) peptides (0-25 µM) were mixed with the recombinant JNK1, JNK2, or JNK3 kinases in reaction buffer (20 mM Tris-acetate, 1 mM EGTA, 10 mM p-nitrophenyl-phosphate (pNPP), 5 mM sodium pyrophosphate, 10 mM p-glycerophosphate, 1 mM dithiothreitol) for 20 minutes. The kinase reactions were then initiated by the addition of 10 mM $MgCl_2$ and 5 pCi $^{33}$P-γ-dATP and 1 µg of either GST-Jun (aa 1-89), GST-AFT2 (aa 1-96) or GST-ELK1 (aa 307-428). GST-fusion proteins were purchased from Stratagene (La Jolla, Calif.).

Ten µL of glutathione-agarose beads were also added to the mixture. Reaction products were then separated by SDS-PAGE on a denaturing 10% polyacrylamide gel. Gels were dried and subsequently exposed to X-ray films (Kodak). Nearly complete inhibition of c-Jun, ATF2 and Elk1 phosphorylation by JNKs was observed at inventive TAT-IB(s) peptide doses as low as 2.5 µM. However, a marked exception was the absence of TAT-IB(s) inhibition of JNK3 phosphorylation of Elk1.

Overall, the inventive TAT-IB1(s) peptide showed superior effects in inhibiting JNK family phosphorylation of their target transcription factors. The ability of D-TAT, inventive D-TAT-IB1(s) and inventive L-TAT-IB1(s) peptides (0-250 µM dosage study) to inhibit GST-Jun (aa 1-73) phosphorylation by recombinant JNK1, JNK2, and JNK3 by were analyzed as described above. Overall, D-TAT-IB1(s) peptide decreased JNK-mediated phosphorylation of c-Jun, but at levels approximately 10-20 fold less efficiently than L-TAT-IB1(s).

Example 6

Inhibition of c-JUN Phosphorylation by Activated JNKs

The effects of the L-TAT or inventive L-TAT-IB1(s) peptides on JNKs activated by stressful stimuli were evaluated using GST-Jun to pull down JNKs from UV-light irradiated HeLa cells or IL-1 β treated PTC cells. PTC cells were cultured as described above. HeLa cells were cultured in DMEM medium supplemented with 10% Fetal Calf Serum, 100 µg/mL Streptomycin, 100 units/ml Penicillin and 2 mM Glutamine. One hour prior to being used for cell extract preparation, PTC cells were activated with IL-1 β as described above, whereas HeLa cells were activated by UV-light (20 J/m²). Cell extracts were prepared from control, UV-light irradiated HeLa cells and IL-1β treated βTC-3 cells by scraping the cell cultures in lysis buffer (20 mM Tris-acetate, 1 mM EGTA, 1% Triton X-100, 10 mM p-nitrophenyl-phosphate, 5 mM sodium pyrophosphate, 10 mMP-glycerophosphate, 1 mM dithiothreitol). Debris was removed by centrifugation for five minutes at 15,000 rpm in an SS-34 Beckman rotor. One-hundred μg extracts were incubated for one hour at room temperature with one μg GST-jun (amino acids 1-89) and 10 μL of glutathione-agarose beads (Sigma). Following four washes with the scraping buffer, the beads were resuspended in the same buffer supplemented with L-TAT or inventive L-TAT-IB1(s) peptides (25 μM) for 20 minutes. Kinase reactions were then initiated by addition of 10 mM MgCl₂ and 5 pCi ³³P-γ-dATP and incubated for 30 minutes at 30° C.

Reaction products were then separated by SDS-PAGE on a denaturing 10% polyacrylamide gel. Gels were dried and subsequently exposed to X-ray films (Kodak). The inventive TAT-IB(s) peptides efficiently prevented phosphorylation of c-Jun by activated JNKs in these experiments.

Example 7

In Vivo Inhibition of c-JUN Phosphorylation by Inventive TAT-IB(s) Peptides

To determine whether the inventive cell-permeable peptides could block JNK signaling in vivo, we used a heterologous GAL4 system. HeLa cells, cultured as described above, were co-transfected with the 5×GAL-LUC reporter vector together with the GAL-Jun expression construct (Stratagene) comprising the activation domain of c-Jun (amino acids 1-89) linked to the GAL4 DNA-binding domain. Activation of JNK was achieved by the co-transfection of vectors expressing the directly upstream kinases MKK4 and MKK7 (see Whitmarsh et al., Science 285: 1573 (1999)). Briefly, 3×10⁵ cells were transfected with the plasmids in 3.5-cm dishes using DOTAP (Boehringer Mannheim) following instructions from the manufacturer. For experiments involving GAL-Jun, 20 ng of the plasmid was transfected with 1 μg of the reporter plasmid pFR-Luc (Stratagene) and 0.5 μg of either MKK4 or MKK7 expressing plasmids. Three hours following transfection, cell media were changed and TAT and TAT-IB1(s) peptides (1 μM) were added. The luciferase activities were measured 16 hours later using the "Dual Reporter System" from Promega after normalization to protein content. Addition of TAT-IB1(s) peptide blocked activation of c-Jun following MKK4 and MKK7 mediated activation of JNK. Because HeLa cells express JNK1 and JNK2 isoforms but not JNK3, we transfected cells with JNK3. Again, the TAT-IB(s) peptide inhibited JNK2 mediated activation of c-Jun.

Example 8

Inhibition of IL-1β Induced Pancreatic β-Cell Death by TAT-IB Peptides

We investigated the effects of the inventive L-TAT-IB(s) peptides on the promotion of β-cell apoptosis elicited by IL-1. βTC-3 cell cultures were incubated for 30 minutes with 1 μM of inventive L-TAT-IB1(s) peptides followed by 10 ng/mL of IL-1. A second addition of peptide (1 μM) was performed 24 hours later. Apoptotic cells were counted after two days of incubation with IL-1 β using propidium iodide (red stained cell are dead cells) and Hoechst 33342 (blue stained cell are cells with intact plasma membrane) nuclear staining. Addition of the inventive TAT-IB(s) peptides inhibited IL-1-induced apoptosis of βTC-3 cells cultured in the presence of IL-1 β for two days.

Long term inhibition of IL-1 induced cells death was examined by treating βTC-3 cells as described above, except that incubation of the cells with the peptides and IL-1 β was sustained for 12 days. Additional peptides (1 μM) were added each day and additional IL-1 β (10 ng/mL) was added every 2 days. The inventive TAT-IB1(s) peptide confers strong protection against apoptosis in these conditions. Taken together, these experiments provide evidence that inventive TAT-IB(s) peptides are biologically active molecules able to prevent the effects of JNK signaling on cell fate.

Example 9

Synthesis of Inventive all-D Retro-Inverso IB(s) Peptides

Peptides of the invention may be all-D amino acid peptides synthesized in reverse to prevent natural proteolysis (i.e. all-D retro-inverso peptides). An all-D retro-inverso peptide of the invention would provide a peptide with functional properties similar to the native peptide, wherein the side groups of the component amino acids would correspond to the native peptide alignment, but would retain a protease resistant backbone.

Retro-inverso peptides of the invention are analogs synthesized using D-amino acids by attaching the amino acids in a peptide chain such that the sequence of amino acids in the retro-inverso peptide analog is exactly opposite of that in the selected peptide which serves as the model. To illustrate, if the naturally occurring TAT protein (formed of L-amino acids) has the sequence GRKKRRQRRR [SEQ ID NO: 5], the retro-inverso peptide analog of this peptide (formed of D-amino acids) would have the sequence RRRQRRKKRG [SEQ ID NO: 6]. The procedures for synthesizing a chain of D-amino acids to form the retro-inverso peptides are known in the art (see e.g. Jameson et al., Nature, 368, 744-746 (1994); Brady et al., Nature, 368, 692-693 (1994); Guichard et al., J. Med. Chem. 39, 2030-2039 (1996)). Specifically, the retro-peptides were produced by classical F-mock synthesis and further analyzed by Mass Spectrometry. They were finally purified by HPLC.

Since an inherent problem with native peptides is degradation by natural proteases and inherent immunogenicity, the heterobivalent or heteromultivalent compounds of this invention will be prepared to include the "retro-inverso isomer" of the desired peptide. Protecting the peptide from natural proteolysis should therefore increase the effectiveness of the specific heterobivalent or heteromultivalent compound, both by prolonging half-life and decreasing the extent of the immune response aimed at actively destroying the peptides.

Example 10

Long Term Biological Activity of Inventive all-D Retro-Inverso IB(s) Peptides

Long term biological activity is predicted for the inventive D-TAT-IB(s) retro-inverso containing peptide heteroconjugate when compared to the native L-amino acid analog owing to protection of the inventive D-TAT-IB(s) peptide from degradation by native proteases, as shown in Example 5.

Inhibition of IL-1 β induced pancreatic β-cell death by the inventive D-TAT-IB1(s) peptide was analyzed. βTC-3 cells were incubated as described above for 30 minutes with one single addition of the indicated peptides (1, μM), then IL-1 (10 ng/ml) was added.

Apoptotic cells were then counted after two days of incubation with IL-1 β by use of Propidium Iodide and Hoechst 33342 nuclear staining. A minimum of 1,000 cells were counted for each experiment. Standard Error of the Means (SEM) are indicated, n=5. The D-TAT-IB1 peptide decreased IL-1 induced apoptosis to a similar extent as L-TAT-IB peptides.

Long term inhibition of IL-1P induced cell-death by the D-TAT-IB1 peptide was also analyzed. βTC-3 cells were incubated as above for 30 minutes with one single addition of the indicated peptides (1 μM), then IL-1 β (10 ng/ml) was added, followed by addition of the cytokine every two days. Apoptotic cells were then counted after 15 days of incubation with IL-1 by use of propidium iodide and Hoechst 33342 nuclear staining. Note that one single addition of the TAT-IB1 peptide does not confer long-term protection. A minimum of 1.000 cells were counted for each experiment. As a result, inventive D-TAT-IB1(s), but not inventive L-TAT-IB1(s), was able to confer long term (15 day) protection.

Example 11

Inhibition of Irradiation Induced Pancreatic β-Cell Death by TAT-IB(s) Peptides

JNK is also activated by ionizing radiation. To determine whether inventive TAT-IB(s) peptides would provide protection against radiation-induced JNK damage, "WiDr" cells were irradiated (30 Gy) in presence or absence of D-TAT, inventive L-TAT-IB1(s) or inventive D-TAT-IB1(s) peptides (1 μM added 30 minutes before irradiation). Control cells (CTRL) were not irradiated. Cells were analyzed 48 hours later by means of PI and Hoechst 3342 staining, as described above. N=3, SEM are indicated. Inventive L-TAT-IB1(s) and D-TAT-IB1(s) peptides were both able to prevent irradiation induced apoptosis in this human colon cancer line.

Example 12

Radioprotection to Ionizing Radiation by Inventive TAT-IB(s) Peptides

To determine the radioprotective effects of the inventive TAT-IB(s) peptides, C57B1/6 mice (2 to 3 months old) were irradiated with a Phillips RT 250 R-ray at a dose rate of 0.74 Gy/min (17 mA, 0.5 mm Cu filter). Thirty minutes prior to irradiation, the animals were injected i.p. with either TAT, inventive L-TAT-IB1(s) or inventive D-TAT-IB1(s) peptides (301 of a 1 mM solution). Briefly, mice were irradiated as follows: mice were placed in small plastic boxes with the head lying outside the box. The animals were placed on their back under the irradiator, and their neck fixed in a small plastic tunnel to maintain their head in a correct position. The body was protected with lead.

Prior to irradiation mice were maintained on standard pellet mouse chow, however post irradiation mice were fed with a semi-liquid food that was renewed each day.

The reaction of the lip mucosa was then scored by 2 independent observers according to the scoring system developed by Parkins et al. (Parkins et al, Radiotherapy & Oncology, 1: 165-173, 1983), in which the erythema status as well as the presence of edema, desquamation and exudation was quoted. Additionally, animals were weighed before each recording of their erythema/edema status.

The results of these experiments indicate that the inventive TAT-IB(s) peptides can protect against weight loss and erythema/edema associated with ionizing radiation.

Example 13

Suppression of JNK Transcription Factors by inventive L-TAT-IB1(s) Peptides

Gel retardation assays were carried out with an AP-1 doubled labeled probe (5'-CGC TTG ATG AGT CAG CCG GAA-3' (SEQ ID NO: 27). HeLa cell nuclear extracts that were treated or not for one hour with 5 ng/ml TNF-α, as indicated. TAT and inventive L-TAT-IB1(s) peptides were added 30 minutes before TNF-α. Only the part of the gel with the specific AP-1 DNA complex (as demonstrated by competition experiments with non-labeled specific and non-specific competitors) is shown.

Inventive L-TAT-IB1(s) peptides decrease the formation of the AP-1 DNA binding complex in the presence of TNF-α.

Example 14

Evaluation of the Neuroprotection Against Focal Cerebral Ischemia, in a Permanent MCAO Model—Determination of the Efficacity of the Protection at Different Doses. (see FIG. 3)

Focal cerebral ischemia was induced in 12-days-old rats. Pups were anesthetized in an induction chamber with 2% isoflurane and during the operation anaesthesia was maintained using a mask under 2% isoflurane. MCAO was induced by electrocoagulating a main branch of the middle cerebral artery (MCA). Rats were placed on the right side, and an oblique dermal incision was made between the ear and eye. After excision of the temporal muscle, the cranial bone was removed from the frontal suture to a level below the zygomatic arch. The left MCA, exposed just after its apparition over the rhinal fissure, was permanently electrocoagulated at the inferior cerebral vein level before the MCA bifurcated into frontal and parietal branches. The cranial skin incision was then closed. Rat pups were then placed in an incubator maintained at 37° C. until they awoke, and were then transferred to their mother.

6 hours later an inventive chimeric D-TAT-IB1(s) peptide according to SEQ ID NO: 11 was injected intraperitoneally. 24 hours after the coagulation, the rats were anesthetized with chloral hydrate and perfused through the ascending aorta with 4% paraformaldehyde in PBS. Brains were then removed and kept for 2 hours in the same fixative solution, and placed in a gradient of 30% sucrose in PBS for about 15 hours at 4° C. Brains were frozen in isopentane (−40° C.) and stored at −20° C. Coronal cryostat sections of 50 μm were collected on glass slides. The sections were stained with cresyl violet. Each tenth section was analyzed and the total volume of the lesion was calculated using the Neuroleucida programme. In the control group A, the mean lesion volume was 21.47 mm$^3$. All the treated groups have a lower mean than the control group. A significant statistic difference is observed between group A and groups C, E and F (one-tailed t-test, p=0.030, p=0.002, p=0.001 respectively). The results are shown in FIG. 4.

As a result, these data support the conclusion that the inventive chimeric D-TAT-IB1(s) peptide according to SEQ ID NO: 11, administered at a dose of 11 mg/kg, 3 mg/kg, 0.3 mg/kg and 0.03 mg/kg, contributes to a cerebral protection. Results at a dose of 1 mg/kg, 0.003 mg/kg and 0.0003 compared to saline group suggest that the total sample was not large enough to reach a significant difference. The best protection is observed at the dose of 0.03 mg/kg.

Example 15

Figure 4:
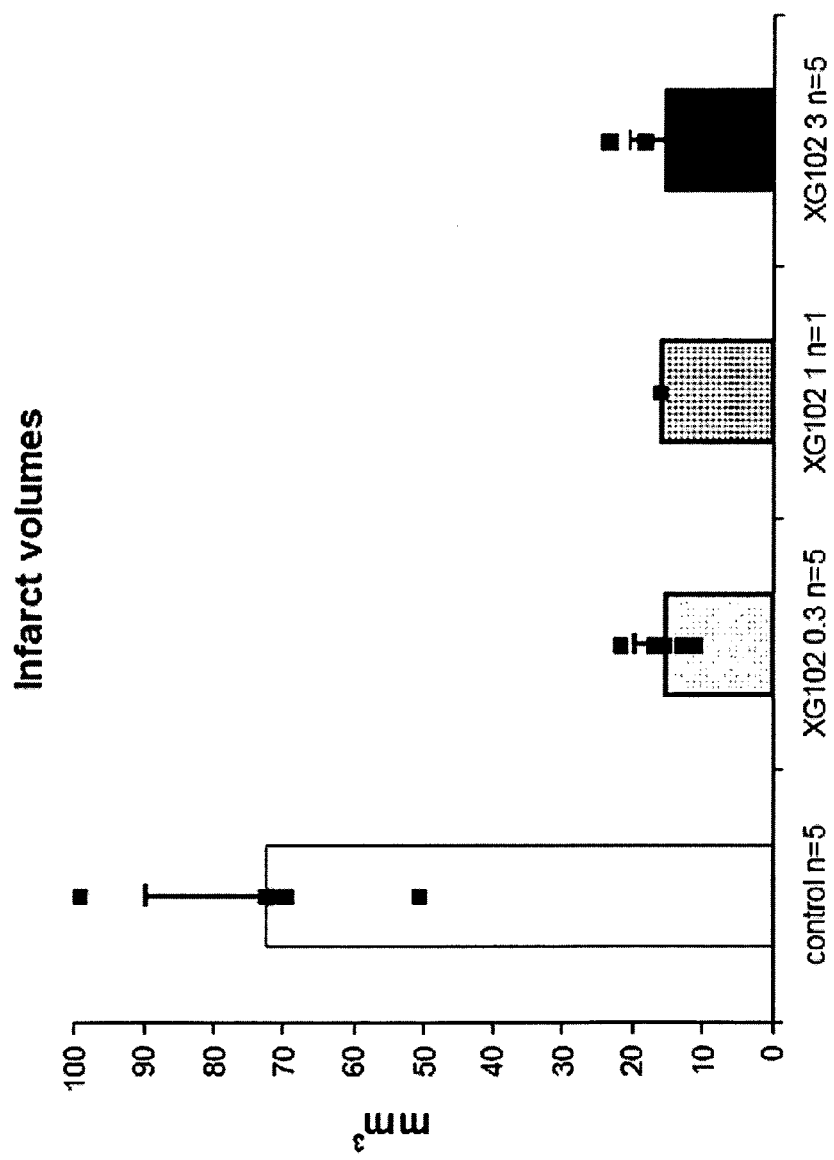
FIG. 4 illustrates the evaluation of neuroprotection by an inventive chimeric peptide according to SEQ ID NO: 11 after i.v. administration against focal cerebral ischemia, in a transient MCAO model. Subsequent to provoking ischemia in adult mice, the mice were killed 48 h after reperfusion. Serial cryostat sections were prepared and infarct volumes were calculated. As can be seen from FIG. 4, the inventive chimeric peptide provides efficient neuroprotection.

Evaluation of Neuroprotection by Inventive Chimeric Peptides after IV Administration Against Focal Cerebral Ischaemia, in a Transient MCAO Model (See FIG. 4)

Transient ischemia in adult mice. Using male ICR-CD1 mice (6 weeks old; 18-37 g; Harlan), we provoked ischemia by introducing a filament from the common carotid artery into the internal carotid and advancing it into the arterial circle, thereby occluding the middle cerebral artery. We measured regional cerebral blood flow by laser Doppler flowmetry, with a probe fixed on the skull throughout the ischemia until 10 min after reperfusion. Rectal temperature was measured and maintained at 37° C. The mice were killed 48 h after reperfusion. Serial cryostat sections 20 μm thick were traced using a computer-microscope system equipped with the Neurolucida program (MicroBrightField) and the volumes of the ischemic area and of the whole brain were calculated (blinded) with the Neuroexplorer program.

XG-102 0.3=0.3 mg/kg, XG-102 1=1 mg/kg, XG-102 5=5 mg/kg

The infarct volume sizes (mm$^3$) after bolus iv administration of placebo and XG-102 0.3, 1.3 mg/kg 6 hours after reperfusion (30 minutes clamp) in an adult mice model were as follows.

| infarcts | moyenne | ecart type |
|---|---|---|
| control n = 5 | 72 | 17 |
| XG102 0.3 n = 5 | 16 | 4 |
| XG102 1 n = 1 | 16 | |
| XG102 3 n = 5 | 15 | 5 |

Example 16

Figure 5:
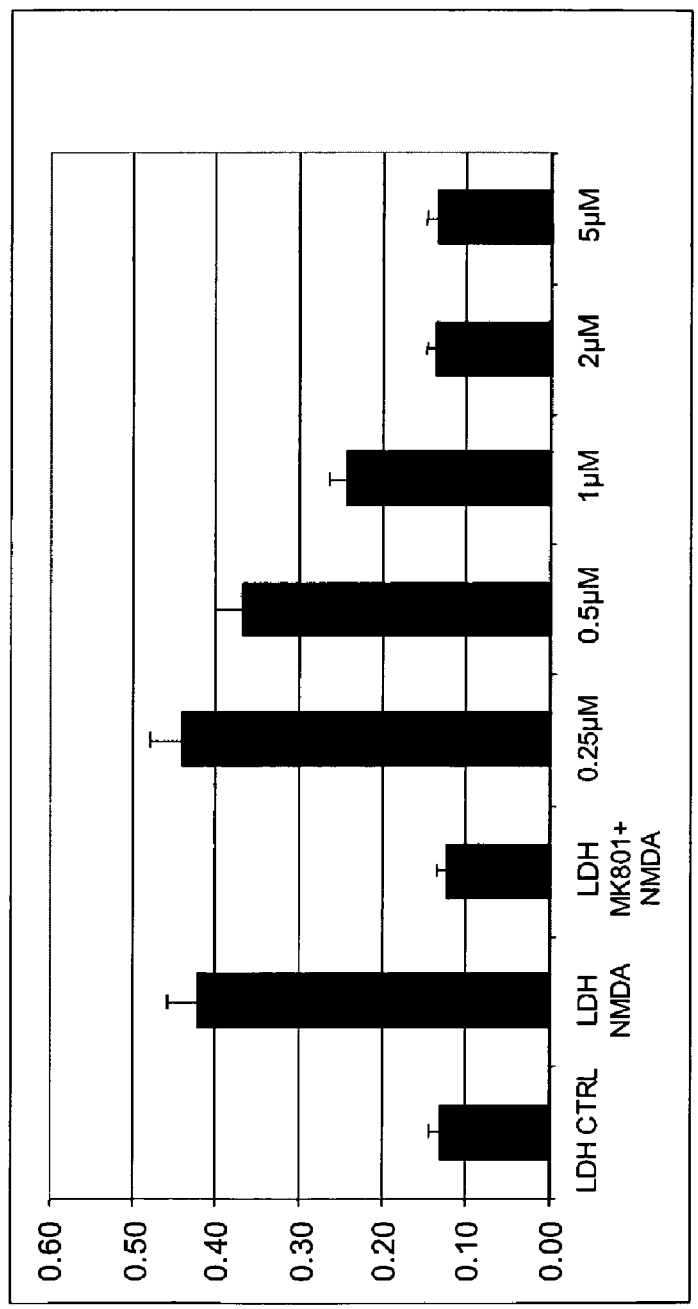
FIG. 5 shows the results of an assay on neuronal cultures carried out by measuring LDH release following NMDA stimulation. The results clearly indicate a neuroprotective effect of the inventive chimeric D-JNKI1 peptide (SEQ ID NO: 11), since degenerative changes due to NMDA exposure were completely inhibited as indicated by the absence of significant LDH release above controls.

Assay on Neuronal Cultures by Measuring LDH Release Following NMDA Stimulation (see FIG. 5)

The neuroprotective effect of the D-TAT-IB (generic)(s)/D-JNKI1 peptide (SEQ ID NO: 12) was evaluated in sister cultures pre-treated for 30 min with the indicated concentrations of peptides or MK-801 before continuous exposure to 100 μM NMDA. After 12 h of NMDA treatment, in cultures pretreated with 5 μM of D-TAT-IB (generic)(s)/D-JNKI1 the degenerative changes due to NMDA exposure were completely inhibited as indicated by the absence of significant LDH release above controls (FIG. 5). The morphological appearance, number and distribution of the neurons were indistinguishable from the controls.

Cortical neuronal culture. We dissected small pieces of cortex from the brains of two day old rat pups, incubated them with 200 units of papain for 30 min at 34° C., and then plated the neurons at densities of approximately 1×10$^6$ cells/plate on dishes pre-coated with 100 μg/ml poly-D-lysine. The plating medium consisted of B27/Neurobasal (Life Technologies, Gaithersburg, Md.) supplemented with 0.5 mM glutamine, 100 U/ml penicillin and 100 ug/ml streptomycin.

Lactate dehydrogenate (LDH) cytotoxicity assay. LDH released into the bathing medium 12, 24 and 48 h after NMDA administration was measured using the Cytotox 96 non-radioactive cytotoxicity assay kit (Promega, WI) (see FIG. 5).

Example 17

Figure 6:
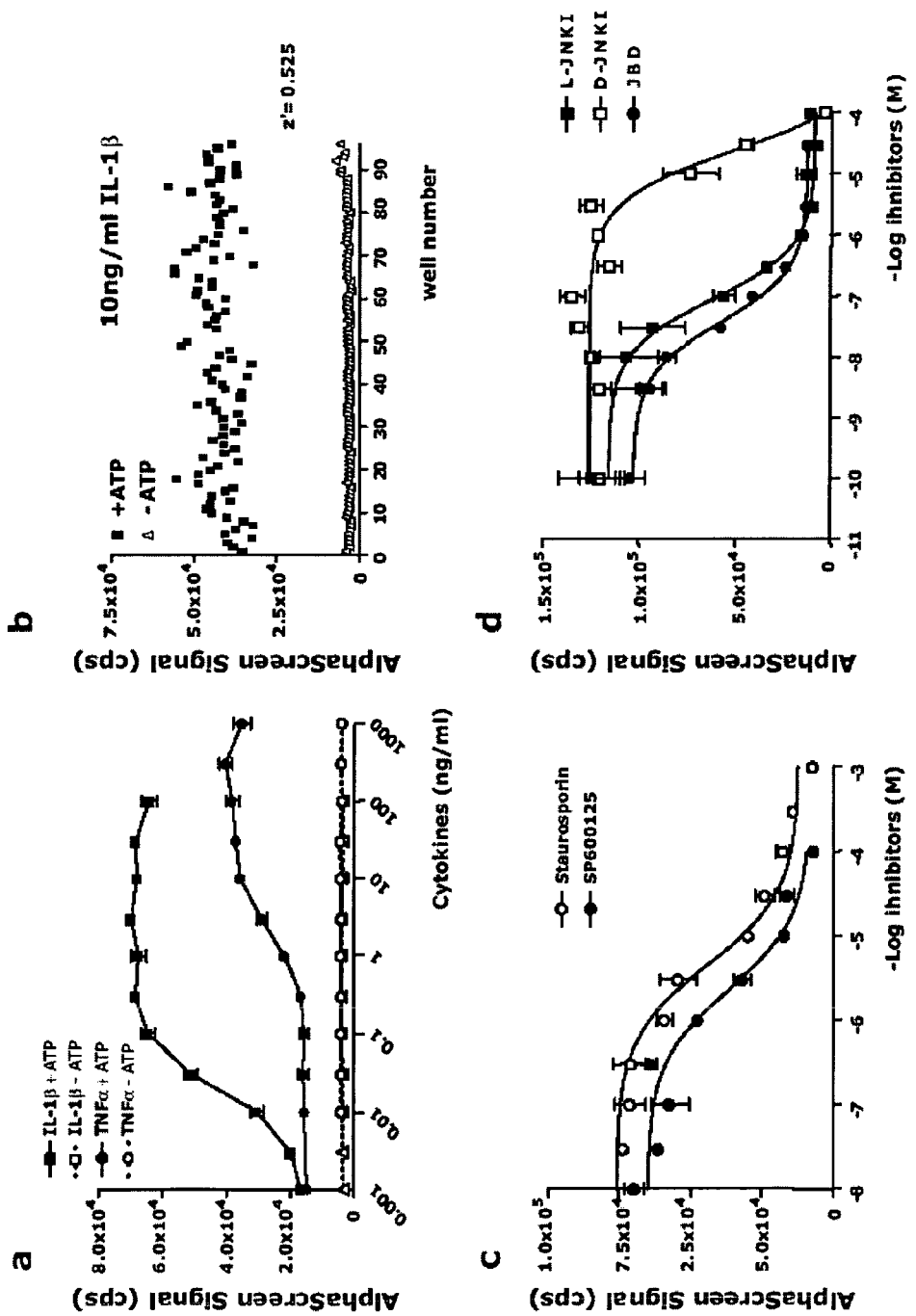
FIG. 6 depicts the results of the inhibition of endogeneous JNK-activity in HepG2 cells using inventive fusion peptides according to SEQ ID NOs: 9 and 11 in an one-well approach. As can be seen from FIG. 6, particularly panel d in FIG. 6, D-TAT-IB1(s) according to SEQ ID NO: 11 (here abbreviated as D-JNKI) effectively inhibits JNK activity, even better than L-TAT-IB1(s) according to SEQ ID NO: 9 (here abbreviated as L-JNKI).
Figure 7:
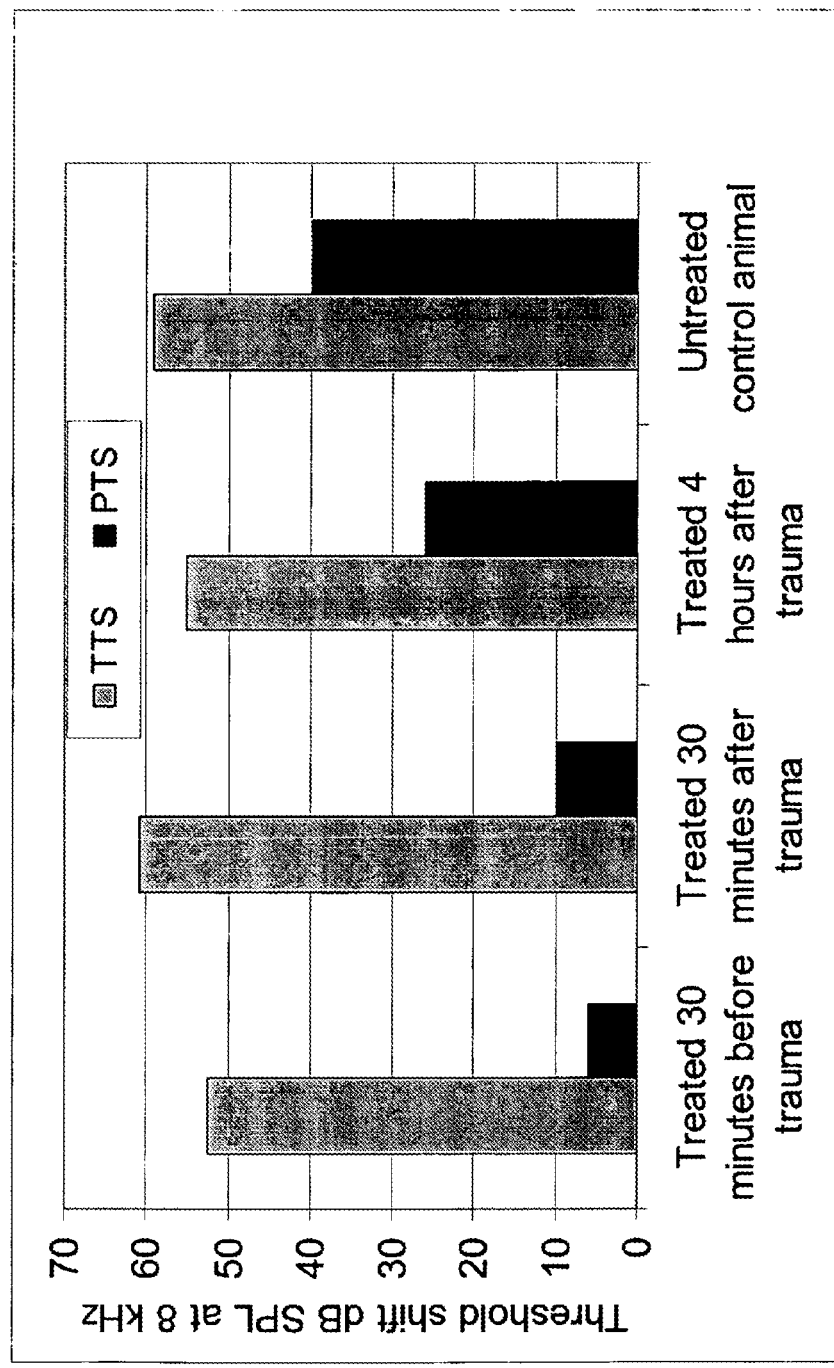
FIG. 7 shows the protecting effect of D-TAT-IB1(s) Protection against permanent hearing loss. Changes of the hearing threshold level (dB sound pressure level) in guinea pigs following noise trauma (120 dB at 6 kHz during 30 minutes) at 8 kHz, the maximally impacted frequency, measured 20 minutes (temporary threshold shift, TTS, grey) and 15 days post noise exposure (permanent threshold shift). Guinea pigs received D-TAT-IB1(s) in a hyaluronic acid gel deposited onto the cochlear round window membrane either 30 minutes before, 30 minutes after or 4 hours after noise trauma; untreated ears served as control. TTS was measured 20 minutes post noise trauma, while PTS (black), which corresponds to permanent hearing loss, was determined after 15 days. As shown, D-TAT-IB1(s) not only protects substantially against permanent hearing loss from noise trauma if applied preventively before the noise exposure, but also in a time-dependent fashion if administered after trauma. PTS in treated ears was significantly lower for administration of D-TAT-IB1(s) 30 minutes and 4 hours post trauma than in untreated control ears.

Inhibition of Endogenous JNK Activity in HepG2 Cells Using an All-In One Well Approach (See FIG. 6)

HepG2 cells were seeded at 3'000 cells/well the day prior the experiment. Then, increasing concentrations of either interleukin-1β [IL-1β(v)] or tumor necrosis factor α [TNFα (•)] (a) were added to activate JNK for 30 minutes. Cells were lysed in 20 mM Hepes, 0.5% Tween pH 7.4 and processed for AlphaScreen JNK. (b) Z' for the JNK activity induced by 10 ng/ml IL-1β and measured in 384 wells/plate (n=96). (c) Inhibition of endogenous IL-1 β-induced JNK activity with chemical JNK inhibitors [staurosporin (°) and SP600125 (•)]. (d) Effect of peptidic inhibitors L-TAT-IB1(s) according to SEQ ID NO: 9 [here abbreviated as L-JNKi (v)] and D-TAT-IB1(s) according to SEQ ID NO: 11 (here abbreviated as D-JNKi (♦) and JBDs (•) (corresponds to L-JNKI without the TAT sequence)] on IL-1α dependent JNK activity. All panels are representative of three independent experiments (n=3).

Methods: Alphascreen Kinase Assay

Principle: AlphaScreen is a non-radioactive bead-based technology used to study biomolecular interactions in a microplate format. The acronym ALPHA stands for Amplified Luminescence Proximity Homogenous Assay. It involves a biological interaction that brings a "donor" and an "acceptor" beads in close proximity, then a cascade of chemical reactions acts to produce an amplified signal. Upon laser excitation at 680 nm, a photosensitizer (phthalocyanine) in the "donor" bead converts ambient oxygen to an excited singlet state. Within its 4 μsec half-life, the singlet oxygen molecule can diffuse up to approximately 200 nm in solution and if an acceptor bead is within that proximity, the singlet oxygen reacts with a thioxene derivative in the "acceptor" bead, generating chemiluminescence at 370 nm that further activates fluorophores contained in the same "acceptor" bead. The excited fluorophores subsequently emit light at 520-620 nm. In the absence of an acceptor bead, singlet oxygen falls to ground state and no signal is produced.

Kinase reagents (B-GST-cJun, anti P-dun antibody and active JNK3) were first diluted in kinase buffer (20 mM Tris-HCl pH 7.6, 10 mM MgCl$_2$, 1 mM DTT, 100 μM Na$_3$VO$_4$, 0.01% Tween-20) and added to wells (15 μl). Reactions were then incubated in presence of 10 μM of ATP for 1 h at 23° C. Detection was performed by an addition of 10 μl of beads mix (Protein A acceptor 20 μg/ml and Streptavidin donor 20 μg/ml), diluted in detection buffer (20 mM Tris-HCl pH 7.4, 20 mM NaCl, 80 mM EDTA, 0.3% BSA), followed by an another one-hour incubation at 23° C. in the dark. For measurement of JNK endogenous activity, kinase assays were performed as described above except active JNK3 was replaced by cells lysates and reaction kinase components were added after the cells lysis. B-GST-cjun and P-cJun antibody were used at the same concentrations whereas ATP was used at 50 μM instead of 10 μM. AlphaScreen signal was analyzed directly on the Fusion or En Vision apparatus.

Example 18

Treatment of Noise Trauma

D-TAT-IB1(s) was applied onto the round window membrane of the cochlea of 3 groups of guinea pigs (each group with 6 animals) in 2 microliters of a gel formulation of 2.6% buffered hyaluronic acid (Hylumed, Genzyme Corp.) at a concentration of 100 µM either 30 minutes before noise trauma (120 dB at 6 kHz during 30 minutes) or 30 minutes or 4 hours thereafter. Untreated ears served as control. Hearing threshold shifts were evaluated by auditory brainstem response measurements 20 minutes after noise trauma (temporary threshold shift, TTS) and 15 days following the trauma (permanent threshold shift, PTS). Administration of D-TAT-IB1(s) protected against permanent hearing loss even if applied after exposure to excessive noise compared to non-treated ears. The protective effect was stronger the earlier D-TAT-IB1(s) was administered after the noise trauma. Thus, D-TAT-IB1(s) is a very effective otoprotective compound in case of noise trauma.

From the foregoing detailed description of the specific embodiments of the invention, it should be apparent that unique cell-permeable bioactive chimeric peptides and JNK inhibitor sequences have been described. Although particular embodiments have been disclosed herein in detail, this has been done by way of example for purposes of illustration only, and is not intended to be limiting with respect to the scope of the appended claims which follow. In particular, it is contemplated by the inventor that various substitutions, alterations, and modifications may be made to the invention without departing from the spirit and scope of the invention as defined by the claims.

---

What is claimed is:

1. A chimeric peptide consisting of a first domain and a second domain directly linked by a covalent bond or linked by a linker sequence of 1 to 10 amino acids,
the first domain comprising a trafficking sequence, and
the second domain consisting of a c-Jun N-terminal kinase (JNK) inhibitor sequence of SEQ ID NO: 2 or a variant sequence of SEQ ID NO: 2 with 1 or 2 amino acids deleted from either terminus of SEQ ID NO: 2,
wherein the trafficking sequence comprises the amino acid sequence of SEQ ID No: 5, 6, 7 or 8 or a sequence variant of SEQ ID NO: 5 or 6 with 1 or 2 amino acids deleted from either terminus of SEQ ID NO: 5 or 6, and wherein the trafficking sequence and the JNK inhibitor sequence are composed exclusively of D-enantiomeric amino acids.

2. The peptide of claim 1, wherein the trafficking sequence comprises the amino acid sequence of a human immunodeficiency virus TAT polypeptide.

3. The peptide of claim 1, wherein the trafficking sequence comprises the amino acid sequence of SEQ ID NO: 5, 6, 7 or 8.

4. The peptide of claim 1, wherein the trafficking sequences augments cellular uptake of the peptide.

5. The peptide of claim 1, wherein the trafficking sequence directs nuclear localization of the peptide.

6. The peptide of claim 1, wherein the peptide comprises the amino acid sequence of any of SEQ ID NO: 11, or a fragment, or variant thereof.

7. A pharmaceutical composition comprising a chimeric peptide of claim 1 and a pharmaceutically acceptable carrier.

8. A Kit comprising a chimeric peptide of claim 1, and/or a nucleic acid encoding a chimeric peptide of claim 1, and/or a vector comprising a nucleic acid encoding a chimeric peptide of claim 1, and/or a cell comprising the vector comprising a nucleic acid encoding a chimeric peptide of claim 1, and/or an antibody which binds immunospecifically to to a chimeric peptide of claim 1.

9. The peptide of claim 1, comprising at least one modification at the C-terminus and/or at least one modification at the N-terminus.

10. The peptide of claim 9, wherein the peptide comprises an amidation modification at the C-terminus and/or an $NH_2$-protection group modification at the N-terminus.

11. The peptide of claim 10, wherein the peptide comprises an acylation modification at the N-terminus.

12. The peptide of claim 9, wherein the peptide comprises the amino acid sequence of SEQ ID NO: 11.

13. The peptide of claim 12, wherein the peptide comprises an amidation modification at the C-terminus.

14. The peptide of claim 1, wherein the peptide is selected from the group consisting of
QSRPVQPFLNLTTPRKPR-$X_n$-RRRQRRKKRG,
SRPVQPFLNLTTPRKPR-$X_n$-RRRQRRKKRG,
DQSRPVQPFLNLTTPRKP-$X_n$-RRRQRRKKRG,
DQSRPVQPFLNLTTPRK-$X_n$-RRRQRRKKRG,
QSRPVQPFLNLTTPRKP-$X_n$-RRRQRRKKRG,
SRPVQPFLNLTTPRKP-$X_n$-RRRQRRKKRG,
SRPVQPFLNLTTPRK-$X_n$-RRRQRRKKRG,
QSRPVQPFLNLTTPRKPR-$X_n$-RRRQRRKKR,
QSRPVQPFLNLTTPRKPR-$X_n$-RRRQRRKK,
QSRPVQPFLNLTTPRKPR-$X_n$-RRRQRRKKRG,
QSRPVQPFLNLTTPRKPR-$X_n$-RQRRKKRG,
QSRPVQPFLNLTTPRKPR-$X_n$-RRRQRRKKR,
QSRPVQPFLNLTTPRKPR-$X_n$-RQRRKKR,
QSRPVQPFLNLTTPRKPR-$X_n$-RQRRKK
SRPVQPFLNLTTPRKPR-$X_n$-RRRQRRKKR,
DQSRPVQPFLNLTTPRKP-$X_n$-RRRQRRKKR,
DQSRPVQPFLNLTTPRK-$X_n$-RRRQRRKKR,
SRPVQPFLNLTTPRKP-$X_n$-RRRQRRKKR,
SRPVQPFLNLTTPRK-$X_n$-RRRQRRKKR, DQSRPVQPFLNLTTPRKP-$X_n$-RRRQRRKK,
DQSRPVQPFLNLTTPRK-$X_n$-RRRQRRKK,
QSRPVQPFLNLTTPRKP-$X_n$-RRRQRRKK,
SRPVQPFLNLTTPRKP-$X_n$-RRRQRRKK,
SRPVQPFLNLTTPRK-$X_n$-RRRQRRKK,
SRPVQPFLNLTTPRKPR-$X_n$-RRQRRKKR,
DQSRPVQPFLNLTTPRKP-$X_n$-RRQRRKKR,
DQSRPVQPFLNLTTPRK-$X_n$-RRQRRKKR,
QSRPVQPFLNLTTPRKP-$X_n$-RRQRRKKR,
SRPVQPFLNLTTPRKP-$X_n$-RRQRRKKRG,
SRPVQPFLNLTTPRK-$X_n$-RRQRRKKRG,
SRPVQPFLNLTTPRKPR-$X_n$-RRQRRKKRG,
DQSRPVQPFLNLTTPRK-$X_n$-RRQRRKKRG,
QSRPVQPFLNLTTPRKP-$X_n$-RRQRRKKRG,
SRPVQPFLNLTTPRKP-$X_n$-RRQRRKKRG,
SRPVQPFLNLTTPRKPR-$X_n$-RQRRKKRG,
DQSRPVQPFLNLTTPRKP-$X_n$-RQRRKKRG,
DQSRPVQPFLNLTTPRK-$X_n$-RQRRKKRG,
QSRPVQPFLNLTTPRKP-$X_n$-RQRRKKRG,
SRPVQPFLNLTTPRKP-$X_n$-RQRRKKRG,
SRPVQPFLNLTTPRK-$X_n$-RQRRKKRG,
QSRPVQPFLNLTTPRKP-$X_n$-RRRQRRKKR,
QSRPVQPFLNLTTPRKPR-$X_n$-RRRQRRKK, and
DQSRPVQPFLNLTTPRKP-$X_n$-RRQRRKKRG,
  wherein X is any L enantiomer or D enantiomer amino acid,
  n is 0-10, and
  the amino acids except for X are D enantiomer amino acids.

15. The peptide of claim 14, wherein n is 1-10.

16. The peptide of claim 14, wherein n is 1-5.

17. The peptide of claim 14, wherein X is an L enantiomer amino acid.

18. The peptide of claim 14, wherein X is a D enantiomer amino acid.

* * * * *